(12) United States Patent
El-Araby et al.

(10) Patent No.: US 11,174,233 B1
(45) Date of Patent: *Nov. 16, 2021

(54) ANTI-CANCER COMPOUNDS HAVING OXAZOLONE DERIVATION

(71) Applicant: King Abdulaziz University, Jeddah (SA)

(72) Inventors: Moustafa E. El-Araby, Jeddah (SA); Abdelsattar M. Omar, Jeddah (SA); Ahmed Esmat, Jeddah (SA); Farid Ahmed, Jeddah (SA); Azizah M. Malebari, Jeddah (SA); Ashraf B. Abdel-Naim, Jeddah (SA); Thikryat Neamatallah, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/377,530

(22) Filed: Jul. 16, 2021

Related U.S. Application Data

(63) Continuation of application No. 16/681,086, filed on Nov. 12, 2019.

(51) Int. Cl.
| | |
|---|---|
| C07D 233/96 | (2006.01) |
| C07D 405/06 | (2006.01) |
| C07D 307/52 | (2006.01) |
| C07C 237/22 | (2006.01) |

(52) U.S. Cl.
CPC .......... *C07D 233/96* (2013.01); *C07C 237/22* (2013.01); *C07D 307/52* (2013.01); *C07D 405/06* (2013.01); *C07C 2601/16* (2017.05)

(58) Field of Classification Search
CPC .............. C07D 405/06; C07D 233/96
See application file for complete search history.

(56) References Cited

FOREIGN PATENT DOCUMENTS

WO 02/48114 A1 6/2002

OTHER PUBLICATIONS

Jia et al., Chinese Journal of Chemistry, (2011), v29, p. 1869-1872.*
Beckmann, et al. ; A strategy for the diversity-oriented synthesis of macrocyclic scaffolds using multidimensional Coupling ; Nature Chemistry 5 ; pp. 861-867 ; Aug. 25, 2013 ; 12 Pages.
Pevarello, et al. ; Additions and Corrections, vol. 45 ; J. Med. Chern. 48 ; 2005 ; Abstract Only ; 1 Page.
Pevarello, et al. ; 3-Aminopyrazole Inhibitors of CDK2/Cyclin A as Antitumor Agents. 2. Lead Optimization ; Journal of Medicinal Chemistry, 45, 8 ; pp. 2944-2956 ; Mar. 29, 2005 ; Abstract Only ; 5 Pages.
Maji, et al. ; A unique example of a pseudo-peptide containing noncoded amino acids self-assembling into a supramolecular B-sheet-like structure in crystals ; Letters in peptide Science 8 ; pp. 61-67 ; Oct. 1, 2001 ; Abstract Only ; 2 Pages.
Helal et al. ("Synthesis and characterization of new types of 2-(6-methoxy-2-naphthyl)propionamide derivatives as potential antibacterial and antifungal agents." Medicinal Chemistry Research vol. 22, pp. 5598-5609(2013). (Year: 2013).

\* cited by examiner

*Primary Examiner* — Yong L Chu
(74) *Attorney, Agent, or Firm* — Oblon, McClelland, Maier & Neustadt, L.L.P.

(57) ABSTRACT

Cytotoxic compounds containing a phenyl core, amide link(s), an imidazolinone or a propenamide moiety. Also described are pharmaceutical compositions incorporating the cytotoxic compounds and methods for treating cancer. These compounds are cytotoxic against breast, prostate, and leukemia cancer cell lines via dual inhibition of Src kinases and tubulin.

3 Claims, 16 Drawing Sheets

Conditions: (a) Oxalyl chloride, dichloromethane, N,N-dimethylformamide (cat. amount). (b) $R_3 R_4 NH$, Ethyl diisopropylamine, dichloromethane. (c) Tin chloride II dihydrate, ethyl acetate, water, heat, or H-Cube Pro, Pd-C (10%), 10 atm, 40 °C, ethyl acetate.

Conditions: (a) Acetic anhydride, sod. acetate, heat (b) Amine 4a-j, pyridine, heat (c) Amine 4a-j, acetonitrile, heat.

ANTI-CANCER COMPOUNDS HAVING OXAZOLONE DERIVATION

CROSS-REFERENCE TO RELATED APPLICATIONS

The present application is a Continuation of U.S. application Ser. No. 16/681,086, having a filing date of Nov. 12, 2019, presently pending. The present application is related to U.S. application Ser. No. 16/985,620, now U.S. Pat. No. 10,844,022 having a filing date of Aug. 5, 2020 which is a Continuation of U.S. application Ser. No. 16/681,086.

STATEMENT OF FUNDING ACKNOWLEDGEMENT

This project was funded by the Deanship of Scientific Research (DSR), King Abdulaziz University, Jeddah, the Kingdom of Saudi Arabia, under grant number RG-4-166-40.

BACKGROUND OF THE INVENTION

Technical Field

The present disclosure relates to compounds with anti-proliferative activity and a method of treating cancer.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The abnormal expression of protein tyrosine kinases (PTK) leads to cell proliferation disorder and is associated with tumor invasion, metastasis, and angiogenesis. As a result, a variety of PTKs have been used as targets for screening anti-tumor drugs [Drake, J. M.; Lee, J. K.; Witte, O. N., Clinical targeting of mutated and wild-type protein tyrosine kinases in cancer. *Molecular and cellular biology* 2014, 34 (10), 1722-32].

Currently, all PTK inhibitors that are clinically available are those that occupy ATP pockets. Since ATP is a common cofactor that is inherently concentrated in cells (mM), large quantities of the inhibitor must be delivered to the ATP pockets to achieve adequate selectivity and affinity. A practical, though under-utilized approach, is to develop kinase inhibitors that bind to the substrate site. This approach should be appealing because each kinase is specific for a unique peptide sequence.

The Src family of kinase enzymes (SFK) are non-receptor tyrosine kinases essential in signaling machinery [Guo, W.; Giancotti, F. G., Integrin signalling during tumour progression. *Nature reviews Molecular cell biology* 2004, 5 (10), 816]. Members of SFKs include Src, Yes, Fyn, Fgr, Lck, Hck, Blk, Yrk, and Lyn. SFKs are important for fundamental cellular processes such as cell growth, functions, survival, proliferation, differentiation, and migration [Lieu, C.; Kopetz, S., The SRC family of protein tyrosine kinases: a new and promising target for colorectal cancer therapy. *Clinical colorectal cancer* 2010, 9 (2), 89-94]. Aberrant activities of SFK have been linked to a variety of cancers including those of the prostate, breast, colon, lungs, pancreas, brain, melanocytes, and bone marrow [Frame, M. C.; Roskoski, R., Src Family Tyrosine Kinases. In *Reference Module in Life Sciences*, Elsevier: 2017]. Inhibitors of Src kinase such as dasatinib, bosutinib, saracatinib, KX-01, and KX-02 have been recently developed for cancer treatment [Elsberger, B.; Stewart, B.; Tatarov, O.; Edwards, J Is Src a viable target for treating solid tumours? *Current cancer drug targets* 2010, 10 (7), 683-694; Rothschild, S. I.; Gautschi, O.; Haura, E. B.; Johnson, F. M., Src inhibitors in lung cancer: current status and future directions. *Clinical lung cancer* 2010, 11 (4), 238-42; and Smolinski, M. P.; Bu, Y.; Clements, J.; Gelman, I. H.; Hegab, T.; Cutler, D. L.; Fang, J. W. S.; Fetterly, G.; Kwan, R.; Barnett, A.; Lau, J. Y. N.; Hangauer, D. G., Discovery of Novel Dual Mechanism of Action Src Signaling and Tubulin Polymerization Inhibitors (KX2-391 and KX2-361). *Journal of medicinal chemistry* 2018, 61 (11), 4704-4719, each incorporated herein by reference in their entirety]. Despite these recent efforts, there is still a need to develop more effective non-ATP competitive inhibitors as anti-proliferative agents.

In view of the forgoing, one objective of the present disclosure is to provide therapeutic compounds with anti-cancer activities, a pharmaceutical composition comprising thereof, and a method for cancer treatment.

BRIEF SUMMARY OF THE INVENTION

According to a first aspect, the present disclosure relates to a compound selected from the group consisting of a compound of formula (I),

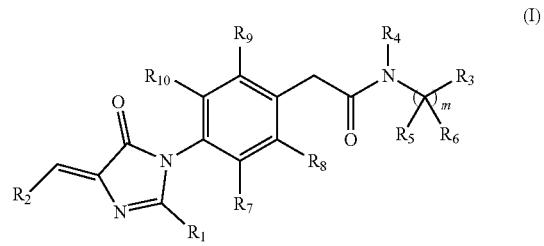

a salt thereof, a solvate thereof, a tautomer thereof, and a stereoisomer thereof;

a compound of formula (II),

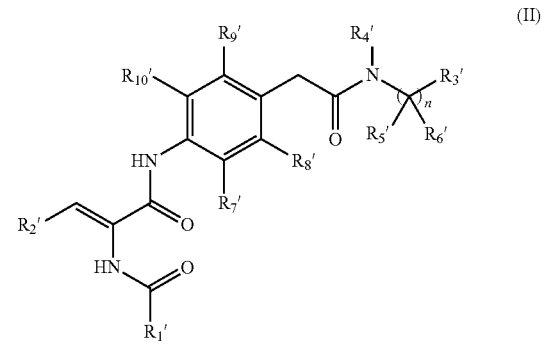

a salt thereof, a solvate thereof, a tautomer thereof, and a stereoisomer thereof;

a compound of formula (III),

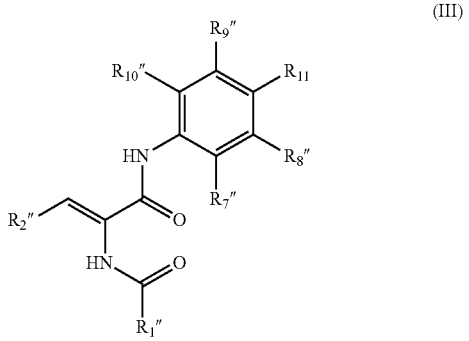

a salt thereof, a solvate thereof, a tautomer thereof, and a stereoisomer thereof; and mixtures thereof, wherein (i) $R_1$, $R_1'$, and $R_1''$ are independently selected from the group consisting of an optionally substituted alkyl, an optionally substituted cycloalkyl, an optionally substituted arylalkyl, and an optionally substituted aryl, (ii) $R_2$, $R_2'$, and $R_2''$ are independently an optionally substituted aryl, or an optionally substituted heteroaryl, (iii) $R_3$ and $R_3'$ are independently an optionally substituted aryl, or an optionally substituted heteroaryl, (iv) $R_4$ and $R_4'$ are independently selected from the group consisting of a hydrogen, an optionally substituted alkyl, an optionally substituted cycloalkyl, an optionally substituted arylalkyl, and an optionally substituted aryl, (v) $R_5$, $R_5'$, $R_6$, and $R_6'$ are independently selected from the group consisting of a hydrogen, an optionally substituted alkyl, an optionally substituted cycloalkyl, and an optionally substituted arylalkyl, (vi) $R_7$, $R_7'$, $R_7''$, $R_8$, $R_8'$, $R_8''$, $R_9$, $R_9'$, $R_9''$, $R_{10}$, $R_{10}'$, $R_{10}''$, and $R_{11}$ are independently selected from the group consisting of a hydrogen, an optionally substituted alkyl, an optionally substituted cycloalkyl, an optionally substituted arylalkyl, a hydroxy, and a halogen, and (vii) m and n are independently an integer in a range of 1-3.

In one embodiment, the compound is represented by formula (I), or a salt thereof, a solvate thereof, a tautomer thereof, or a stereoisomer thereof, and $R_1$ is methyl, or phenyl.

In one embodiment, the compound is represented by formula (I), or a salt thereof, a solvate thereof, a tautomer thereof, or a stereoisomer thereof, and $R_2$ is selected from the group consisting of phenyl, p-chlorophenyl, p-hydroxy-m-methoxyphenyl, p-methoxyphenyl, and 2-furanyl.

In one embodiment, the compound is represented by formula (I), or a salt thereof, a solvate thereof, a tautomer thereof, or a stereoisomer thereof, and $R_3$ is phenyl.

In one embodiment, the compound is represented by formula (I), or a salt thereof, a solvate thereof, a tautomer thereof, or a stereoisomer thereof, and $R_4$ is hydrogen.

In one embodiment, the compound is represented by formula (I), or a salt thereof, a solvate thereof, a tautomer thereof, or a stereoisomer thereof, and $R_5$ and $R_6$ are hydrogen.

In one embodiment, the compound is represented by formula (II), or a salt thereof, a solvate thereof, a tautomer thereof, or a stereoisomer thereof, and $R_1'$ is methyl, or phenyl.

In one embodiment, the compound is represented by formula (II), or a salt thereof, a solvate thereof, a tautomer thereof, or a stereoisomer thereof, and $R_2'$ is selected from the group consisting of phenyl, p-chlorophenyl, p-hydroxy-m-methoxyphenyl, p-methoxyphenyl, and p-fluoro-o-methylphenyl.

In one embodiment, the compound is represented by formula (II), or a salt thereof, a solvate thereof, a tautomer thereof, or a stereoisomer thereof, and $R_3'$ is selected from the group consisting of phenyl, p-methoxyphenyl, 2-furanyl, p-fluorophenyl, and 4-1,1'-biphenyl.

In one embodiment, the compound is represented by formula (II), or a salt thereof, a solvate thereof, a tautomer thereof, or a stereoisomer thereof, and $R_4'$ is hydrogen or methyl.

In one embodiment, the compound is represented by formula (II), or a salt thereof, a solvate thereof, a tautomer thereof, or a stereoisomer thereof, and $R_5'$ is hydrogen, and $R_6'$ is hydrogen, or methyl.

In one embodiment, the compound is represented by formula (III), or a salt thereof, a solvate thereof, a tautomer thereof, or a stereoisomer thereof, and $R_1''$ is methyl, $R_2''$ is phenyl, and $R_{11}$ is methyl.

In one embodiment, $R_7$, $R_7'$, $R_7''$, $R_8$, $R_8'$, $R_8''$, $R_9$, $R_9'$, $R_9''$, $R_{10}$, $R_{10}'$, and $R_{10}''$ are hydrogen.

In one embodiment, the compound is selected from the group consisting of

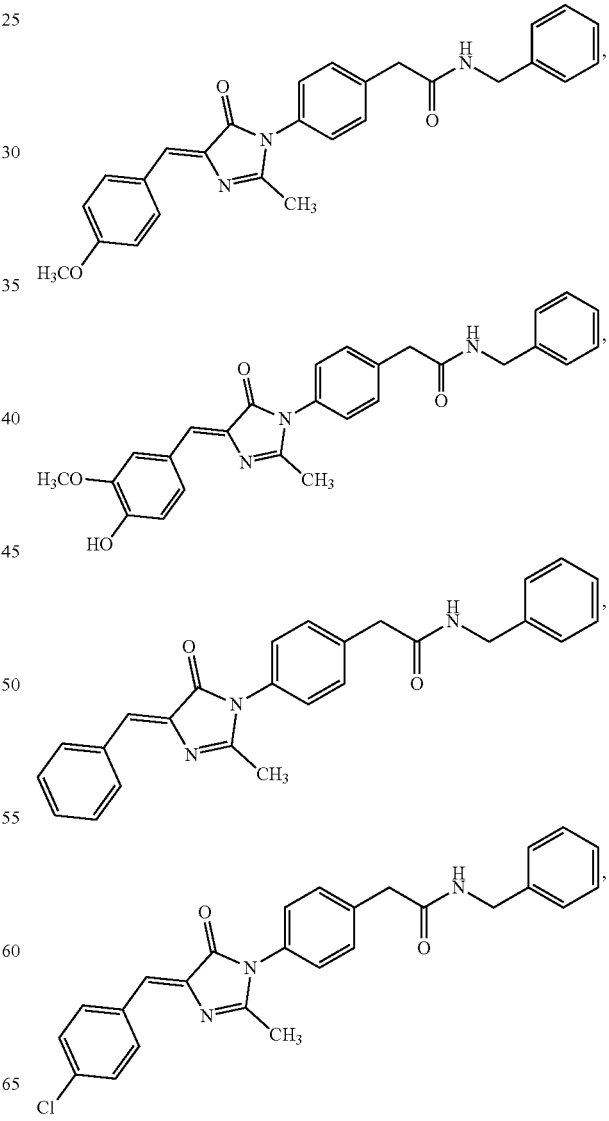

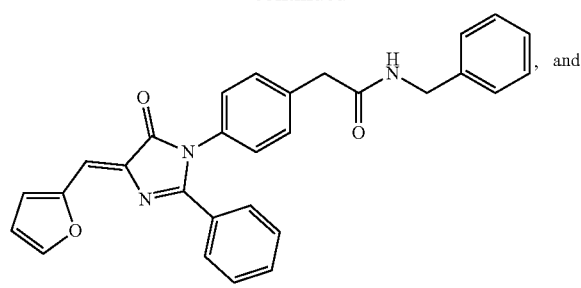

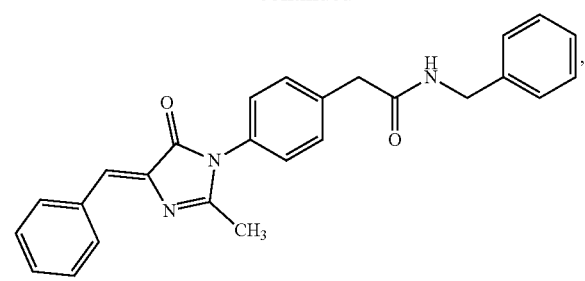

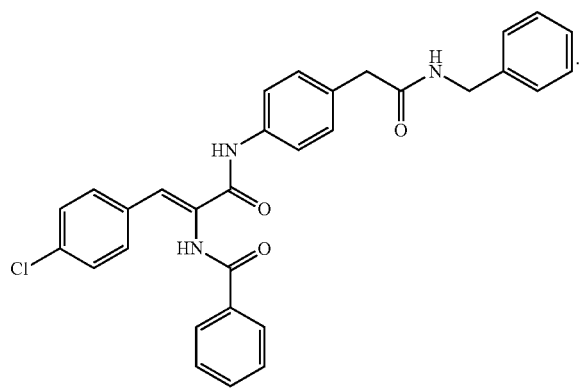 [SMILES: O=C(Cc1ccc(NC(=O)/C(=C/c2ccc(Cl)cc2)NC(=O)c2ccccc2)cc1)NCc1ccccc1]

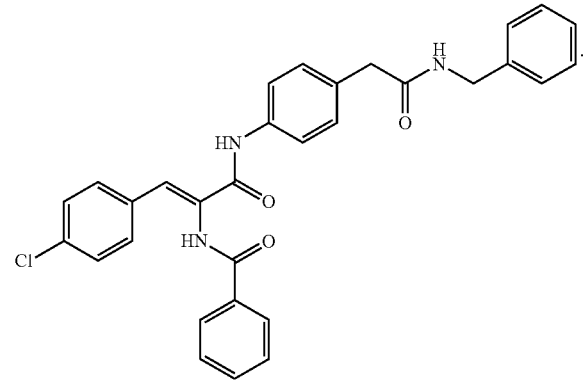 [SMILES: O=C(Cc1ccc(NC(=O)/C(=C/c2ccc(Cl)cc2)NC(=O)c2ccccc2)cc1)NCc1ccccc1]

According to a second aspect, the present disclosure relates to a pharmaceutical composition, comprising the compound of the first aspect and a pharmaceutically acceptable carrier and/or excipient.

In one embodiment, the pharmaceutically acceptable carrier and/or excipient is at least one selected from the group consisting of a buffer, an inorganic salt, a fatty acid, a vegetable oil, a synthetic fatty ester, a surfactant, and a polymer.

In one embodiment, the compound is selected from the group consisting of

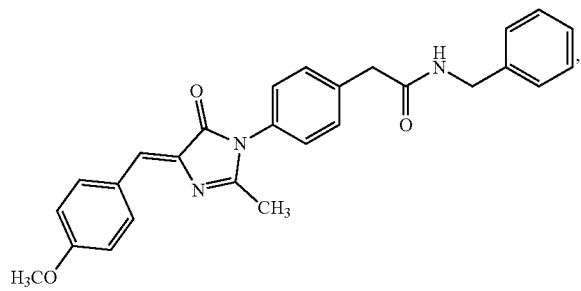

According to a third aspect, the present disclosure relates to a method for treating a proliferative disorder. The method involves administering the pharmaceutical composition of the second aspect to a subject in need of therapy.

In one embodiment, 0.1-500 mg/kg of the compound is administered per body weight of the subject.

In one embodiment, the proliferative disorder is cancer, and the cancer is at least one selected from the group consisting of breast cancer, prostate cancer, and leukemia.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
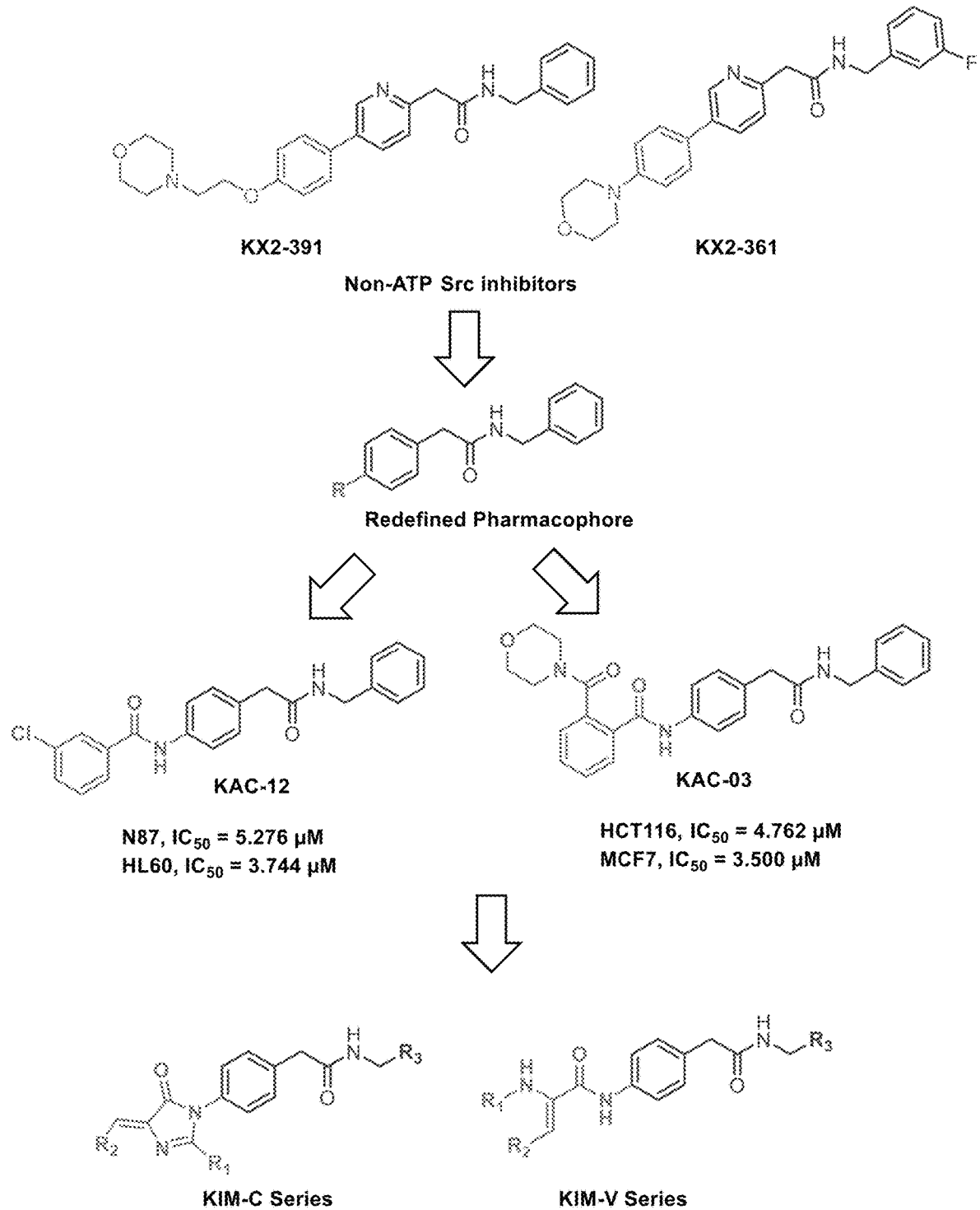
FIG. 1 is a schematic summary of the design of compounds of the present disclosure.
Figure 2:
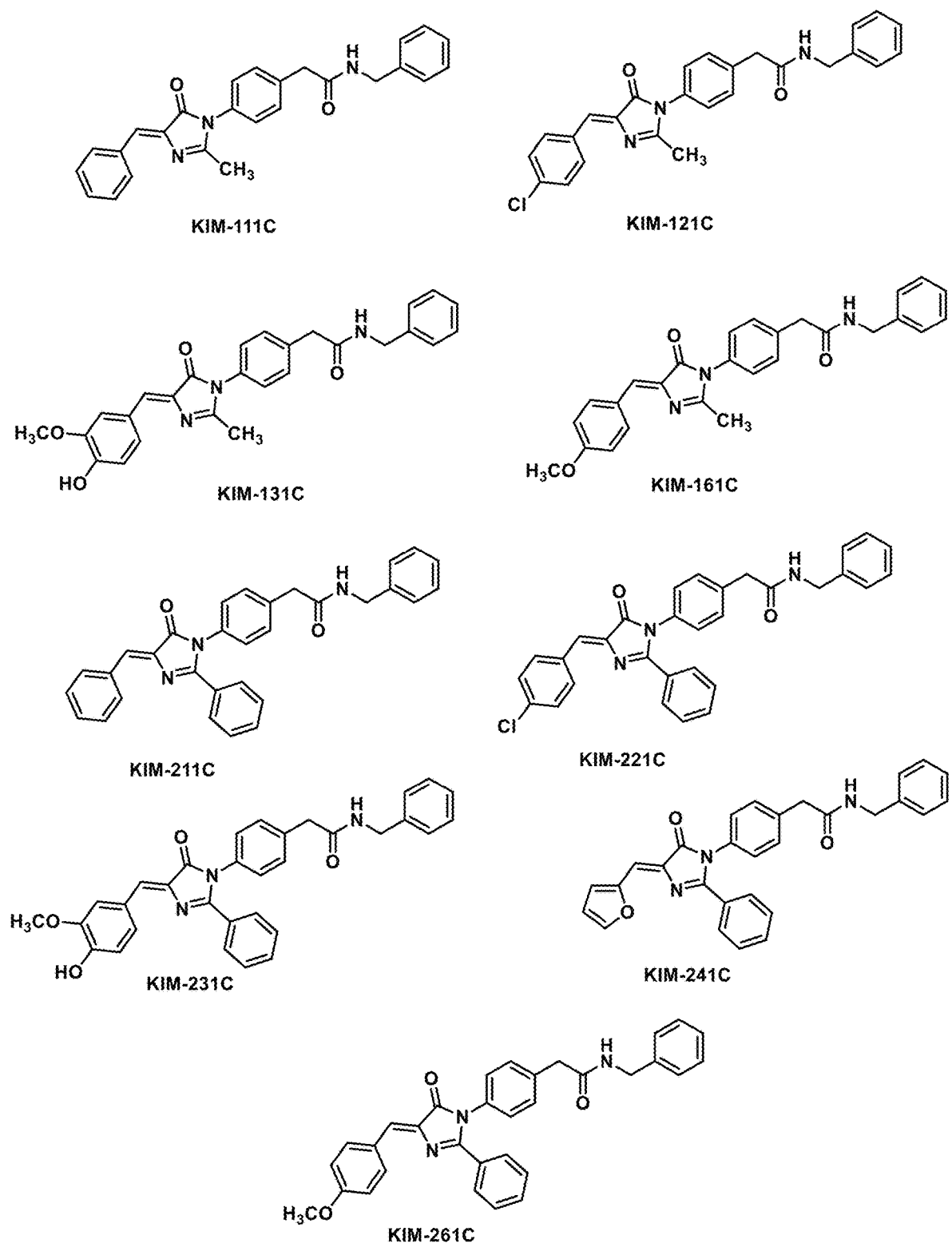
FIG. 2 shows a list of KIM-C compounds.
Figure 3:
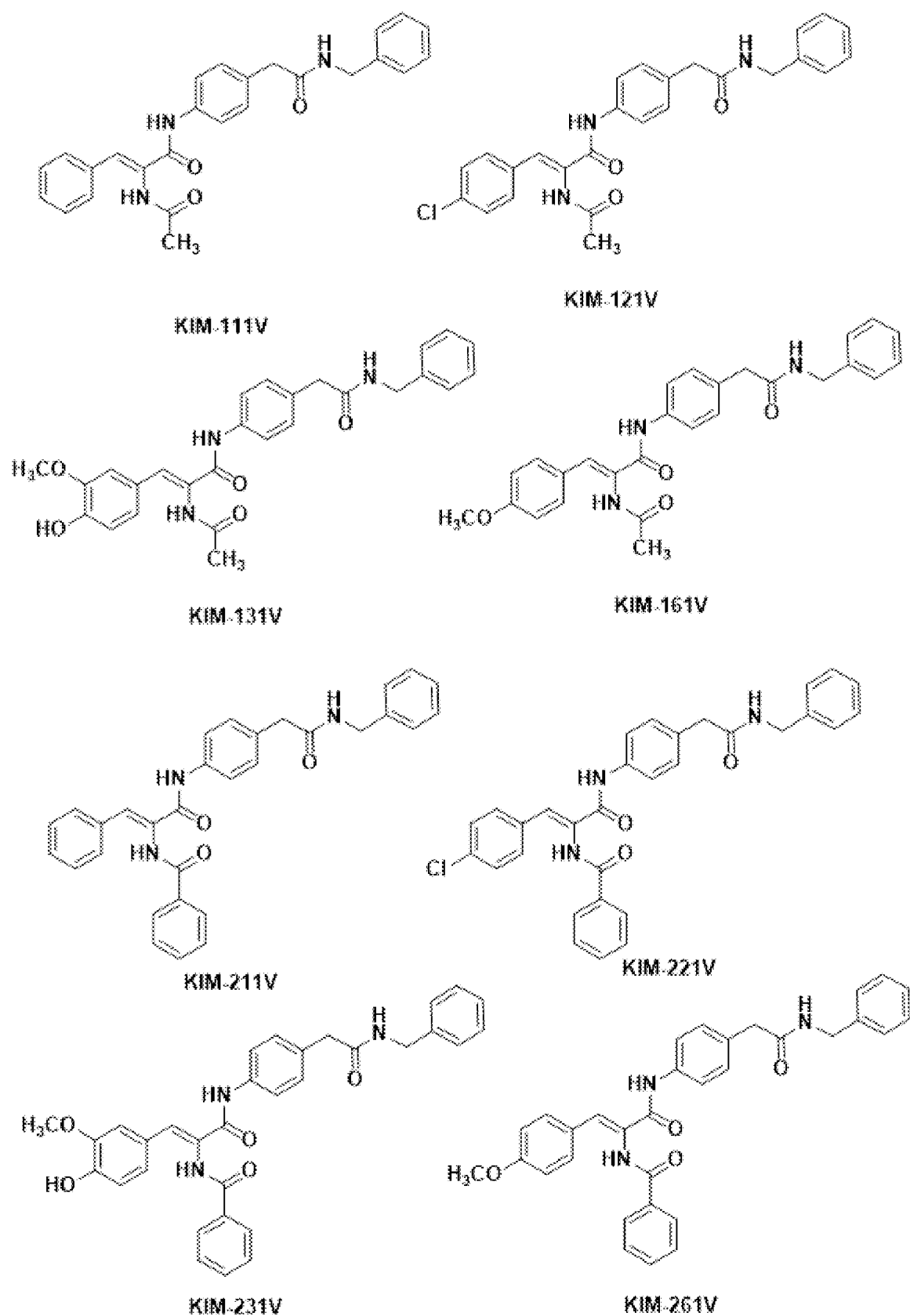
FIG. 3 shows a list of KIM-V compounds.
Figure 3:
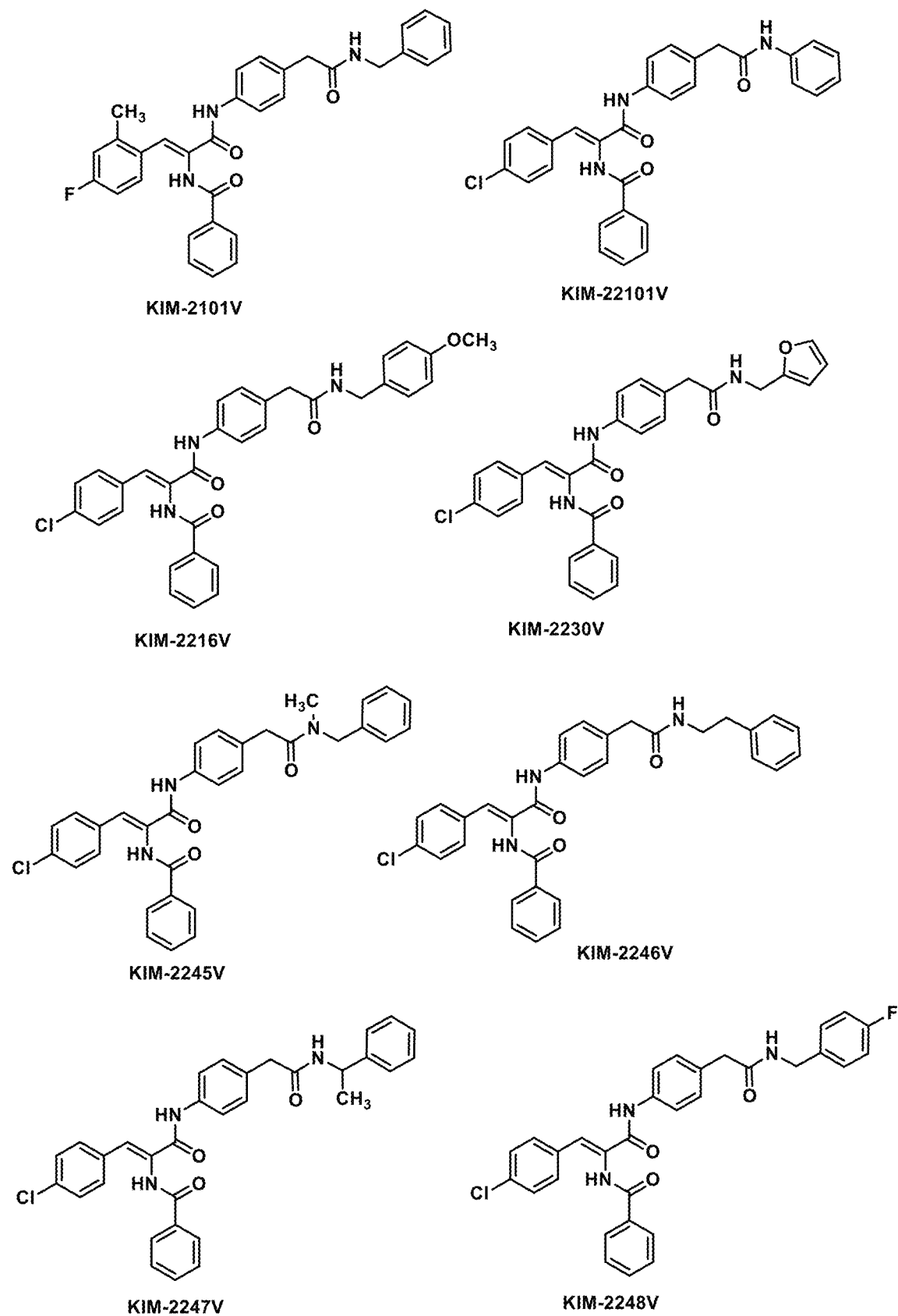
Figure 3:
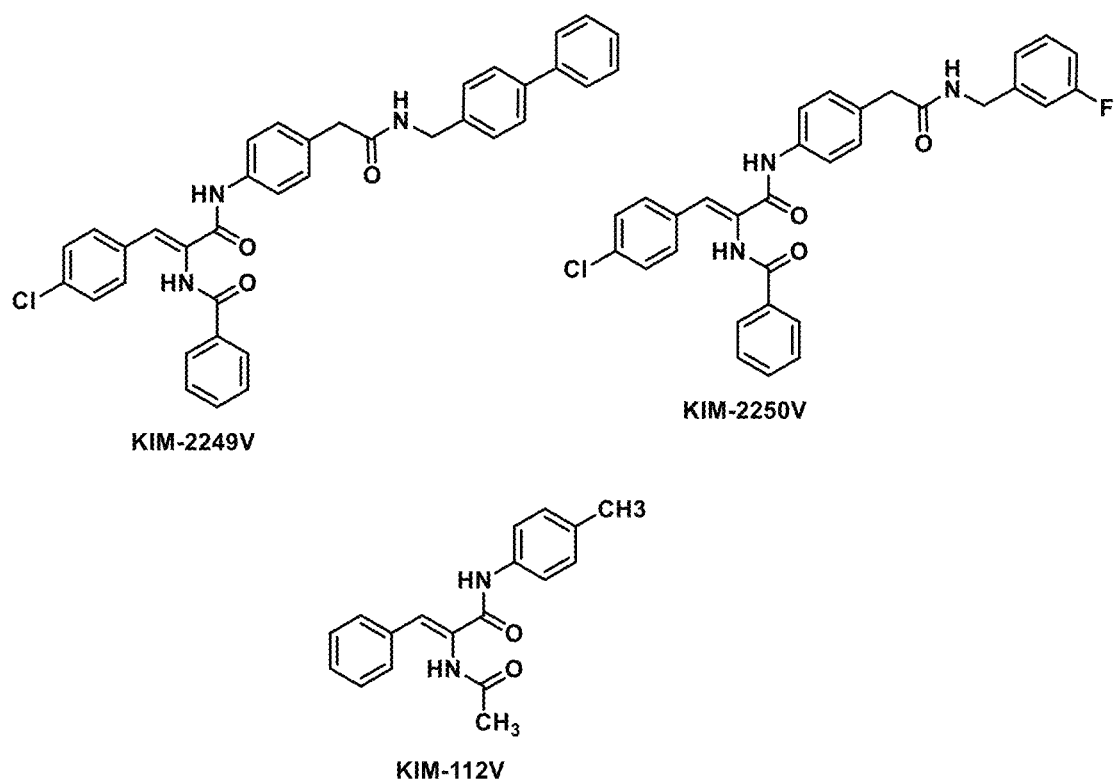

Embodiments of the present disclosure will now be described more fully hereinafter with reference to the accompanying drawings, in which some, but not all embodiments of the disclosure are shown.

As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

As used herein, the terms "compound", "starting material", and "product" are used interchangeably, and are intended to refer to a chemical entity, whether in the solid, liquid or gaseous phase, and whether in a crude mixture or purified and isolated.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, isopropanol, n-butanol, isobutanol, tert-butanol, ethyl acetate and other lower alkanols, glycerine, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g. polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those of ordinary skill in the art.

As used herein, the term "tautomer" refers to constitutional isomers of organic compounds that readily convert by tautomerization or tautomerism. The interconversion commonly results in the formal migration of a hydrogen atom or proton, accompanied by a switch of a single bond and adjacent double bond. Tautomerism is a special case of structural isomerism, and because of the rapid interconversion, tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic tautomerism in heterocyclic rings), and open-chain and cyclic forms of an acetal or hemiacetal (e.g., in reducing sugars).

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection of their order differs. By definition, molecules that are stereoisomers of each other represent the same structural isomer. Enantiomers are two stereoisomers that are related to each other by reflection, they are non-superimposable mirror images.

Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans- (E- and Z-) isomers, and non-enantiomeric optical isomers. Diastereomers seldom have the same physical properties. In terms of the present disclosure, stereoisomers may refer to enantiomers, diastereomers, or both.

Conformers, rotamers, or conformational isomerism refers to a form of isomerism that describes the phenomenon of molecules with the same structural formula but with different shapes due to rotations around one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. In terms of the present disclosure, stereoisomers may refer to conformers, atropisomers, or both.

In terms of the present disclosure, stereoisomers of the double bonds, ring systems, stereogenic centers, and the like can all be present in the compounds, and all such stable isomers are contemplated in the present disclosure. Cis- and trans- (or E- and Z-) stereoisomers of the compounds of the present disclosure wherein rotation around the double bond is restricted, keeping the substituents fixed relative to each other, are described and may be isolated as a mixture of isomers or as separated isomeric forms. S- and R- (or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

As used herein, the term "substituted" refers to at least one hydrogen atom that is replaced with a non-hydrogen group, provided that normal valencies are maintained and that the substitution results in a stable compound. When a substituent is noted as "optionally substituted", the substituents are selected from halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamide (e.g. —SO$_2$NH$_2$), substituted sulfonamide, nitro, cyano, carboxy, unsubstituted amide (i.e. —CONH$_2$), substituted amide (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof. The substituents may themselves be optionally substituted, and may be either unprotected, or protected as necessary, as known to those of ordinary skill in the art, for example, as taught in Greene, et al., "Protective Groups in Organic Synthesis", John Wiley and Sons, Second Edition, 1991, hereby incorporated by reference in its entirety.

As used herein, the term "alkyl" unless otherwise specified refers to both branched and straight chain saturated aliphatic primary, secondary, and/or tertiary hydrocarbons of typically $C_1$ to $C_{21}$, for example $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, and specifically includes, but is not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, 2-propylheptyl, tetradecyl, pentadecyl, hexadecyl, heptadecyl, octadecyl, nonadecyl, and eicosyl.

The term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

The term "arylalkyl", as used herein, refers to a straight or branched chain alkyl moiety having 1 to 8 carbon atoms that is substituted by an aryl group as defined herein, and includes, but is not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

The term "aryl", as used herein, and unless otherwise specified, refers to phenyl, biphenyl, naphthyl, anthracenyl, and the like.

The term "heteroaryl" refers to an aryl group where at least one carbon atom is replaced with a heteroatom (e.g. nitrogen, oxygen, sulfur) and can be indolyl, furanyl, imidazolyl, triazolyl, triazinyl, oxazolyl, isoxazolyl, thiazolyl, isothiazolyl, pyrazolyl, pyrrolyl, pyrazinyl, tetrazolyl, pyridyl (or its N-oxide), thienyl, pyrimidinyl (or its N-oxide), 1H-indolyl, isoquinolyl (or its N-oxide), or quinolyl (or its N-oxide), for example.

The terms "alkoxy" and "alkyloxy" refer to a straight or branched alkyl group attached to an oxygen atom. Exemplary alkyloxy groups include, but are not limited to, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy, and decyloxy.

The term "halogen", as used herein, means fluoro, chloro, bromo and iodo.

The present disclosure is intended to include all isotopes of atoms occurring in the present compounds. Isotopes include those atoms having the same atomic number but different mass numbers. By way of general example, and without limitation, isotopes of hydrogen include deuterium and tritium, isotopes of carbon include $^{13}C$ and $^{14}C$, isotopes of nitrogen include $^{14}N$ and $^{15}N$, and isotopes of oxygen include $^{16}O$, $^{17}O$ and $^{18}O$. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

According to a first aspect, the present disclosure relates to a compound of formula (I),

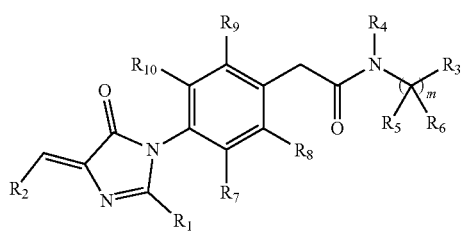

(I)

or a salt thereof, a solvate thereof, a tautomer thereof, or a stereoisomer thereof.

$R_1$ is selected from the group consisting of an optionally substituted alkyl, an optionally substituted cycloalkyl, an optionally substituted arylalkyl, and an optionally substituted aryl.

In one embodiment, $R_1$ is an optionally substituted alkyl. In a preferred embodiment, $R_1$ is an unsubstituted alkyl, preferably a linear alkyl, preferably a linear $C_{1-6}$ alkyl, preferably a linear $C_{2-5}$ alkyl, preferably a linear $C_{3-4}$ alkyl. The carbon counts described herein refers to a number of carbon atoms of the alkyl group of $R_1$ which excludes the carbon atoms of optionally present substituents. Exemplary linear alkyls include, but are not limited to methyl, ethyl, n-propyl, n-butyl, n-pentyl, n-hexyl, n-heptyl, and n-octyl. Alternatively, $R_1$ is a branched alkyl, such as isopropyl, sec-butyl, isobutyl, isobutyl, tert-butyl, isopentyl, neopentyl, and isohexyl. In a most preferred embodiment, $R_1$ is methyl.

In another embodiment, $R_1$ is an optionally substituted aryl, such as an optionally substituted phenyl, and naphthyl. Preferably $R_1$ is an optionally substituted phenyl. The phenyl of $R_1$ may be substituted with at least one substituent such as an alkoxy (e.g. methoxy, ethoxy), an alkyl, a halogen (e.g. chloro), and nitro. In a most preferred embodiment, $R_1$ is phenyl.

$R_2$ is an optionally substituted aryl, or an optionally substituted heteroaryl.

In one embodiment, $R_2$ is an optionally substituted phenyl. The phenyl of $R_2$ may be substituted with at least one substituent such as a hydroxy, an alkoxy (e.g. methoxy, ethoxy), an alkyl (e.g. methyl, ethyl), an amino (e.g. dimethylamino), halogen (e.g. fluoro, chloro, bromo), nitro, and cyano. In a preferred embodiment, $R_2$ is selected from the group consisting of phenyl, p-chlorophenyl, p-hydroxy-m-methoxyphenyl, p-methoxyphenyl. In a most preferred embodiment, $R_2$ is p-methoxyphenyl.

In another embodiment, $R_2$ is an optionally substituted heteroaryl. Exemplary applicable heteroaryls include, but are not limited to, 2-furanyl, 2-thienyl, 3-methyl-2-furanyl, 3-methyl-2-thienyl, 3-methyl-2-pyridinyl, and 4-methyl-2-pyridinyl. In a most preferred embodiment, $R_2$ is 2-furanyl.

$R_3$ is an optionally substituted aryl, or an optionally substituted heteroaryl. In one embodiment, $R_3$ is an optionally substituted aryl, such as optionally substituted phenyl, naphthyl, and biphenyl. In another embodiment, $R_3$ is an optionally substituted heteroaryl, such as 2-furanyl and 2-thienyl. In a preferred embodiment, $R_3$ is selected from the group consisting of phenyl, p-methoxyphenyl, 2-furanyl, p-fluorophenyl, and 4-1,1'-biphenyl. In a most preferred embodiment, $R_3$ is phenyl.

$R_4$ is selected from the group consisting of a hydrogen, an optionally substituted alkyl, an optionally substituted cycloalkyl, an optionally substituted arylalkyl, and an optionally substituted aryl. In one embodiment, $R_4$ is an unsubstituted alkyl, preferably a linear alkyl (e.g. methyl, ethyl, n-propyl). In another embodiment, $R_4$ is a branched alkyl, such as isopropyl, and isobutyl. In a most preferred embodiment, $R_4$ is hydrogen.

$R_5$ and $R_6$ are independently selected from the group consisting of a hydrogen, an optionally substituted alkyl, an optionally substituted cycloalkyl, and an optionally substituted arylalkyl. In one or more embodiments, $R_5$ and $R_6$ are independently a hydrogen or an optionally substituted $C_{1-6}$ alkyl, $C_{2-5}$ alkyl, or a $C_{3-4}$ alkyl. In one embodiment, $R_5$ and $R_6$ are the same. In another embodiment, $R_5$ and $R_6$ are different. In a most preferred embodiment, $R_5$ and $R_6$ are hydrogen.

$R_7$, $R_8$, $R_9$, and $R_{10}$ are independently selected from the group consisting of a hydrogen, an optionally substituted alkyl (e.g. methyl, ethyl), an optionally substituted cycloalkyl, an optionally substituted arylalkyl, a hydroxy, an alkoxy, and a halogen (e.g. chloro, bromo). In a preferred embodiment, $R_7$, $R_8$, $R_9$, and $R_{10}$ are hydrogen.

As used herein, the value of m denotes an alkyl chain of $-CR_5R_6-$ groups connected between $R_3$ and amide group ($-NR_4CO-$) of the compound of formula (I). In one or more embodiments, m is an integer in a range of 1-4, preferably 2-3. Preferably, m is 1 or 2. Most preferably, m is 1.

In some embodiments, the compound represented by formula (I) is one or more of the following structures:

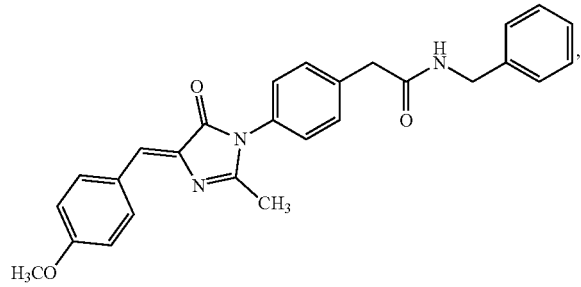

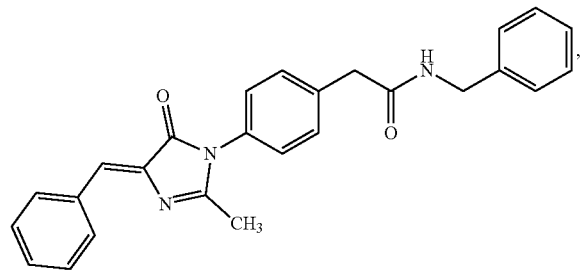

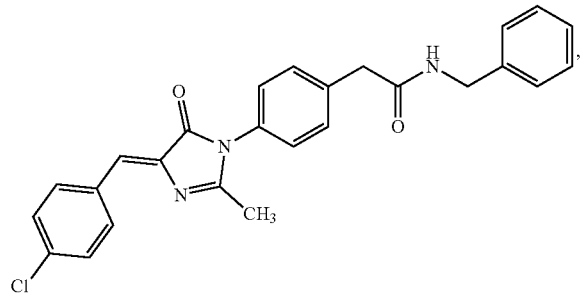

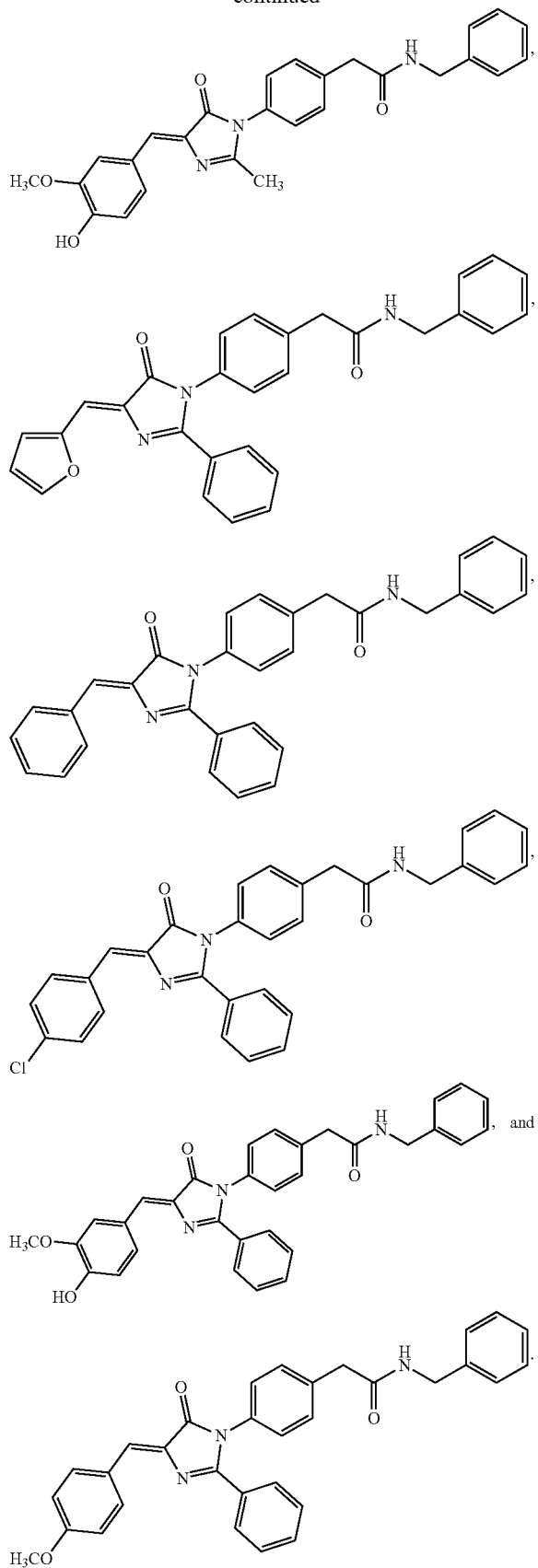

The double bond within the compound of formula (I) may have substituents arranged in cis or trans configuration, preferably the cis configuration. For example, when $R_2$ is p-methoxyphenyl, it is understood that: the compound of formula (I) may be

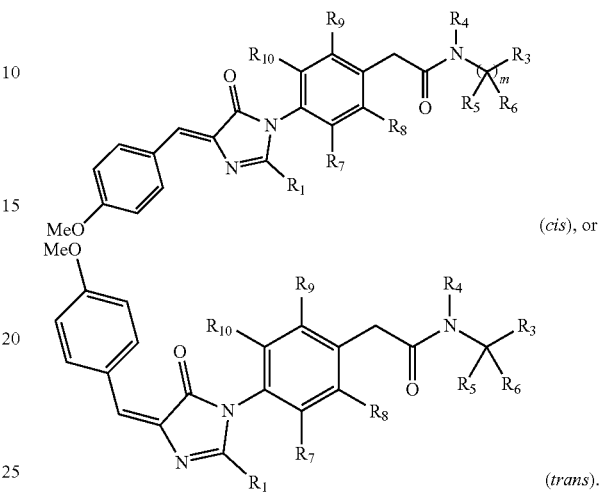

The present disclosure further relates to a compound of formula (II),

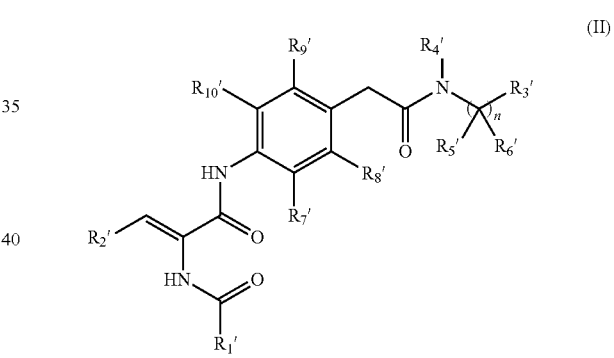

or a salt thereof, a solvate thereof, a tautomer thereof, or a stereoisomer thereof.

$R_1'$ is selected from the group consisting of an optionally substituted alkyl, an optionally substituted cycloalkyl, an optionally substituted arylalkyl, and an optionally substituted aryl.

In one embodiment, $R_1'$ is an optionally substituted alkyl. In a preferred embodiment, $R_1'$ is an unsubstituted alkyl, preferably a linear alkyl, preferably a linear $C_{1-6}$ alkyl, preferably a linear $C_{2-5}$ alkyl, preferably a linear $C_{3-4}$ alkyl. The carbon counts described herein refers to a number of carbon atoms of the alkyl group of $R_1'$ which excludes the carbon atoms of optionally present substituents. Exemplary linear alkyls include, but are not limited to methyl, ethyl, n-propyl, n-butyl, n-pentyl, n-hexyl, n-heptyl, and n-octyl. Alternatively, $R_1'$ is a branched alkyl, such as isopropyl, sec-butyl, isobutyl, isobutyl, tert-butyl, isopentyl, neopentyl, and isohexyl. In a most preferred embodiment, $R_1'$ is methyl.

In another embodiment, $R_1'$ is an optionally substituted aryl, such as an optionally substituted phenyl, and naphthyl. Preferably $R_1'$ is an optionally substituted phenyl. The phenyl of $R_1'$ may be substituted with at least one substituent such as an alkoxy (e.g. methoxy, ethoxy), an alkyl, a halogen (e.g. chloro), and nitro. In a most preferred embodiment, $R_1'$ is phenyl.

$R_2'$ is an optionally substituted aryl, or an optionally substituted heteroaryl.

In one embodiment, $R_2'$ is an optionally substituted phenyl. The phenyl of $R_2'$ may be substituted with at least one substituent such as a hydroxy, an alkoxy (e.g. methoxy, ethoxy), an alkyl (e.g. methyl, ethyl), an amino (e.g. dimethylamino), a halogen (e.g. fluoro, chloro, bromo), nitro, and cyano. In a preferred embodiment, $R_2'$ is selected from the group consisting of phenyl, p-chlorophenyl, p-hydroxy-m-methoxyphenyl, p-methoxyphenyl, and p-fluoro-o-methylphenyl. In another embodiment, $R_2'$ is an optionally substituted heteroaryl. Exemplary applicable heteroaryls include, but are not limited to, 2-furanyl, 2-thienyl, 3-methyl-2-furanyl, 3-methyl-2-thienyl, 3-methyl-2-pyridinyl, and 4-methyl-2-pyridinyl. In a most preferred embodiment, $R_2'$ is p-chlorophenyl.

$R_3'$ is an optionally substituted aryl, or an optionally substituted heteroaryl.

In one embodiment, $R_3'$ is an optionally substituted aryl, such as optionally substituted phenyl, naphthyl, and biphenyl. Preferably, $R_3'$ is a phenyl that is optionally substituted by one or more groups such as an alkyl, an alkoxy (e.g. methoxy, ethoxy), and a halogen (e.g. fluoro, chloro, bromo). In another embodiment, $R_3'$ is an optionally substituted heteroaryl. Exemplary applicable heteroaryls include, but are not limited to, 2-furanyl, 2-thienyl, 3-methyl-2-furanyl, 3-methyl-2-thienyl, 3-methyl-2-pyridinyl, and 4-methyl-2-pyridinyl. In a preferred embodiment, $R_3'$ is selected from the group consisting of phenyl, p-methoxyphenyl, 2-furanyl, p-fluorophenyl, and 4-1,1'-biphenyl. In a most preferred embodiment, $R_3'$ is phenyl.

$R_4'$ is selected from the group consisting of a hydrogen, an optionally substituted alkyl, an optionally substituted cycloalkyl, an optionally substituted arylalkyl, and an optionally substituted aryl. In one embodiment, $R_4'$ is an unsubstituted alkyl, preferably a linear alkyl (e.g. methyl, ethyl, n-propyl). In another embodiment, $R_4'$ is a branched alkyl, such as isopropyl, and isobutyl. In a preferred embodiment, $R_4'$ is hydrogen or methyl. Most preferably, $R_4'$ is hydrogen.

$R_5'$ and $R_6'$ are independently selected from the group consisting of a hydrogen, an optionally substituted alkyl, an optionally substituted cycloalkyl, and an optionally substituted arylalkyl. In one or more embodiments, $R_5'$ and $R_6'$ are independently a hydrogen or an optionally substituted $C_{1-6}$ alkyl, $C_{2-5}$ alkyl, or a $C_{3-4}$ alkyl. In one embodiment, $R_5'$ and $R_6'$ are the same. In another embodiment, $R_5'$ and $R_6'$ are different. In a preferred embodiment, $R_5'$ is hydrogen, and $R_6'$ is hydrogen, or methyl. In a most preferred embodiment, $R_5'$ and $R_6'$ are hydrogen.

$R_7'$, $R_8'$, $R_9'$, and $R_{10}'$ are independently selected from the group consisting of a hydrogen, an optionally substituted alkyl (e.g. methyl, ethyl), an optionally substituted cycloalkyl, an optionally substituted arylalkyl, a hydroxy, an alkoxy, and a halogen (e.g. chloro, bromo). In a preferred embodiment, $R_7'$, $R_8'$, $R_9'$, and $R_{10}'$ are hydrogen.

As used herein, the value of n denotes an alkyl chain of —$CR_5R_6'$— groups connected between $R_3'$ and amide group (—$NR_4'CO$—) of the compound of formula (II). In one or more embodiments, n is an integer in a range of 1-4, preferably 2-3. Preferably, n is 1 or 2. Most preferably, n is 1.

In some embodiments, the compound represented by formula (II) is one or more of the following structures:

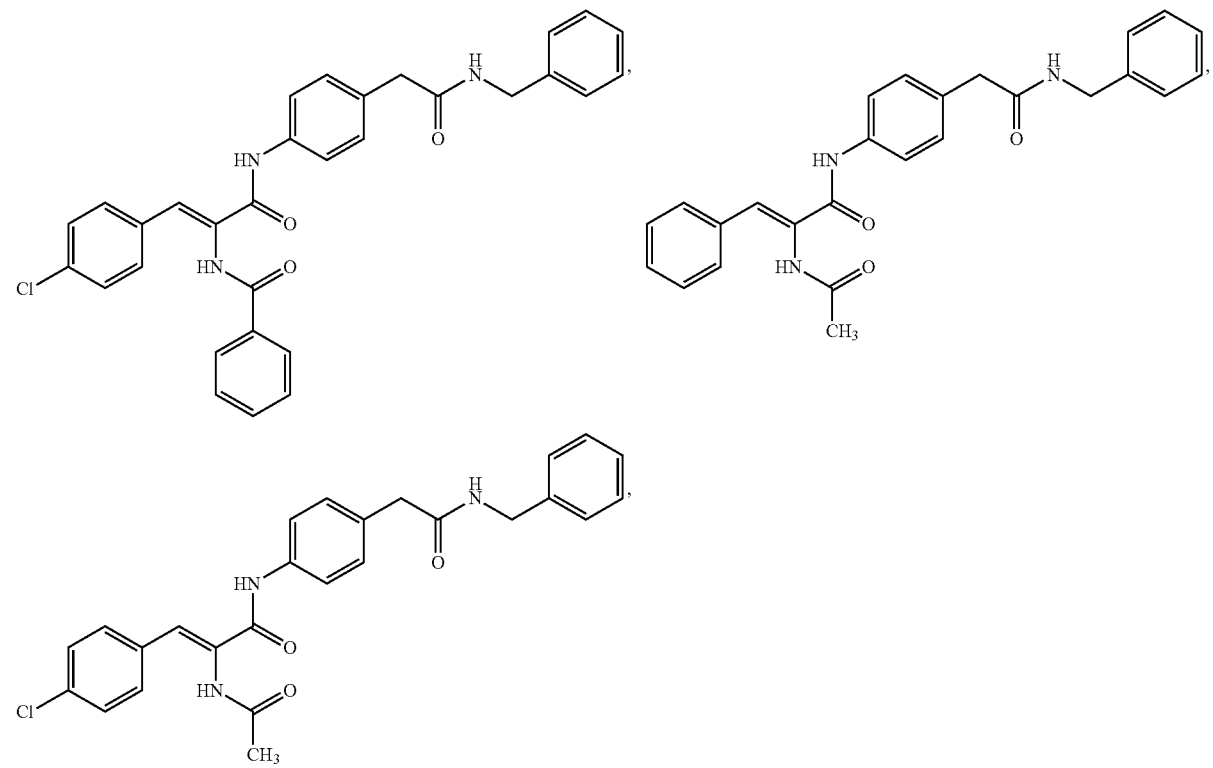

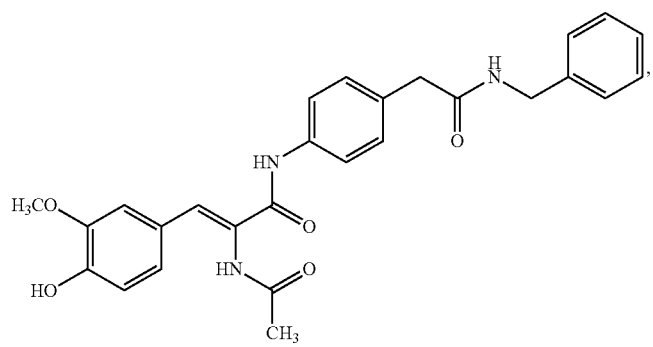
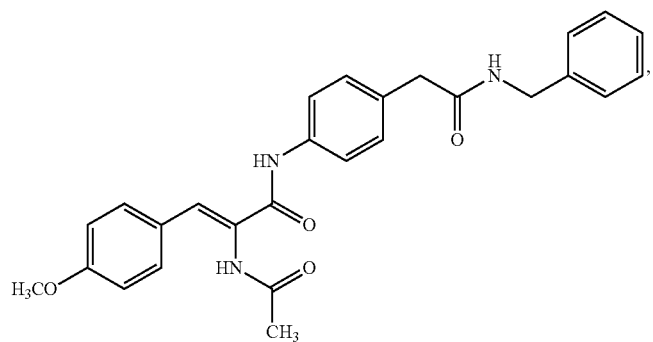
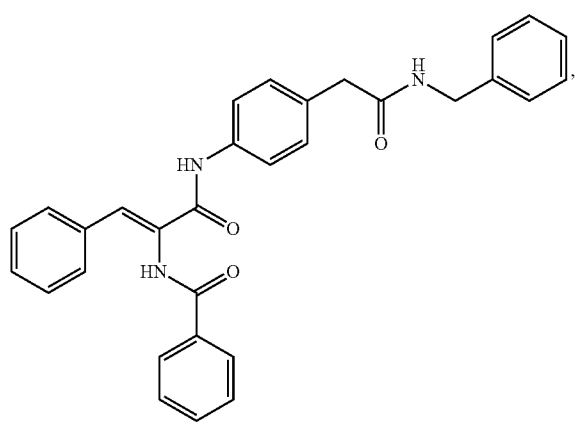
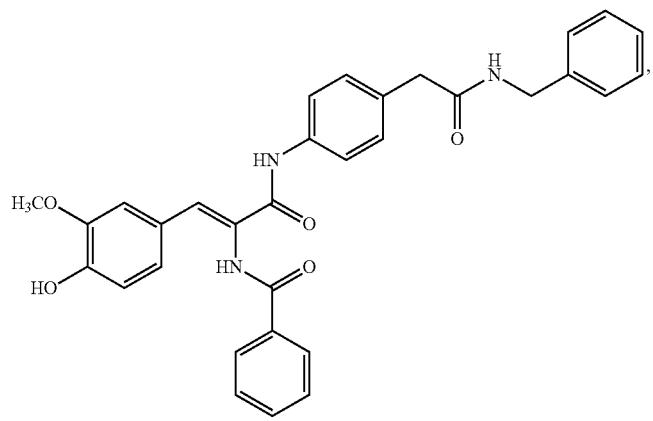

-continued
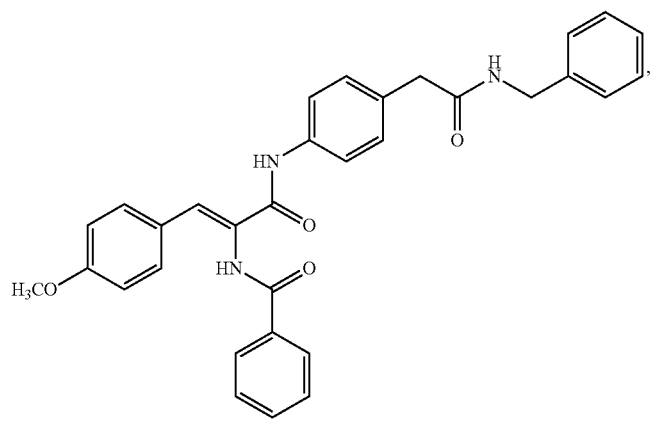
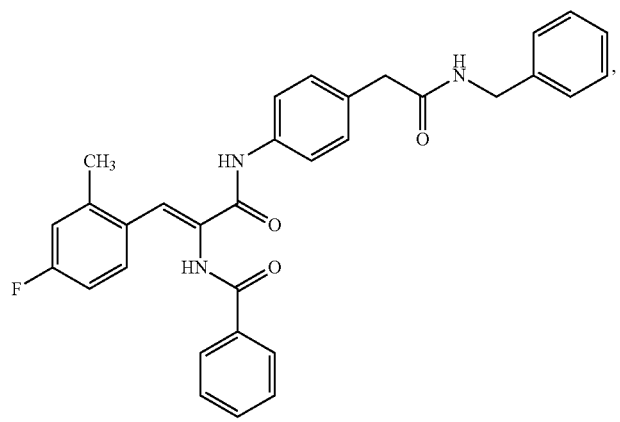
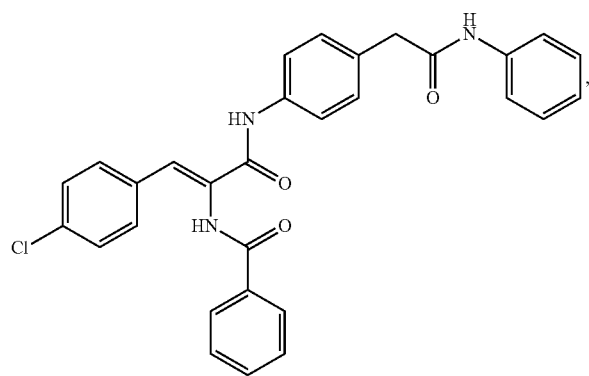
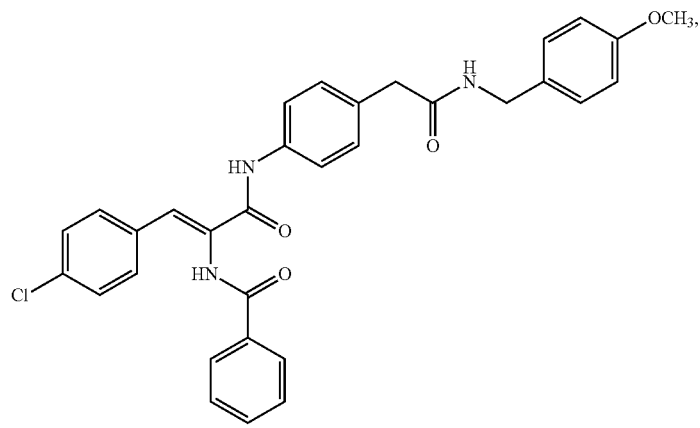

-continued
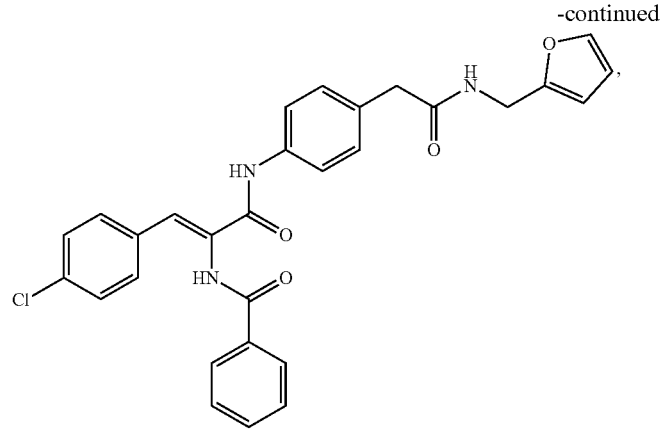
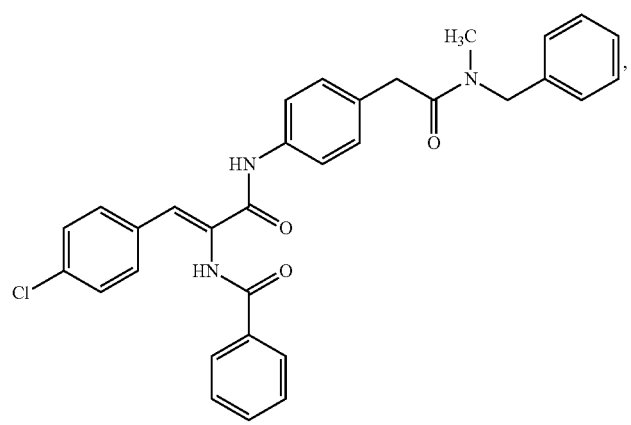
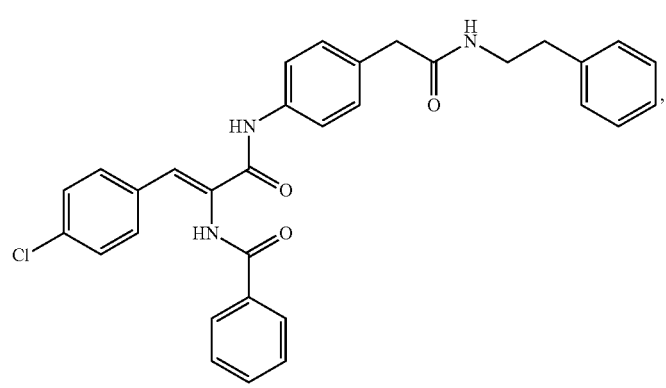
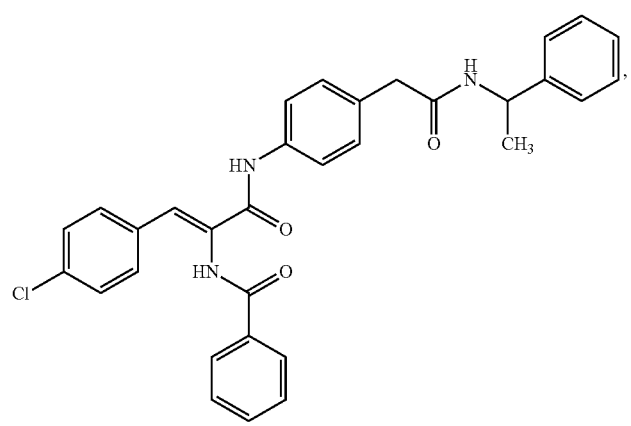

-continued
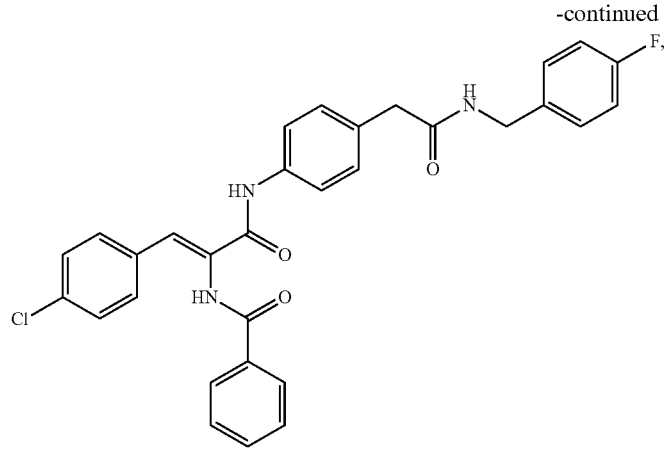
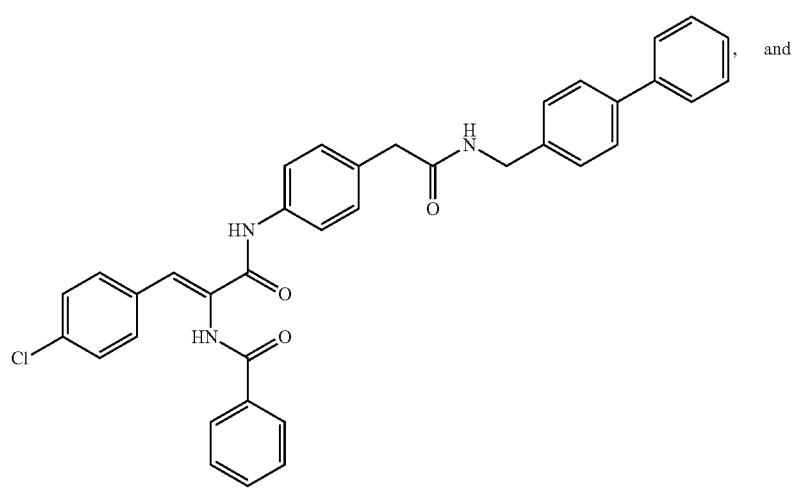, and
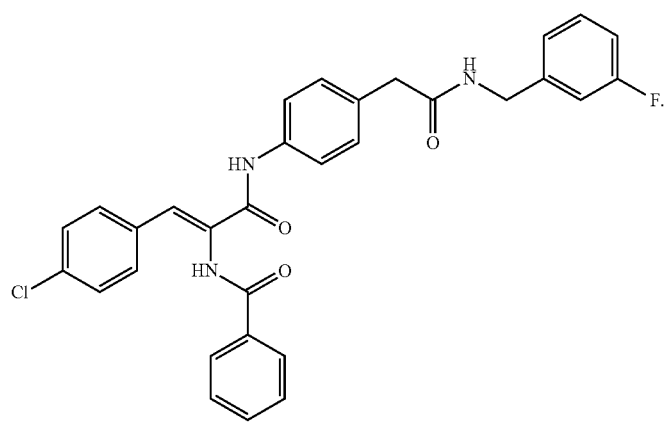 [SMILES: O=C(Cc1ccc(NC(=O)/C(=C/c2ccc(Cl)cc2)NC(=O)c2ccccc2)cc1)NCc1cccc(F)c1]

The double bond within the compound of formula (I) may have substituents arranged in cis or trans conformation, preferably the cis configuration. For example, The double bond within the compound of formula (II) may have substituents arranged in cis or trans configuration, preferably the cis configuration. For example, when $R_2'$ is p-chlorophenyl, it is understood that: the compound of formula (II) may be

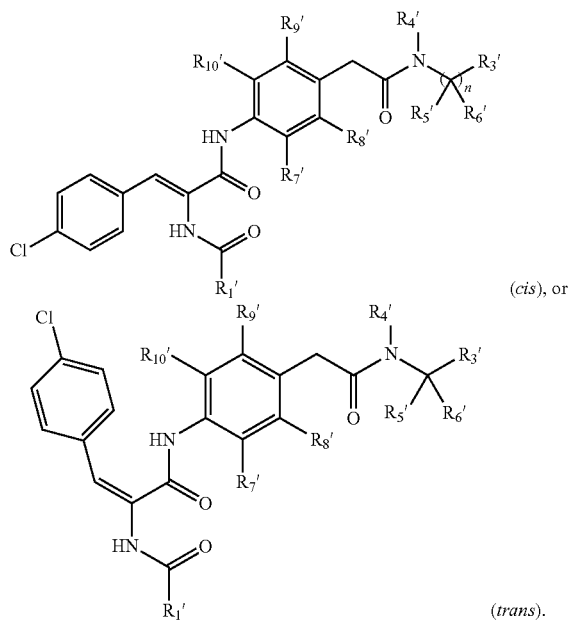

The present disclosure further relates to a compound of formula (III), $$\text{(III)}$$

[structure of formula (III) with $R_9''$, $R_{10}''$, $R_{11}$, $R_8''$, $R_7''$, $R_2''$, $R_1''$]

or a salt thereof, a solvate thereof, a tautomer thereof, or a stereoisomer thereof.

$R_1''$ is selected from the group consisting of an optionally substituted alkyl, an optionally substituted cycloalkyl, an optionally substituted arylalkyl, and an optionally substituted aryl.

In one embodiment, $R_1''$ is an optionally substituted alkyl. In a preferred embodiment, $R_1''$ is an unsubstituted alkyl, preferably a linear alkyl, preferably a linear $C_{1-6}$ alkyl, preferably a linear $C_{2-5}$ alkyl, preferably a linear $C_{3-4}$ alkyl. The carbon counts described herein refers to a number of carbon atoms of the alkyl group of $R_1''$ which excludes the carbon atoms of optionally present substituents. Exemplary linear alkyls include, but are not limited to methyl, ethyl, n-propyl, n-butyl, n-pentyl, n-hexyl, n-heptyl, and n-octyl. Alternatively, $R_1''$ is a branched alkyl, such as isopropyl, sec-butyl, isobutyl, isobutyl, tert-butyl, isopentyl, neopentyl, and isohexyl. In a most preferred embodiment, $R_1''$ is methyl.

In another embodiment, $R_1''$ is an optionally substituted aryl, such as an optionally substituted phenyl, and naphthyl. For example, $R_1''$ is an optionally substituted phenyl. The phenyl of $R_1''$ may be substituted with at least one substituent such as an alkoxy (e.g. methoxy, ethoxy), an alkyl, a halogen (e.g. chloro), and nitro. In a preferred embodiment, $R_1''$ is phenyl.

$R_2''$ is an optionally substituted aryl, or an optionally substituted heteroaryl. In one embodiment, $R_2''$ is an optionally substituted phenyl. The phenyl of $R_2''$ may be optionally substituted with at least one substituent such as a hydroxy, an alkoxy (e.g. methoxy, ethoxy), an alkyl (e.g. methyl, ethyl), an amino (e.g. dimethylamino), a halogen (e.g. fluoro, chloro, bromo), nitro, and cyano. Exemplary $R_2''$ include phenyl, p-chlorophenyl, p-hydroxy-m-methoxyphenyl, p-methoxyphenyl, and p-fluoro-o-methylphenyl. In another embodiment, $R_2''$ is an optionally substituted heteroaryl. Exemplary applicable heteroaryls include, but are not limited to, 2-furanyl, 2-thienyl, 3-methyl-2-furanyl, 3-methyl-2-thienyl, 3-methyl-2-pyridinyl, and 4-methyl-2-pyridinyl. In a most preferred embodiment, $R_2''$ is phenyl.

$R_7''$, $R_8''$, $R_9''$, $R_{10}''$, and $R_{11}$ are independently selected from the group consisting of a hydrogen, an optionally substituted alkyl (e.g. methyl, ethyl, n-propyl), an optionally substituted cycloalkyl, an optionally substituted arylalkyl, a hydroxy, an alkoxy, and a halogen (e.g. chloro, bromo). In a preferred embodiment, $R_7''$, $R_8''$, $R_9''$, and $R_{10}''$ are hydrogen. In another preferred embodiment, $R_{11}$ is methyl.

In one embodiment, the compound represented by formula (III) is

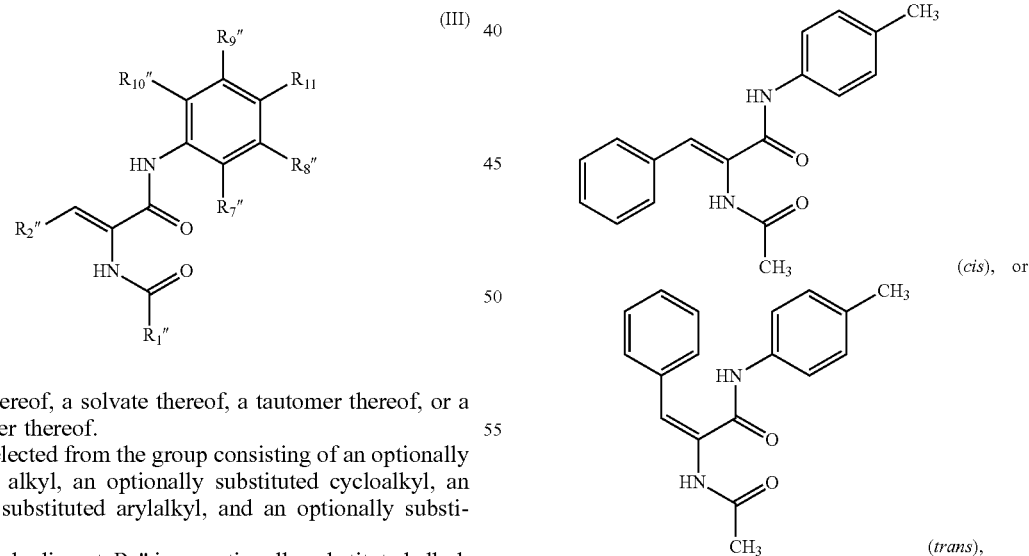

In a preferred embodiment, the compound of formula (III) has cis configuration.

In at least one embodiment, the compound is represented by formula (I), and $R_1$ is methyl, $R_2$ is selected from the group consisting of phenyl, p-chlorophenyl, p-hydroxy-m-methoxyphenyl, and p-methoxyphenyl, preferably p-methoxyphenyl, and $R_3$ is phenyl. In another embodiment, $R_1$ is phenyl, $R_2$ is 2-furanyl, and $R_3$ is phenyl.

In at least one embodiment, the compound is represented by formula (II), and $R_1'$ is phenyl, $R_2'$ is p-chlorophenyl, and $R_3'$ is phenyl.

In a most preferred embodiment, the compound is selected from the group consisting of

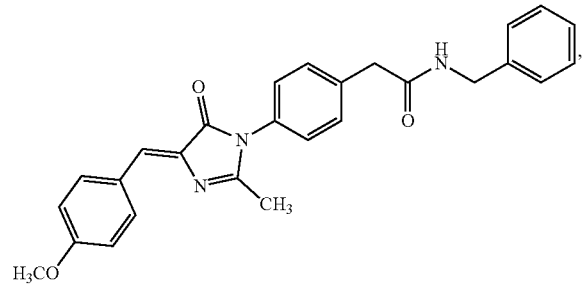

,

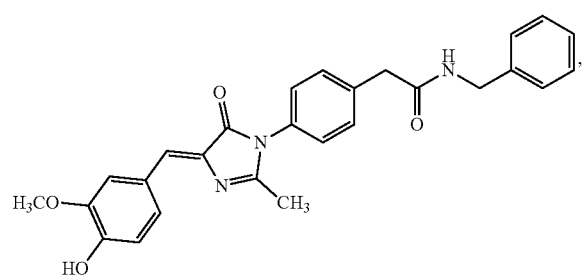

,

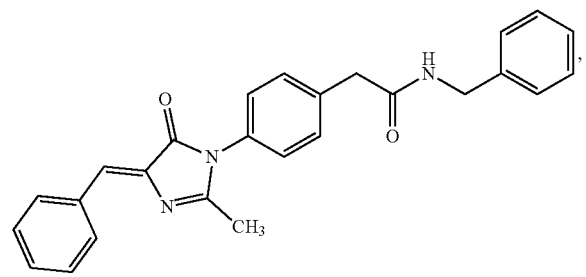

,

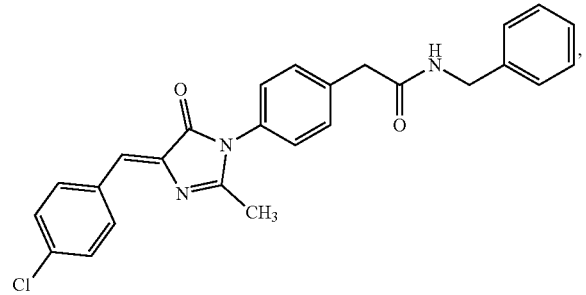

,

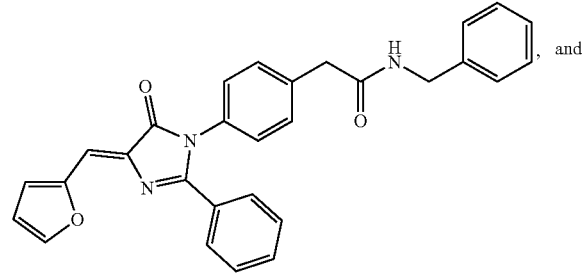

and

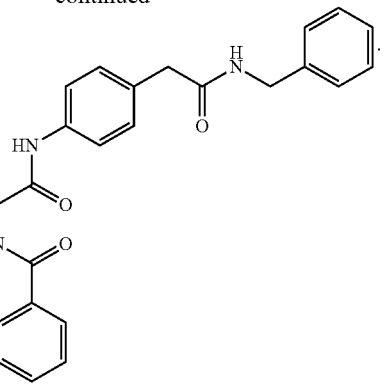

;

The compounds of the present disclosure may be prepared by methods known to those of ordinary skills in the art. The following methods set forth below are provided for illustrative purposes and are not intended to limit the scope of the disclosure.

Figure 5:
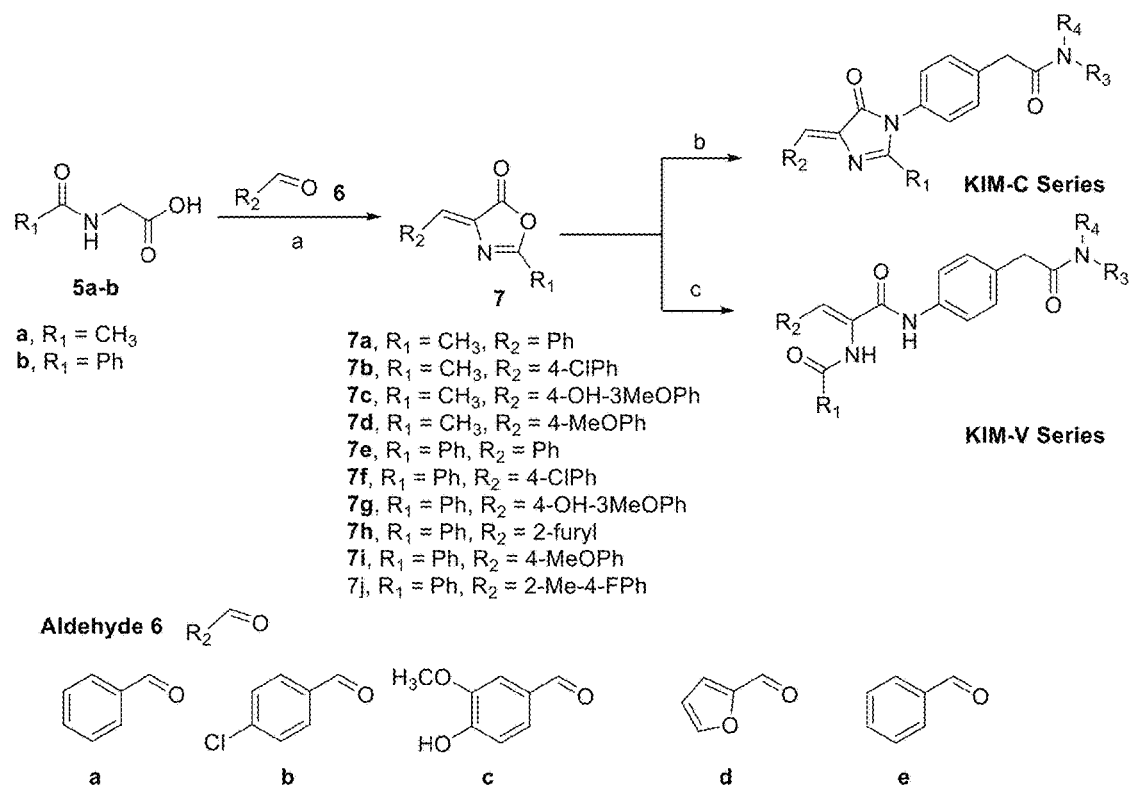
FIG. 5 is a scheme illustrating the synthesis of KIM-C and KIM-V compounds.
Figure 6A:
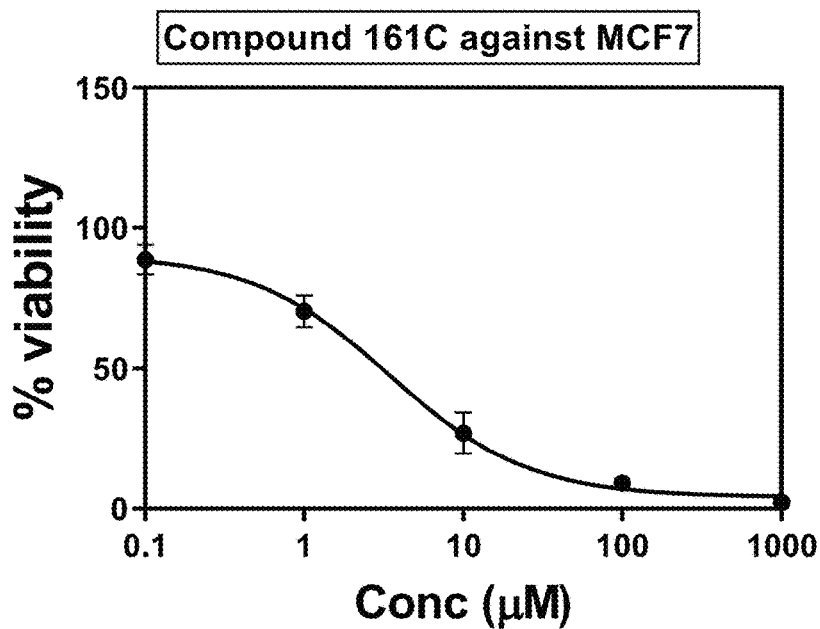
FIG. 6A shows the cytotoxicity of compound KIM-161C against MCF7 breast cancer cells.
Figure 6B:
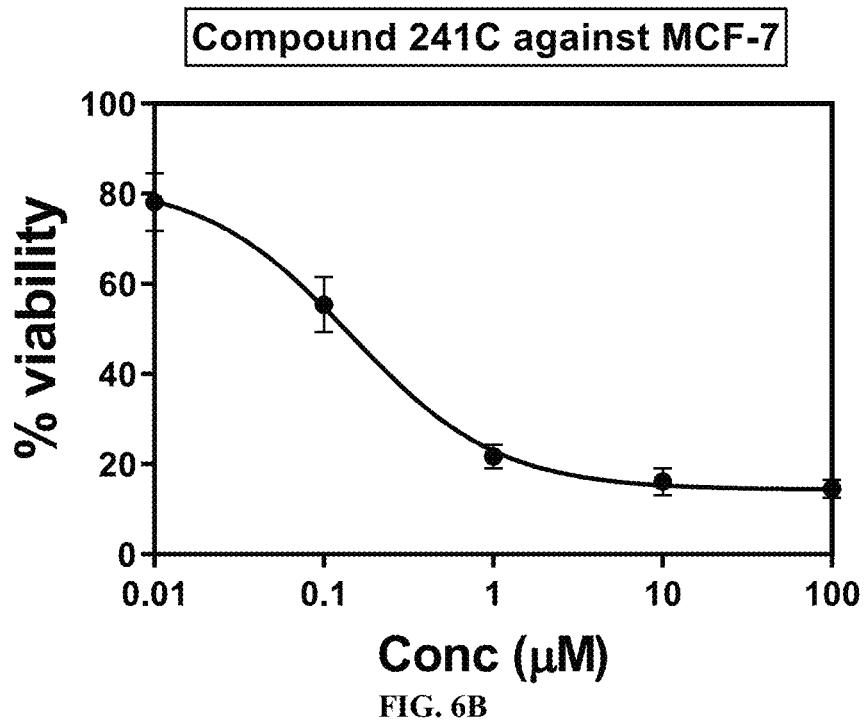
FIG. 6B shows the cytotoxicity of compound KIM-241C against MCF7 breast cancer cells.
Figure 6C:
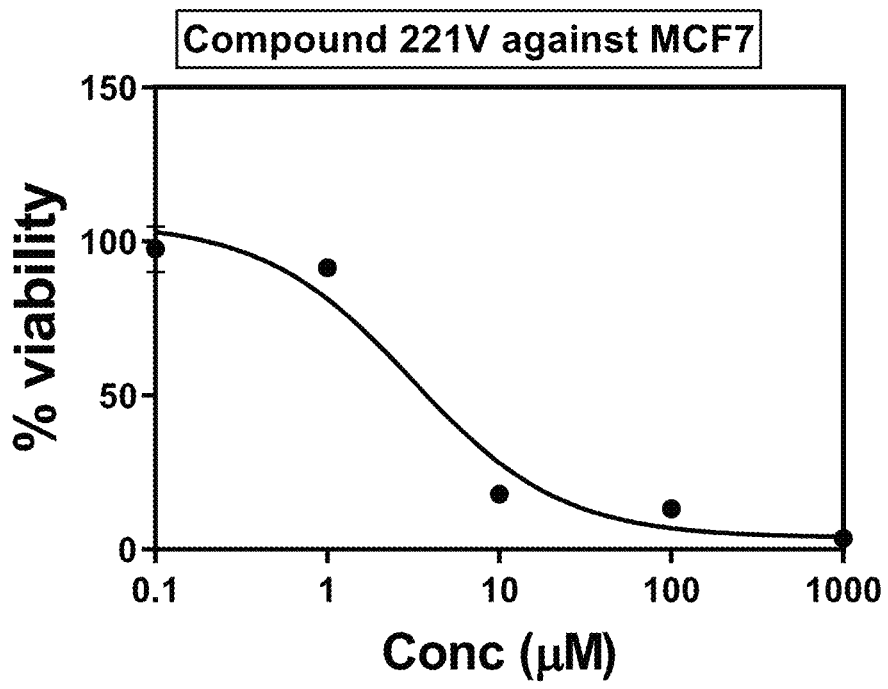
FIG. 6C shows the cytotoxicity of compound KIM-221V against MCF7 breast cancer cells.
Figure 7A:
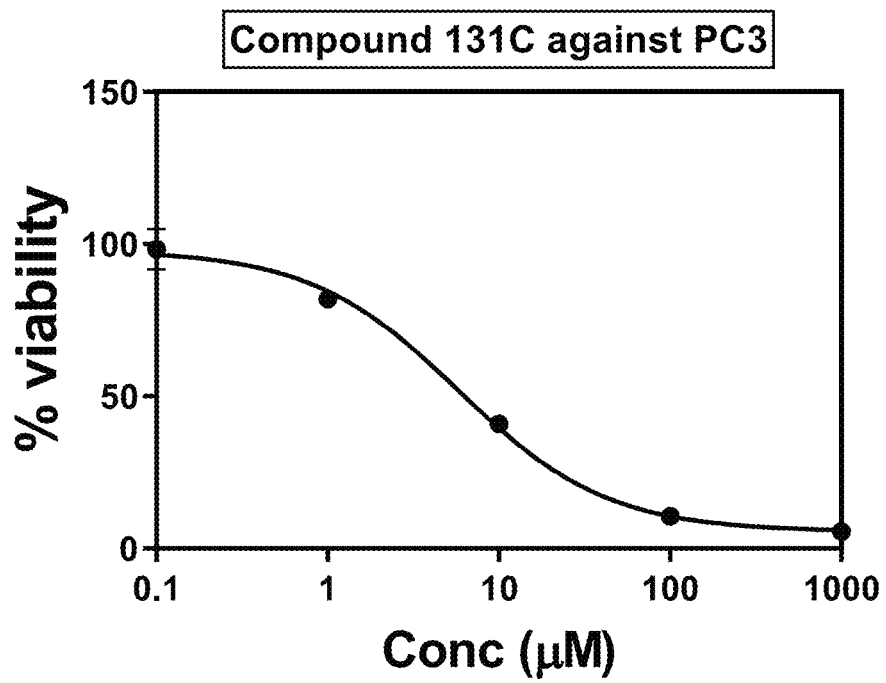
FIG. 7A shows the cytotoxicity of compound KIM-131C against PC3 prostate cancer cells.
Figure 7B:
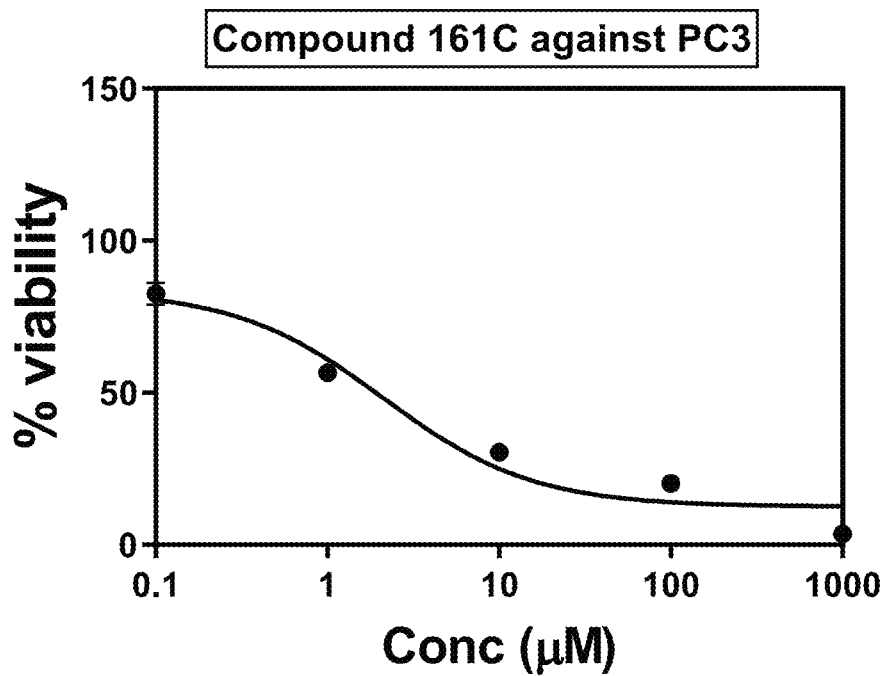
FIG. 7B shows the cytotoxicity of compound KIM-161C against PC3 prostate cancer cells.
Figure 7C:
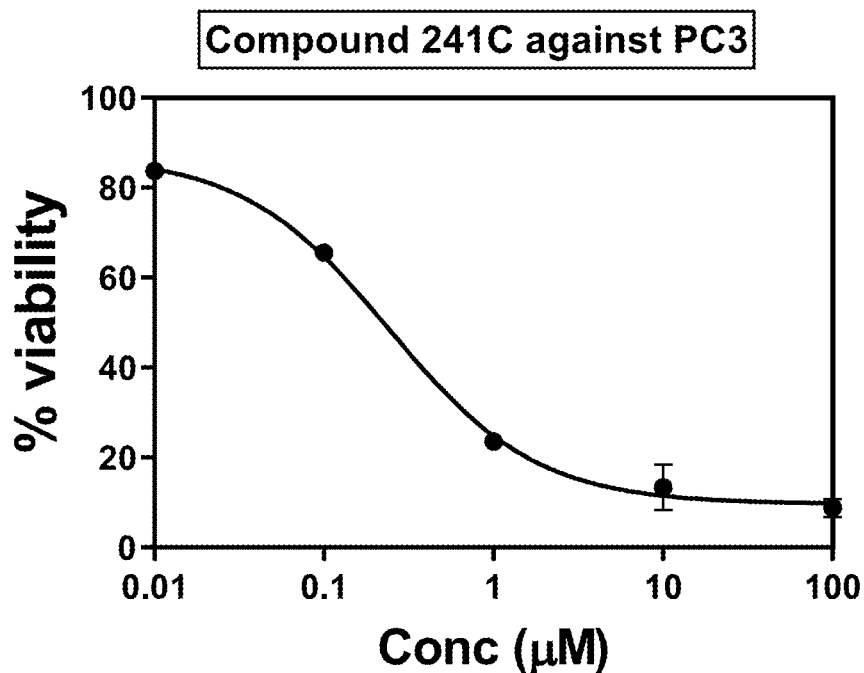
FIG. 7C shows the cytotoxicity of compound KIM-241C against PC3 prostate cancer cells.
Figure 7D:
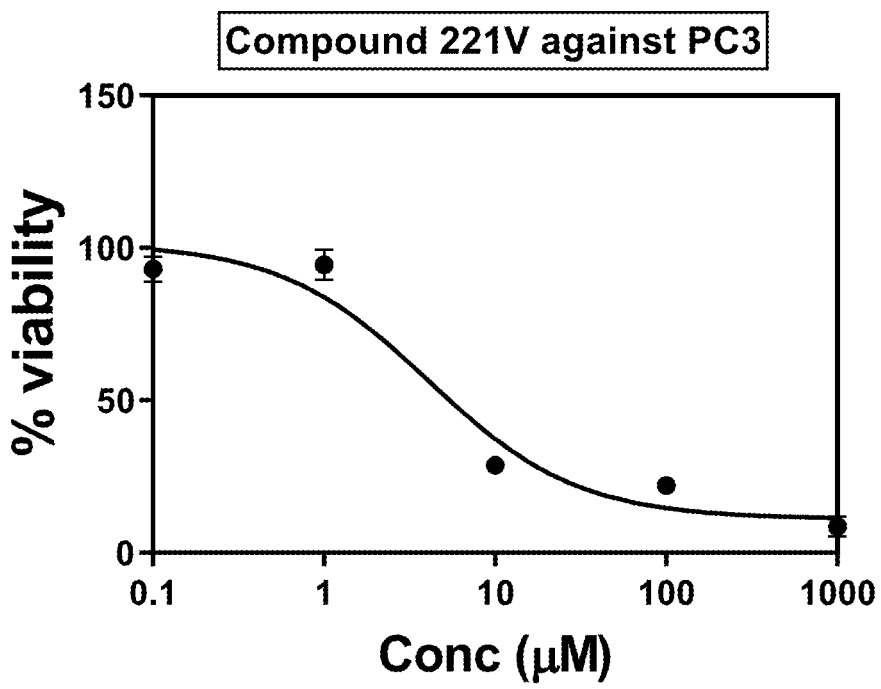
FIG. 7D shows the cytotoxicity of compound KIM-221V against PC3 prostate cancer cells.

The compounds of formula (I) may, for example, be synthesized according to a process illustrated in FIG. 5, route (b) using an aromatic amine of formula (IV)

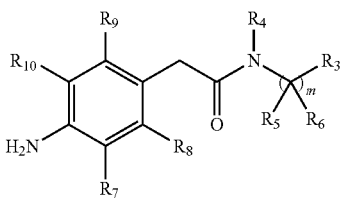

(IV)

or a salt, solvate, tautomer or stereoisomer thereof, and an oxazolone derivative of formula (V)

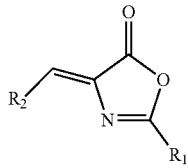

(V)

or a salt, solvate, tautomer or stereoisomer thereof, wherein $R_1$, $R_2$, $R_3$, $R_4$, $R_5$, $R_6$, $R_7$, $R_8$, $R_9$, $R_{10}$ and m are as previously specified.

The aromatic amine of formula (IV) may be formed via (i) a reaction between 2-(4-nitrophenyl)acetic acid with a reagent such as oxalyl chloride, thionyl chloride, phosphorus trichloride ($POCl_3$), and phosphorous pentachloride ($POCl_5$) to form 2-(4-nitrophenyl)acetyl chloride, or via any other activated acyl chemistry known to those of ordinary skill (e.g., anhydride, acyl bromide, etc.); (ii) an amidation reaction between the acyl group of 2-(4-nitrophenyl)acetyl chloride and an amine of formula (VI)

(VI)

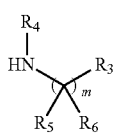

or a salt, solvate, or stereoisomer thereof, in the presence of a base, to form a nitrophenyl amide of formula (VII)

(VII)

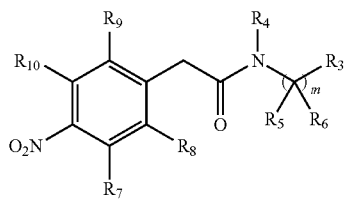

or a salt, solvate, tautomer or stereoisomer thereof, wherein $R_3$, $R_4$, $R_5$, $R_6$, $R_7$, $R_8$, $R_9$, $R_{10}$ and m are as previously specified; (iii) a reduction reaction of the nitrophenyl amide of formula (VII) using a reducing reagent, thereby forming the amine of formula (IV)

(IV)

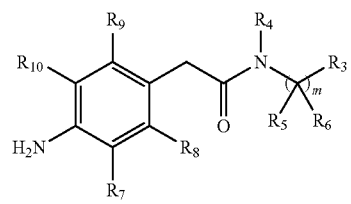

or a salt, solvate, tautomer or stereoisomer thereof.

Reduction methods of nitro groups are generally known to those of ordinary skills in the art. Exemplary reducing methods and/or reagents include, but are not limited to, tin(II) chloride, catalytic hydrogenation over palladium-on-carbon, Raney nickel, sodium sulfide, iron metal in acetic acid, sodium borohydride, lithium borohydride, and Baker's yeast.

The oxazolone derivative of formula (V) may be prepared via Erlenmeyer azlactone synthesis using a carboxylic acid of formula (VIII)

(VIII)

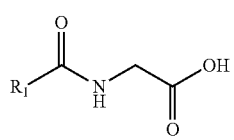

or a salt, solvate, tautomer or stereoisomer thereof, and an aldehyde of formula (IX)

(IX)

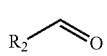

or a salt, solvate, tautomer or stereoisomer thereof, in the presence of a dehydrating agent (e.g. acetic anhydride, carbodiimides such as N,N'-dicyclohexylcarbodiimide), and a base (e.g. sodium acetate), wherein $R_1$ and $R_2$ are as previously specified. In certain embodiments, catalysts may be used to facilitate and/or accelerate the Erlenmeyer synthesis. Exemplary catalysts include, but are not limited to, zinc oxide, alumina, antimony pentafluoride, ruthenium chloride, bismuth acetate, and dodecatungstophosphoric acid.

The Erlenmeyer azlactone synthesis may be performed at a temperature in a range of 30-120° C., 50-100° C., or about 80° C. in neat condition (i.e. solvent free) or in a solvent such as methylene chloride, chloroform, methanol, ethanol, isopropanol, dimethylformamide, tetrahydrofuran, benzene, xylene, ethyl acetate, diethyl ether, acetonitrile, dimethyl sulfoxide, nitrobenzene, and mixtures thereof.

Compounds represented by formula (I) may be obtained by reacting the aforementioned amine of formula (IV) and the oxazolone derivative of formula (V) in the presence of a base (see FIG. 5, route (b)). This reaction may involve an initial ring opening of the oxazolone derivative of formula (V) under basic condition generating a carboxy intermediate, which is followed by an intermolecular cyclization between the carboxy intermediate and the amine of formula (IV), thereby forming the compound of formula (I) with an imidazolinone core. Non-limiting examples of base include pyridine, sodium hydroxide, potassium hydroxide, trimethylamine, triethylamine, diisopropylethylamine (DIPEA), triisopropylamine, dimethylaminopropylamine, N-methylmorpholine, N-methylpyrrolidine, and 4-dimethylaminopyridine (DMAP). In a preferred embodiment, the base is pyridine.

The aforementioned reaction may be performed via heating at a temperature in a range of 50-200° C., 70-150° C., or about 100° C. for 2-24 hours, 4-12 hours, or about 8 hours, preferably in neat condition or in a solvent. In a preferred embodiment, a molar ratio of the amine of formula (IV) to the oxazolone derivative of formula (V) is in a range of 0.7:1 to 2:1, preferably 0.9:1 to 1.5:1, or about 1:1. In another preferred embodiment, a molar ratio of the base (e.g. pyridine) to the oxazolone derivative of formula (V) is in a range of 5:1 to 75:1, preferably 10:1 to 60:1, preferably 25:1 to 40:1, or about 37:1. The reaction forming the compounds of formula (I) may be conducted in inert gas (e.g. nitrogen, argon, helium). Also, in some embodiments, the reaction may not be conducted in inert gas, but in a vacuum.

The compounds of formula (II) may be synthesized according to a process illustrated in FIG. 5, route (c) using an aromatic amine of formula (X)

(X)

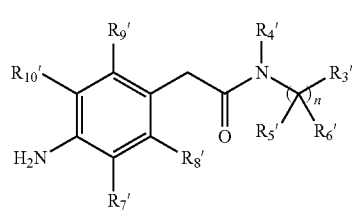

or a salt, solvate, tautomer or stereoisomer thereof, and an oxazolone derivative of formula (XII)

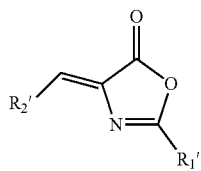

(XI)

or a salt, solvate, tautomer or stereoisomer thereof, wherein $R_1'$, $R_2'$, $R_3'$, $R_4'$, $R_5'$, $R_6'$, $R_7'$, $R_8'$, $R_9'$, $R_{10}'$ and n are as previously specified. The compounds of formula (III) may be synthesized in a similar fashion using an aromatic amine of formula (XII)

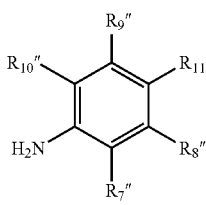

(XII)

or a salt, solvate, tautomer or stereoisomer thereof, and an oxazolone derivative of formula (XIII)

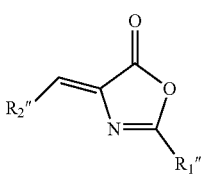

(XIII)

or a salt, solvate, tautomer or stereoisomer thereof, wherein $R_1''$, $R_2''$, $R_7''$, $R_8''$, $R_9''$, $R_{10}''$ and $R_{11}$ are as previously specified. The aromatic amine of formula (X) and the oxazolone derivatives of formulae (XI) and (XIII) used herein may be prepared via above described procedures for compounds of formula (I).

The oxazolone derivatives ((XI), (XIII)) may undergo nucleophilic attack from the amines ((X), (XII)), thereby forming a ring opening product (i.e. compounds of formulae (II) and (III)). The reaction forming the compounds of formulae (II) and (III) may be performed via heating at a temperature in a range of 40-180° C., 60-120° C., or about 80° C. for 2-24 hours, 4-12 hours, or about 8 hours, preferably in a solvent or in neat condition. Exemplary solvent useful for the reaction include acetonitrile, tetrahydrofuran, benzene, xylene, ethyl acetate, methylene chloride, chloroform, dimethylformamide, diethyl ether, dimethyl sulfoxide, nitrobenzene, and mixtures thereof. In a preferred embodiment, the solvent is acetonitrile. The reaction forming the compounds of formulae (II) and (III) may be conducted in inert gas (e.g. nitrogen, argon, helium). Also, in some embodiments, the reaction may not be conducted in inert gas, but in a vacuum.

In at least one embodiment, the above described reaction for the formation of compounds of formulae (II) and (III) does not involve additional base (e.g. pyridine).

A molar ratio of the amine of formula (X) to the oxazolone derivative of formula (XI), may be in a range of 0.7:1 to 2:1, preferably 0.9:1 to 1.5:1, or about 1:1. A molar ratio of the amine of formula (XII) to the oxazolone derivative of formula (XIII) may be in a range of 0.7:1 to 2:1, preferably 0.9:1 to 1.5:1, or about 1:1. In a preferred embodiment, the oxazolone derivative of formula (XI) or (XIII) is present in a concentration of 0.05-1 mol/L, preferably 0.1-0.8 mol/L, more preferably 0.2-0.5 mol/L, or about 0.34 mol/L relative to a total volume of the solvent (e.g. acetonitrile).

Due to steric hindrance, the aforementioned oxazolone derivatives of formulae (V), (XI), and (XIII) prepared using Erlenmeyer chemistry may be predominantly cis isomer. The trans isomer of the oxazolone derivatives can be obtained via methods known to those of ordinary skill in the art. For example, cis to trans isomerization may proceed via heating, and irradiation with UV and/or visible light.

The progress of the reactions may be monitored by methods known to those of ordinary skill in the art, such as thin layer chromatography, gas chromatography, nuclear magnetic resonance, infrared spectroscopy, and high pressure liquid chromatography combined with ultraviolet detection or mass spectroscopy. The compounds of formula (I) may be isolated and purified by methods known to those of ordinary skill in the art, such as crystallization, filtration through a celite containing cartridge, evaporating the reaction mixture to dryness, aqueous work-up, extraction with organic solvents, distillation, column chromatography, and high pressure liquid chromatography (HPLC) on normal phase or reversed phase. Preferred methods include column chromatography and recrystallization.

According to a second aspect, the present disclosure relates to a pharmaceutical composition containing the presently disclosed compound(s) and a pharmaceutically acceptable carrier and/or excipient.

As used herein, a "composition" or a "pharmaceutical composition" refers to a mixture of the active ingredient with other chemical components, such as pharmaceutically acceptable carriers and excipients. One purpose of a composition is to facilitate administration of the compound disclosed herein in any of its embodiments to a subject. Pharmaceutical compositions of the present disclosure may be manufactured by processes well known in the art, e.g., by means of conventional mixing, dissolving, granulating, dragee-making, levigating, emulsifying, encapsulating, entrapping or lyophilizing processes. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The term "active ingredient", as used herein, refers to an ingredient in the composition that is biologically active, for example, a compound represented by formula (I), a salt thereof, a solvate thereof, a tautomer thereof, a stereoisomer thereof, a compound represented by formula (II), a salt thereof, a solvate thereof, a tautomer thereof, a stereoisomer thereof, a compound represented by formula (III), a salt thereof, a solvate thereof, a tautomer thereof, a stereoisomer thereof, or any mixtures of these compounds. In some embodiments, other active ingredients in addition to the compound of the current disclosure may be incorporated into a pharmaceutical composition.

In one or more embodiments, the compound of the pharmaceutical composition is selected from the group consisting of

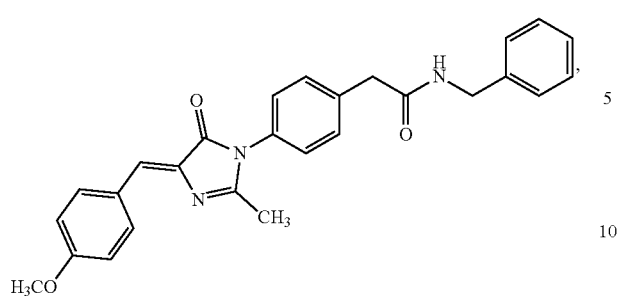

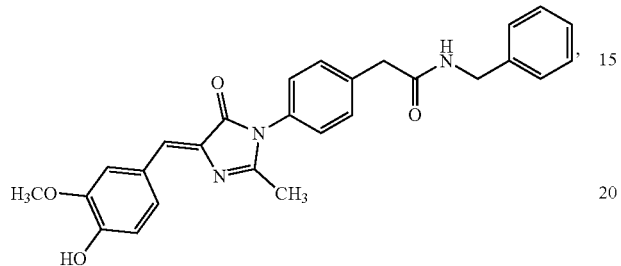

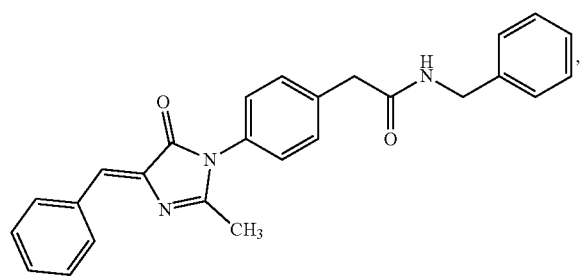

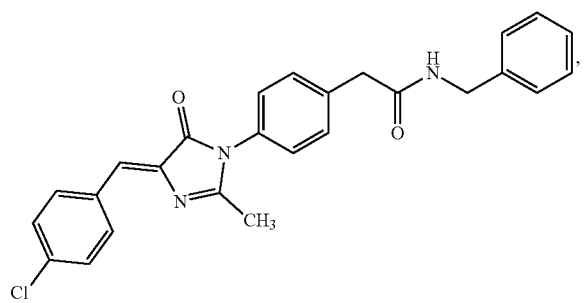

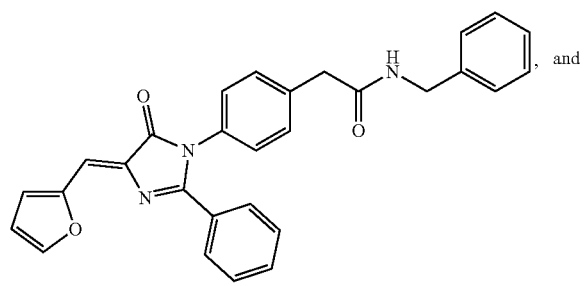, and

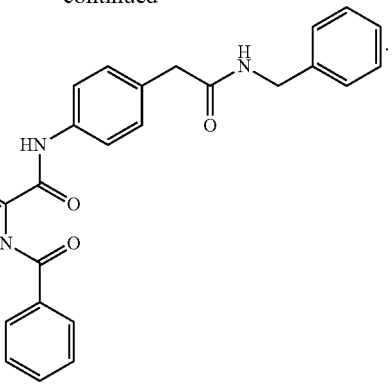

In one embodiment, the pharmaceutical composition comprises 0.1-90 wt % of the compound disclosed herein in any of its embodiments relative to a total weight of the pharmaceutical composition. In preferred embodiments, the pharmaceutical composition comprises at least 0.01 wt %, at least 0.05 wt %, at least 0.1 wt %, at least 0.5 wt %, at least 5 wt %, at least 10 wt %, at least 15 wt %, at least 20 wt %, at least 25 wt %, at least 30 wt %, at least 35 wt %, at least 40 wt %, at least 45 wt %, at least 50 wt %, at least 55 wt %, at least 60 wt %, at least 65 wt %, at least 70 wt %, at least 75 wt %, at least 80 wt %, at least 85 wt %, at least 90 wt %, at least 95 wt %, at least 99 wt %, or at least 99.9 wt % of the compound relative to a total weight of the pharmaceutical composition. The pharmaceutical composition may contain 0.5-500 µM of the compound relative to a total volume of the composition, preferably 1-400 µM, preferably 10-300 µM, preferably 20-200 µM of the compound relative to the total volume of the composition. In some embodiments, the composition comprises up to 0.1 wt %, up to 1 wt %, up to 5 wt %, up to 10 wt %, up to 25 wt %, or up to 50 wt % of a pharmaceutically acceptable salt of the compound. In some embodiments, the composition comprises up to 0.1 wt %, 1 wt %, 5 wt %, or 10 wt % of a pharmaceutically acceptable solvate of the compound. In one or more embodiments, the pharmaceutical composition comprises up to 0.01%, up to 0.1%, up to 1%, up to 5%, or up to 10% by weight of the pharmaceutically acceptable carrier and/or excipient relative to a total weight of the pharmaceutical composition. Preferably, the composition may further comprise pharmaceutically acceptable binders, such as sucrose, lactose, xylitol, and pharmaceutically acceptable excipients such as calcium carbonate, calcium phosphate, and dimethyl sulfoxide (DMSO).

KX-01 and KX-02 developed by Athenex possess intriguing biological mechanisms against cancer cells. In addition to Src inhibition, these two drugs also prevent cancer cell division via interference with tubulin [Tu, C.; Li, J.; Bu, Y.; Hangauer, D.; Qu, J., An ion-current-based, comprehensive and reproducible proteomic strategy for comparative characterization of the cellular responses to novel anti-cancer agents in a prostate cell model. *Journal of proteomics* 2012, 77, 187-201; and Anbalagan, M.; Ali, A.; Jones, R. K.; Marsden, C. G.; Sheng, M.; Carrier, L.; Bu, Y.; Hangauer, D.; Rowan, B. G., Peptidomimetic Src/pretubulin inhibitor KX-01 alone and in combination with paclitaxel suppresses growth, metastasis in human ER/PR/HER2-negative tumor xenografts. Molecular cancer therapeutics 2012, 11 (9), 1936-1947, each incorporated herein by reference in their entirety].

It was found that the biphenylmethylcarboxamide pharmacophore of KX compounds binds to substrate site in Src, but does not enter the juxtaposed ATP pocket. Another mechanism of cytotoxic efficacy of KX compounds involves their inhibition of tubulin. For example, KX2-391 (FIG. 1) is a highly potent anticancer agent for the treatment of several malignant tumors that has passed phase-III clinical trials against actinic keratosis.

Previously, compounds having p-acylamino-N-benzylphenylacetamide pharmacophore were developed as anticancer agents using scaffold hopping design technique (FIG. 1). This pharmacophore demonstrated anti-proliferative activity against cancer cell lines via dual inhibition of Src kinase and tubulin. For example, compounds KAC-03 and KAC-12 exhibited cytotoxic activities against various cancer cell lines (FIG. 1). Further structural modification of this pharmacophore may enhance inhibition of kinases and/or tubulin and provide greater anticancer effect.

In some embodiments, the active ingredient of the current disclosure, e.g. a compound represented by formula (I), a salt thereof, a solvate thereof, a tautomer thereof, a stereoisomer thereof, a compound represented by formula (II), a salt thereof, a solvate thereof, a tautomer thereof, a stereoisomer thereof, a compound represented by formula (III), a salt thereof, a solvate thereof, a tautomer thereof, a stereoisomer thereof, or any mixtures of these compounds, provides utility as an anticancer agent in reducing the viability of cancer cells derived from human cancer cell lines including, but not limited to, breast cancer cell lines (e.g. MCF7, SK-BR-3), prostate cancer cell lines (e.g. PC3), leukemia cell lines (e.g. HL-60), stomach cancer cell lines (e.g. N87, SNU-16), colon cancer cell lines (e.g. HCT-116, HT-29), liver cancer cell lines (e.g. HepG2), lung cancer cell lines (e.g. A549, NCI-H460), brain tumor cell lines (e.g. U251), ovarian cancer cell lines (e.g. NCI-ADR/RES, OVCAR-03), renal cancer cell lines (e.g. 786-0), and melanoma cell lines (e.g. UACC-62).

As used herein, other non-cancerous proliferative disorders that may also be treated by the currently disclosed pharmaceutical composition include, without limitation, atherosclerosis, rheumatoid arthritis, psoriasis, idiopathic pulmonary fibrosis, scleroderma, cirrhosis of the liver, lymphoproliferative disorder, other disorders characterized by epidermal cell proliferation such as verruca (warts), and dermatitis. The active ingredient of the current disclosure may also exhibit other therapeutic activities such as antimicrobial (e.g. antibacterial, antifungal, antiviral, antimycobacterial), antimalarial, pesticidal, antioxidant, as well as anti-inflammatory efficacies.

In some embodiments, the ability of the active ingredient to reduce the viability of cancer cells may be determined by contacting the pharmaceutical composition with the cancer cells and then performing cell viability assays. Methods of such assays include, but are not limited to, ATP test, Calcein AM assay, clonogenic assay, ethidium homodimer assay, Evans blue assay, fluorescein diacetate hydrolysis/Propidium iodide staining assay, flow cytometry, Formazan-based assays (MTT, XTT), green fluorescent protein assay, lactate dehydrogenase (LDH) assay, sulforhodamine B (SRB) assay, methyl violet assay, propidium iodide assay, Resazurin assay, trypan blue assay, and TUNEL assay. In a preferred embodiment, a SRB assay is used. In another preferred embodiment, a Resazurin assay is used.

In some embodiments, the cancer cells are derived from human cancer cell lines, including, but not limited to, breast cancer cell lines, e.g., MDA-MB-231, MCF7, T47D, and VP303, prostate cancer cell lines, e.g., PC3, VCaP, C4-2B, and MDA PCa 2b, leukemia cell lines, e.g., HL-60, CESS, CCRF-CEM, CEM/C1, KASUMI-1, ARH-77, stomach cancer cell lines, e.g., N87, SNU-16, SNU-5, SNU-1, KATO III, AGS, colon cancer cell lines, e.g., HCT15, MDST8, GP5d, HCT116, DLD1, HT29, SW620, SW403 and T84, liver cancer cell lines, e.g. HepG2, PLC/PRF/5, THLE-3, C3A, SNU-182, SNU-398, SNU-387, SNU-423, SNU-475, SNU-449, and Hep 3B2.1-7, lung cancer cell lines, e.g., A549, SHP-77, COR-L23/R, and NCI-H69/LX20, cervical cancer cell Lines, e.g., HeLa DH, HtTA-1, HRS, and C-4I, ovarian cancer cell lines, e.g., A2780, A2780cis, OV7, and PE023, and skin cancer cell lines, e.g., C32TG, A375, and MCC26. In other embodiments, the cancer cells are collected from a human patient who is at risk of having, is suspected of having, has been diagnosed with, or is being monitored for recurrence of at least one type of cancer, preferably breast cancer, prostate cancer, and/or leukemia.

As used herein, the term "cytotoxic effective amount" refers to a concentration of the active ingredient that reduces the viability of the cancer cells by at least 5%, at least 10%, at least 15%, at least 20%, at least 30%, at least 40%, at least 50%, at least 60%, at least 70%, at least 80% or at least 90%, relative to cancer cells not treated with the active ingredient. The reduction in viability may occur no more than 10 days, no more than 7 days, no more than 5 days, no more than 3 days, or no more than 2 days after the active ingredient is contacted with the cancer cells. In one embodiment, the cytotoxic effective amount may be the $IC_{50}$ which is a concentration of the active ingredient which causes the death of 50% of cancer cells in 12-72 hours, 20-48 hours, or about 24 hours (1 day).

In one embodiment, the $IC_{50}$ of the presently disclosed compounds against breast cancer cells (e.g. MCF7) is in a range of 0.1-100 μM, preferably 1-50 μM, more preferably 5-20 μM. In a preferred embodiment, the compound is

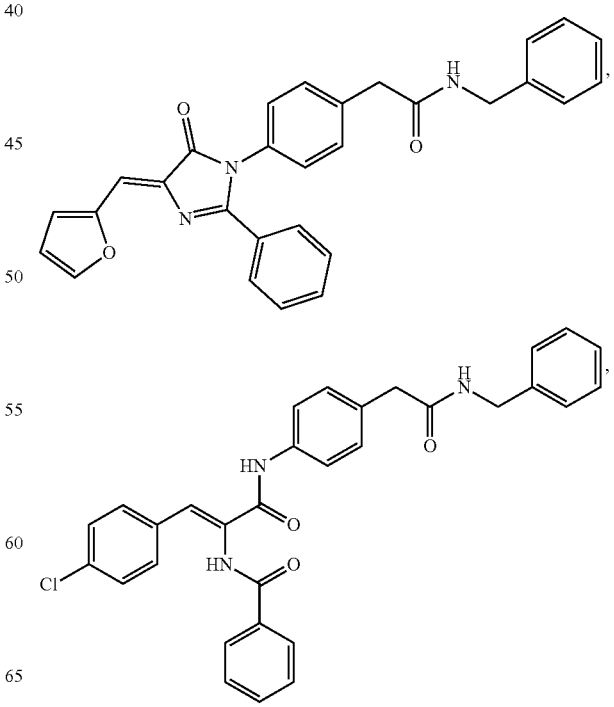

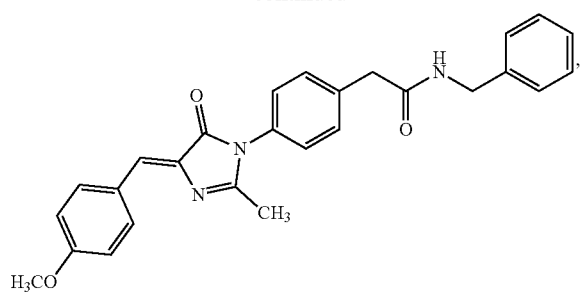

or a mixture thereof, and the $IC_{50}$ against breast cancer cells is in a range of 0.1-5 µM, preferably 0.15-3 µM, more preferably 0.5-1 µM.

In another embodiment, the $IC_{50}$ of the presently disclosed compounds against prostate cancer cells (e.g. PC3) is in a range of 0.2-100 µM, preferably 1-50 µM, more preferably 5-20 µM. In a preferred embodiment, the compound is

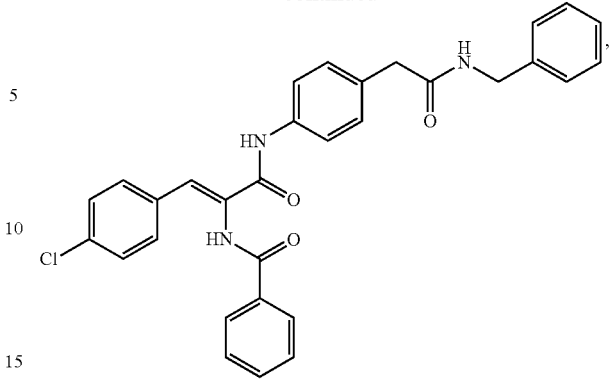

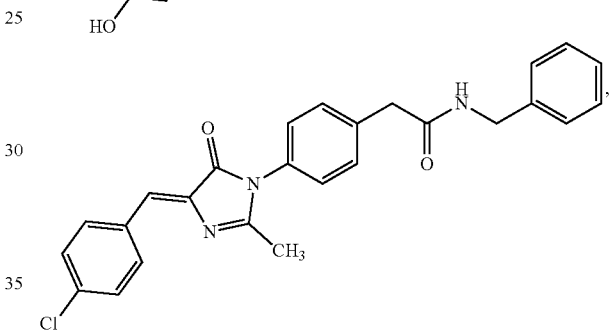

or a mixture thereof, and the $IC_{50}$ against prostate cancer cells is in a range of 0.2-7 µM, preferably 0.3-5 µM, more preferably 0.5-2 µM.

In another embodiment, the $IC_{50}$ of the presently disclosed compounds against leukemia cells is in a range of 100-5,000 nM, preferably 200-1,000 nM, more preferably 400-600 nM. In a preferred embodiment, the compound is

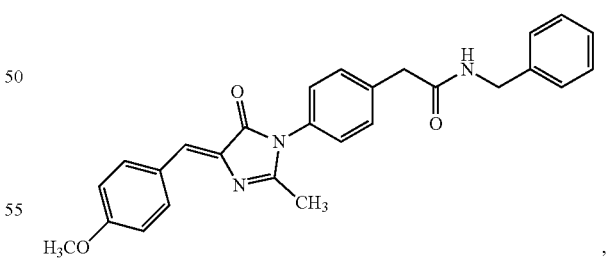

and the $IC_{50}$ against leukemia cells is in a range of 100-400 nM, preferably 200-300 nM, or about 260 nM.

In some embodiments, other active ingredients in addition to the compound(s) of the current disclosure may be incorporated into the pharmaceutical composition. In one embodiment, the pharmaceutical composition includes a second active ingredient that is chemically distinct from the compounds of formulae (I), (II), and (III), such as a chemotherapeutic agent or an anticancer agent, for the treatment or prevention of neoplasm, of tumor or cancer cell division, growth, proliferation and/or metastasis in the subject; induction of death or apoptosis of tumor and/or cancer cells; and/or any other forms of proliferative disorder.

The anticancer agent is at least one of a mitotic inhibitor; an alkylating agent; an antimetabolite; a cell cycle inhibitor; an enzyme; a topoisomerase inhibitor; a biological response modifier; an anti-hormone; a tubulin inhibitor; a tyrosine-kinase inhibitor; an antiangiogenic agent such as MMP-2, MMP-9 and COX-2 inhibitor; an anti-androgen; a platinum coordination complex (oxaliplatin, carboplatin); a substituted urea such as hydroxyurea; a methylhydrazine derivative; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane).

Exemplary anticancer agents include, but are not limited to, tubulin binding agents including paclitaxel, epothilone, docetaxel, discodermolide, etoposide, vinblastine, vincristine, teniposide, vinorelbine, and vindesine; tyrosine-kinase inhibitors including imatinib, nilotinib, dasatinib, bosutinib, ponatinib, and bafetinib; alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; cytotoxic antibiotics including daunorubicin, doxorubicin, idarubicin, mitomycin, actinomycin, epirubicin; topoisomerase inhibitors including irinotecan, mitoxantrone, topotecan, and mixtures thereof.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatin, vegetable oils, and polyethylene glycols.

In one or more embodiments, the pharmaceutically acceptable carrier and/or excipient is at least one selected from the group consisting of a buffer, an inorganic salt, a fatty acid, a vegetable oil, a synthetic fatty ester, a surfactant, and a polymer.

Exemplary buffers include, but are not limited to, phosphate buffers, citrate buffer, acetate buffers, borate buffers, carbonate buffers, bicarbonate buffers, and buffers with other organic acids and salts.

Exemplary inorganic salts include, but are not limited to, calcium carbonate, calcium phosphate, disodium hydrogen phosphate, potassium hydrogen phosphate, sodium chloride, zinc oxide, zinc sulfate, and magnesium trisilicate.

Exemplary fatty acids include, but are not limited to, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, but are not limited to, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethylammonium bromide, tetradecyltrimethylammonium bromide, tetradecyltrimethyl-ammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Depending on the route of administration e.g. oral, parental, or topical, the pharmaceutical composition may be in the form of solid dosage form such as tablets, caplets, capsules, powders, and granules, semi-solid dosage form such as ointments, creams, lotions, gels, pastes, and suppositories, liquid dosage forms such as solutions, and dispersions, inhalation dosage form such as aerosols, and spray, or transdermal dosage form such as patches.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavouring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration may involve the use of transdermal administration such as transdermal patches or iontophoresis devices. Formulation of drugs is discussed in, for example, Hoover, J. E. Remington's pharmaceutical sciences, Mack Publishing Co., Easton, Pa., 1975; and Liberman, H. A.; Lachman, L., Eds. Pharmaceutical dosage forms, Marcel Decker, New York, N.Y., 1980, which are incorporated herein by reference in their entirety.

In other embodiments, the pharmaceutical composition having the presently disclosed compound(s), the salt thereof, the solvate thereof, the tautomer thereof, the stereoisomer thereof, or the mixture thereof has different release rates categorized as immediate release and controlled- or sustained-release.

As used herein, immediate release refers to the release of an active ingredient substantially immediately upon administration. In another embodiment, immediate release occurs when there is dissolution of an active ingredient within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release, or sustained-release, refers to a release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In one embodiment, the pharmaceutical composition described herein is not a controlled-release composition.

According to a third aspect, the present disclosure relates to a method for treating a proliferative disorder. The method involves administering the pharmaceutical composition of the second aspect to a subject in need of therapy.

In one or more embodiments, the proliferative disorder is cancer. In some embodiments, the disclosed method of the current aspect is for treating cancer of the blood, stomach, breast, colon, brain, bladder, lung, cervix, ovary, rectum, pancreas, skin, prostate gland, spleen, liver, kidney, head, neck, testicle, bone, bone marrow, thyroid gland, or central nervous system. In a preferred embodiment, the cancer is at least one selected from the group consisting of breast cancer, prostate cancer, and leukemia.

As used herein, the terms "treat", "treatment", and "treating" in the context of the administration of a therapy to a subject in need thereof refer to the reduction or inhibition of the progression and/or duration of a disease (e.g. cancer), the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumor size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

The term "subject" and "patient" are used interchangeably. As used herein, they refer to any subject for whom or which therapy, including with the compositions according to the present disclosure is desired. In most embodiments, the subject is a mammal, including but not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human.

As used herein, a subject in need of therapy includes a subject already with the disease, a subject which does not yet experience or exhibit symptoms of the disease, and a subject predisposed to the disease. In preferred embodiments, the subject is a person who is predisposed to cancer, e.g. a person with a family history of cancer. Women who have (i) certain inherited genes (e.g. mutated BRCA1 and/or mutated BRCA2), (ii) been taking estrogen alone (without progesterone) after menopause for many years (at least 5, at least 7, or at least 10), and/or (iii) been taking fertility drug clomiphene citrate, are at a higher risk of contracting breast cancer. People who (i) have certain inherited mutated genes (e.g. mutated RNASEL, mutated BRCA1 and/or mutated BRCA2), (ii) had inflammation in the prostate, and/or (iii) are obese are at a higher risk of contracting prostate cancer. People who (i) had chemotherapy and radiation therapy for other cancers, (ii) has genetic disorders, such as Down syndrome, and/or (iii) exposure to certain chemicals, such as benzene are at a higher risk of contracting leukemia.

In another embodiment, the subject refers to a cancer patient who has been previously treated and/or administered with a tyrosine-kinase inhibitor such as imatinib, nilotinib, dasatinib, bosutinib, ponatinib, and bafetinib, and developed drug resistance via (i) Bcr-Abl dependent mechanisms involving Bcr-Abl duplication, Bcr-Abl mutation, T315I mutation, and/or P-loop mutations, or (ii) Bcr-Abl Independent mechanisms involving drug efflux caused by P-glycoproteins, drug import by organic cation transporter 1, and/or alternative signaling pathway activation.

In another embodiment, the subject refers to a cancer patient who has been previously administered and/or treated with a tubulin binding drug such as paclitaxel, epothilone, docetaxel, discodermolide, etoposide, vinblastine, vincristine, teniposide, vinorelbine, and vindesine, and developed resistance to the tubulin binding drug.

In at least one embodiment, the subject has leukemia, prostate, and/or breast cancer and is currently undergoing, or has completed a tyrosine-kinase inhibitor based and/or tubulin inhibitor based chemotherapy regimen.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), topical and rectal administration. Those of ordinary skill in the art are familiar with administration techniques that can be employed with the complexes and methods described herein. In a preferred embodiment, the active ingredient and/or the pharmaceutical composition described herein are administered orally.

In one embodiment, the pharmaceutical composition administered comprises the compound of formula (I), or a salt thereof, a solvate thereof, a tautomer thereof, or a stereoisomer thereof, in which $R_1$ is methyl, or phenyl, $R_2$ is selected from the group consisting of phenyl, p-chlorophenyl, p-hydroxy-m-methoxyphenyl, p-methoxyphenyl, and 2-furanyl, and $R_3$ is phenyl. In a most preferred embodiment, the pharmaceutical composition administered comprises a compound of formula (I) which is selected from the group consisting of

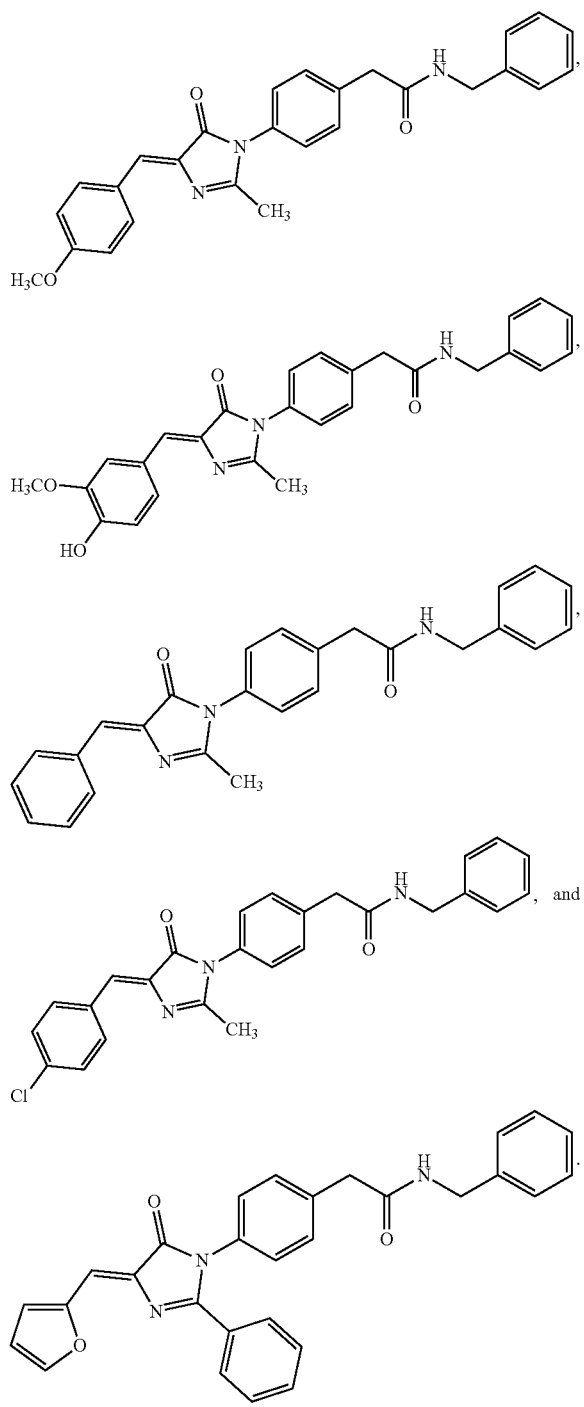

In another embodiment, the pharmaceutical composition administered comprises the compound of formula (II), or a salt thereof, a solvate thereof, a tautomer thereof, or a stereoisomer thereof, in which $R_1'$ is methyl, or phenyl, $R_2'$ is selected from the group consisting of phenyl, p-chlorophenyl, p-hydroxy-m-methoxyphenyl, p-methoxyphenyl, and p-fluoro-o-methylphenyl, and $R_3'$ is selected from the group consisting of phenyl, p-methoxyphenyl, 2-furanyl, p-fluorophenyl, and 4-1,1'-biphenyl. In a most preferred embodiment, the pharmaceutical composition administered comprises a compound of formula (II) which is The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount", "therapeutically effective amount", or "pharmaceutically effective amount" refer to that amount of the active ingredient being administered which will relieve to some extent one or more of the symptoms of the disease being treated. The result can be a reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study. In one or more embodiments, an effective amount of the compound disclosed herein in a range of 0.1-500 mg/kg, preferably 1-200 mg/kg, more preferably 10-50 mg/kg is administered per body weight of the subject. However, in certain embodiments, the effective amount of the compound is less than 0.1 mg/kg or greater than 500 mg/kg.

In treating certain cancers, the best approach is often a combination of surgery, radiotherapy, and/or chemotherapy. Therefore, in at least one embodiment, the pharmaceutical composition is employed in conjunction with radiotherapy. In another embodiment, the pharmaceutical composition is employed with surgery. The radiotherapy and/or surgery may be performed before or after the pharmaceutical composition is administered.

A treatment method may comprise administering a pharmaceutical composition containing the compound of the current disclosure in any of its embodiments as a single dose or multiple individual divided doses. In some embodiments, the composition is administered at various dosages (e.g. a first dose with an effective amount of 200 mg/kg and a second dose with an effective amount of 50 mg/kg). In some embodiments, the interval of time between the administration of the composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, at least 5 days, at least 6 days, or at least 7 days. In certain embodiments, the composition and one or more additional therapies are administered less than 1 day, less than 1 week, less than 2 weeks, less than 3 weeks, less than 4 weeks, less than 1 month, less than 2 months, less than 3 months, less than 6 months, less than 1 year, less than 2 years, or less than 5 years apart.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, at least 10%, at least 15%, at least 20%, at least 25%, at least 30%, at least 40%, at least 50%, at least 60%, at least 70%, at least 75%, at least 80%, at least 85%, at least 90%, at least 95%, at least 99%, or 100%, relative to the tumor size before treatment. In other embodiments, the size of a tumor after treatment does not reduce but is maintained the same as the tumor size before treatment. Methods of assessing tumor size include, but are not limited to, CT scan, MRI, DCE-MRI and PET scan.

In one embodiment, the method disclosed herein may reduce the number of abnormal peripheral blood mononuclear cells in a leukemia patient, who may be afflicted with acute lymphoblastic leukemia (ALL), acute myeloid leukemia (AML), chronic lymphocytic leukemia (CLL), or chronic myeloid leukemia (CIVIL). Preferably, the number of abnormal peripheral blood mononuclear cells is reduced after the treatment by at least 5%, at least 10%, at least 20%, at least 30%, or at least 40%, and up to 100%, up to 99%, up to 95%, up to 90%, up to 80%, or up to 60%, relative to an initial number of abnormal peripheral blood mononuclear cells before treatment.

In most embodiments, the method further comprises measuring a concentration of a biomarker and/or detecting a mutation in a biomarker before and/or after the pharmaceutical composition comprising the compound of the present disclosure is administered. As used herein, the term "biomarker" refers to a characteristic that is objectively measured and evaluated as an indicator of normal biological processes, pathogenic processes or pharmacological responses to a therapeutic intervention. Generic cancer biomarkers include circulating tumor DNA (ctDNA) and circulating tumor cells (CTC). Exemplary biomarkers for breast cancer include, without limitation, BRCA1, BRCA2, HER-2, estrogen receptor, progesterone receptor, cancer antigen 15-3, cancer antigen 27.29, carcinoembryonic antigen, Ki67, cyclin D1, cyclin E, and ERβ. Exemplary biomarkers for prostate cancer include, without limitation, tPSA, fPSA, p2PSA, HOXC6 DLX1, GSTP1, RASSF1, and APC. In one embodiment, leukemia patient's response to the treatment may be monitored by (i) measuring the complete blood count, (ii) observing the disappearance/reduction in occurrences of abnormal cytogenetic markers detected at the time of diagnosis, and/or (iii) observing the disappearance/reduction in occurrences of BCR/ABL mutational copies detected at the time of diagnosis.

The mutation in the biomarker may be detected by procedures such as restriction fragment length polymorphism (RFLP), polymerase chain reaction (PCR) assay, multiplex ligation-dependent probe amplification (MLPA), denaturing gradient gel electrophoresis (DGGE), single-strand conformation polymorphism (SSCP), hetero-duplex analysis, protein truncation test (PTT), and oligonucleotide ligation assay (OLA). The procedures to detect the mutation are well-known to those of ordinary skill in the art.

The term "sample" used herein refers to any biological sample obtained from the subject in need of therapy including a single cell, multiple cells, fragments of cells, a tissue sample, and/or body fluid. Specifically, the biological sample may include red blood cells, white blood cells, platelets, hepatocytes, epithelial cells, endothelial cells, a skin biopsy, a mucosa biopsy, an aliquot of urine, saliva, whole blood, serum, plasma, lymph. In some embodiments, the biological sample is taken from a tumor.

The concentration level of the cancer biomarker in a sample may be measured by an assay, for example an immunoassay. Typical immunoassay methods include, without limitation, enzyme-linked immunosorbent assay (ELISA), enzyme-linked immunospot assay (ELISPOT), Western blotting, immunohistochemistry (IHC), immunocytochemistry, immunostaining, and multiple reaction monitoring (MRM) based mass spectrometric immunoassay. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

In some embodiments, a concentration of the biomarker is measured before and after the administration. When the concentration of the biomarker is maintained, the method may further comprise increasing the effective amount of the compound of the present disclosure by at least 5%, at least 10%, or at least 30%, up to 50%, up to 60%, or up to 80% of an initial effective amount that is in a range of 0.1-500 mg/kg per body weight of the subject. The increased effective amount may be in a range of 0.105-900 mg/kg, preferably 1-500 mg/kg, more preferably 10-250 mg/kg. The subject may be administered with the increased dosage for a longer period (e.g. 1 week more, 2 weeks more, or 2 months more) than the duration prescribed with the initial effective amount.

In some embodiments, the mutation in the biomarker is detected before administering the composition to identify subjects predisposed to the disease. Alternatively, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the administration is stopped once the subject is treated.

The examples below are intended to further illustrate protocols for preparing, characterizing the compounds of formulae (I), (II), and (III), and uses thereof, and are not intended to limit the scope of the claims.

Example 1

Chemical Synthesis: Overview

Figure 4:
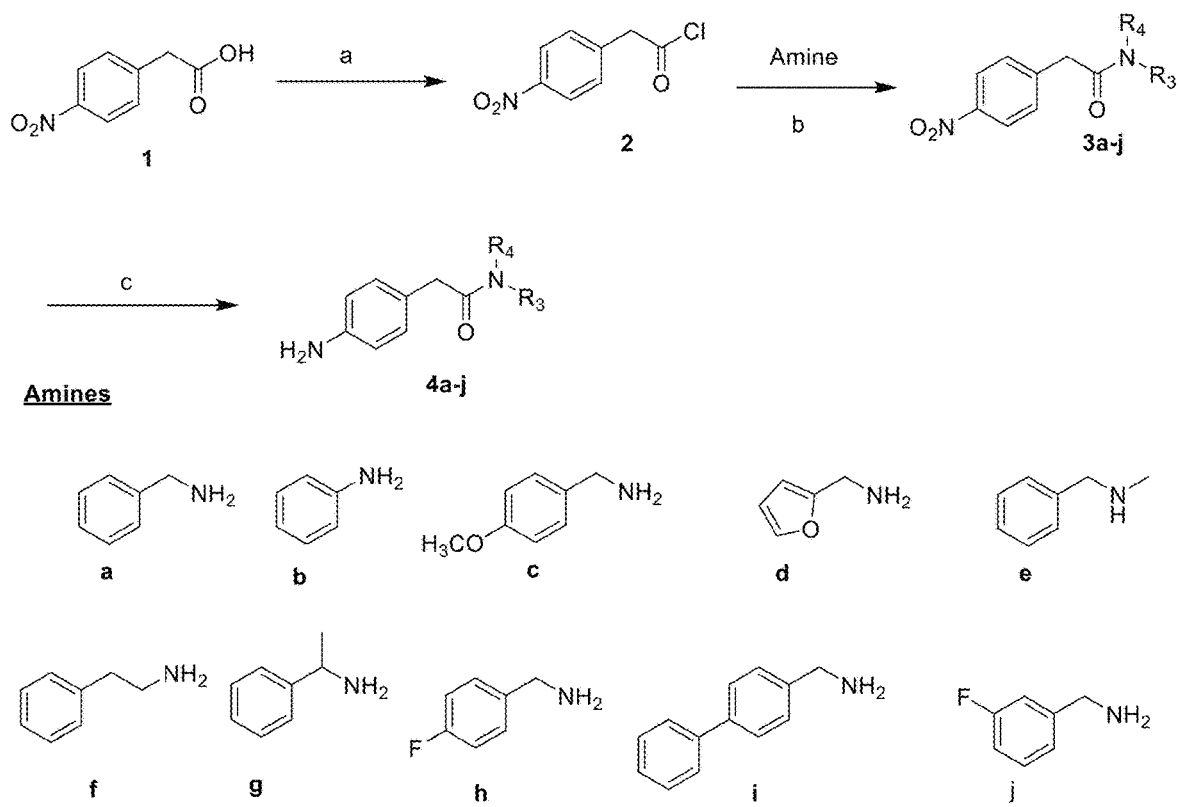
FIG. 4 is a scheme illustrating the synthesis of amine starting materials 4a-j.

First, 2-(4-nitrophenyl)acetic acid 1 was stirred with oxalyl chloride in dichloromethane (DCM) and a catalytic amount of N,N-dimethylformamide (DMF) at room temperature for 4 h to afford 2-(4-nitrophenyl) acetyl chloride 2. In an ice bath, intermediates 3a-j were prepared by the reaction of 2-(4-nitrophenyl) acetyl chloride 2 and the corresponding amine in the presence of diisopropylethylamine (DIPEA) in DCM. The pivotal amines 4a-j were obtained by reduction of the nitro following one of two techniques. One method was heating the nitro intermediate with $SnCl_2$ dihydrate in ethyl acetate for 4 h. Alternatively, the amines were prepared using flow chemistry reduction instrument H-Cube Pro™ (Thales Technology, Hungary) with 10% Pd—C cartridge to catalyze the reduction in high pressure (10 atm.) and temperature (40° C.) (see FIG. 4).

To prepare the oxazolone intermediates (7a-i) for the second portion of KIM compounds, we employed Erlenmeyer chemistry by reacting either N-acetylglycine (5a) or hippuric acid (5b) with the appropriate aldehydes 6a-e. The final step involved reaction of the amine (4a-j) with the corresponding oxazolone (7a-i) in dry pyridine to produce KIM-C (imidazolones) compounds. Alternatively, the oxazolones (7a-i) were heated with the appropriate amine (4a-j) in acetonitrile to give KIM-V compounds (see FIG. 5). The truncated analogue KIM-112V was prepared by reacting oxazolone 7b with p-toluidine under the same conditions mentioned above for the preparation of KIM-V series.

All compounds were characterized by NMR spectroscopy and their molecular formulae were established using HRMS. The purities of the compounds were determined to be higher than 95% using LC/MS.

Example 2

Chemical Synthesis: Experimental

All melting points were uncorrected and measured using the capillary melting point instrument BI 9100 (Barnstead Electrothermal, UK). Infrared spectra were recorded on a Thermo Scientific Niccolet iS10 FT-IR Spectrometer (King Fahd Center for Medical Research, King Abdulaziz University, Jeddah, Saudi Arabia). In this disclosure, only characteristic IR stretching bands were listed, including NH, OH, CH, C=O, C=N, and/or C=C. In FT-IR, all samples were measured neat. $^1$H NMR spectra were recorded on an AVANCE-III 600 MHz and AVANCE-III HD 850 MHz spectrometers (Bruker, Germany), and chemical shifts were expressed as ppm against TMS as an internal reference (King Fahd Center for Medical Research and Faculty of Science, King Abdulaziz University, Jeddah, Saudi Arabia). LC/MS analysis was performed on an Agilent 6320 Ion Trap HPLC-ESI-MS/DAD (Santa Clara, Calif., USA) with the following settings. The analytes were separated using a Macherey-Nagel Nucleodur-C18 column (150 mm length× 4.6 mm i.d., 5 µm) (Macherey-Nagel GMBH & Co. KG, Duren, Germany). Mobile phase, isocratic elution using a mixture of acetonitrile and 0.01 formic acid in water (80:20, v/v). The flow rate was 0.4 mL/min; total run time=20 min. Purities were reported according to percentage of Peak Areas at a wavelength of 280 nm. High-resolution mass spectrometry (HRMS) was performed in the Faculty of Science, King Abdulaziz University on Impact II™ Q-TOF spectrometer (Bruker, Germany). Column chromatography was performed on a silica gel 60 (particle size 0.06 mm-0.20 mm).

Example 3

General Procedure for Preparation of Amines 4a-4j

A mixture of 2-(4-nitrophenyl)acetic acid (10 mmol, 1.81 g) and 50 mL dichloromethane (DCM) was placed in a dry 3-neck round bottom flask, flushed with nitrogen, and stirred in an ice bath. Then, oxalyl chloride (11.6 mmol, 1.48 g, 1 mL) in 5 mL DCM was placed in an addition funnel and was then fast-dropped to the original mixture. After the addition of oxalyl chloride was completed, 1 drop of dimethylformamide (DMF) was added. 15 min later, the ice bath was removed and the mixture was stirred at room temperature (r.t.) for 4 hours as all the acid dissolved completely. The solvent was removed using rotary evaporator and the residue 2-(4-nitrophenyl)acetyl chloride 2 was collected, dissolved in 40 mL DCM, and stirred in an ice bath for 10 min. The appropriate amine (a-j, FIG. 4) (10 mmol, 1.1 g, 1.1 mL) was added using an addition funnel, along with diisopropylethylamine (DIPEA) (10 mmol, 1.55 g, 2.1 mL) in 40 mL DCM, which was added drop wise to the acid chloride. After the ice melted, the stirring continued overnight at room temperature. The solid particles were collected by filtration, and washed with a small amount of DCM. Yellowish white crystalline solid was observed. The completion of the reaction was checked by TLC for both the solid and filtrate using ethyl acetate hexane mixture in the ratio of 1:1 against the starting materials. The filtrate was neutralized by HCl (1 M) and the organic layer was collected, dried using sodium sulfate. After the solvent was rotavaped, a solid (3a-j) was collected and washed with ether.

In a 150 mL round bottom flask rapped with Aluminum foil, a mixture of N-benzyl-2-(4-nitrophenyl)acetamide (6.58 mmol, 1.78 g), $SnCl_2$ dihydrate (26.34 mmol, 5.95 g), ethyl acetate (40 mL), and water (0.5 mL) was refluxed for 4 hours. The mixture was then cooled, diluted by ethyl acetate (40 mL), and treated with a cold solution of 40% NaOH (80 mL), thereby forming an emulsion. Fresh water was added to break the emulsion. The organic layer was separated. The aqueous layer was washed with 10 mL of ethyl acetate, then combined with the organic layer. The combined layers were washed with 15 mL of brine and dried with magnesium sulfate. The ethyl acetate was removed using rotary evaporator and a solid product was collected.

Example 4

Characterization of Amines 4a-4j 2-(4-aminophenyl)-N-benzylacetamide (4a)

The amine 4a was synthesized according to the procedure above and its characterization data were found similar to literature [Kumar, M.; Sharma, S.; Thakur, K.; Nayal, O. S.; Bhatt, V.; Thakur, M. S.; Kumar, N.; Singh, B.; Sharma, U., Montmorillonite-K10-Catalyzed Microwave-Assisted Direct Amidation of Unactivated Carboxylic Acids with Amines: Maintaining Chiral Integrity of Substrates. *Asian J. Org. Chem.* 2017, 6 (3), 342-346, incorporated herein by reference in its entirety]. Melting point: 140-142° C. Yield: 1.55 g (98.7%). The compound was used for the next step without further characterization.

2-(4-aminophenyl)-N-phenylacetamide (4b)

$^1$H NMR (600 MHz, CDCl$_3$) δ 7.41 (d, J=7.53 Hz, 2H), 7.21-7.35 (m, 2H), 7.04-7.20 (m, 2H), 6.73 (d, J=7.91 Hz, 1H), 3.74 (br. s., 1H), 3.64 (s, 1H).

2-(4-aminophenyl)-N-(4-methoxybenzyl)acetamide (4c)

$^1$H NMR (600 MHz, CDCl$_3$) δ 7.10 (d, J=8.66 Hz, 1H), 7.02 (d, J=8.28 Hz, 1H), 6.78-6.92 (m, 1H), 6.61-6.75 (m, 1H), 5.71 (br. s., 1H), 4.32 (d, J=5.65 Hz, 1H), 3.75-3.86 (m, 2H), 3.67 (br. s., 1H), 3.44-3.59 (m, 1H).

2-(4-aminophenyl)-N-(furan-2-ylmethyl)acetamide (4d)

¹H NMR (600 MHz, CDCl₃) δ 7.02 (d, J=8.28 Hz, 2H), 6.65 (d, J=8.28 Hz, 2H), 6.28 (br. s., 1H), 6.13 (br. s., 1H), 5.78 (br. s., 1H), 4.38 (d, J=5.65 Hz, 2H), 3.70 (br. s., 2H), 3.43-3.60 (m, 2H).

2-(4-aminophenyl)-N-phenethylacetamide (4f)

¹H NMR (600 MHz, CDCl₃) δ 7.17-7.34 (m, 3H), 7.05 (d, J=7.53 Hz, 2H), 6.94 (d, J=8.28 Hz, 2H), 6.63 (d, J=7.91 Hz, 2H), 5.43 (br. s., 1H), 3.70 (br. s., 1H), 3.38-3.56 (m, 4H), 2.68-2.81 (m, 2H). ¹³C NMR (151 MHz, CDCl₃) δ 171.7, 145.6, 138.8, 130.5, 128.7, 128.5, 126.4, 124.4, 115.6, 43.0, 40.7, 35.6.

2-(4-aminophenyl)-N-(1-phenylethyl)acetamide (4g)

¹H NMR (600 MHz, CDCl₃) δ 7.28 (d, J=11.67 Hz, 1H), 7.17-7.26 (m, 2H), 7.03 (d, J=7.91 Hz, 2H), 6.67 (d, J=8.28 Hz, 2H), 5.65 (br. s., 1H), 5.13 (dd, J=6.96, 14.12 Hz, 1H), 3.70 (br. s., 1H), 3.46-3.55 (m, 2H), 1.35-1.46 (m, 3H).

2-(4-aminophenyl)-N-(4-fluorobenzyl)acetamide (4h)

¹H NMR (600 MHz CDCl₃) δ 7.10-7.22 (m, 2H), 7.03 (d, J=8.28 Hz, 2H), 6.93-7.01 (m, 1H), 6.66 (d, J=8.28 Hz, 2H), 5.74 (br. s., 1H), 4.36 (d, J=5.65 Hz, 2H), 3.69 (br. s., 2H), 3.52 (s, 2H).

N-([1,1'-biphenyl]-4-ylmethyl)-2-(4-aminophenyl)acetamide (4i)

¹H NMR (600 MHz, CDCl₃) δ 7.50-7.64 (m, 3H), 7.41-7.50 (m, 2H), 7.35 (d, J=7.15 Hz, 1H), 7.22-7.32 (m, 4H), 7.06 (d, J=7.91 Hz, 2H), 6.67 (d, J=8.28 Hz, 1H), 5.76 (br. s., 1H), 4.45 (d, J=6.02 Hz, 1H), 3.68 (br. s., 1H), 3.55 (s, 1H).

2-(4-aminophenyl)-N-(3-fluorobenzyl)acetamide (4j)

¹H NMR (600 MHz, CDCl₃) δ 7.21-7.34 (m, 1H), 7.05 (d, J=7.91 Hz, 2H), 6.90-7.02 (m, 2H), 6.88 (d, J=9.79 Hz, 1H), 6.67 (d, J=8.28 Hz, 2H), 5.77 (br. s., 1H), 4.39 (d, J=6.02 Hz, 2H), 3.70 (br. s., 1H), 3.52-3.61 (m, 2H). ¹³C NMR (151 MHz, CDCl₃) δ 171.8, 163.8, 145.8, 141.0, 130.5, 130.1, 130.1, 124.2, 122.9, 115.7, 114.3, 114.1, 43.0, 42.9.

Example 5

General Procedure for the Preparation of (Z)-4-arylidene-2-substituted oxazol-5(4H)-one Intermediates (7a-i)

The acylglycine 5a or 5b (10 mmol) was mixed with an equimolar amount of appropriate aldehyde 6a-e, acetic anhydride (1.9 mL, 2 equiv.) and freshly dried sodium acetate (0.08 g, 0.1 equiv.). The mixture was heated at 80° C. for 30 min then cooled. The resulting solid was washed with water and sodium bicarbonate solution, and dried by vacuum filtration. The yellow solid was washed with petroleum ether several times and used without further purification for the next step.

Example 6

General Procedure for the Synthesis of KIM-C Derivatives

The appropriate oxazolone 7a-i (2 mmol) was mixed with an amine 4a (0.48 g, 2 mmol) in dry pyridine (6 mL) under inert atmosphere. The mixture was heated in Integrity Stem 10 Reactor (Cole Parmer, England) at 100° C. for 8 hours. The mixture was cooled and poured into ice/HCl mixture. The precipitated solid was collected by filtration, washed with water, and purified by silica gel chromatography (gradient petroleum-ether to 10% ethyl acetate in petroleum ether).

Example 7

(Z)—N-benzyl-2-(4-(4-benzylidene-2-methyl-5-oxo-4,5-dihydro-1H-imidazol-1-yl)phenyl)acetamide (KIM-111C)

This compound was off-white solid, m.p. 164-165° C.; ¹H NMR (600 MHz, CDCl₃) δ 8.19 (d, J=6.78 Hz, 2H), 7.41-7.52 (m, 5H), 7.34 (t, J=7.15 Hz, 2H), 7.20-7.32 (m, 6H), 6.03 (br. s., 1H), 4.46 (d, J=5.65 Hz, 2H), 3.65 (br. s., 2H).

Example 8

(Z)—N-benzyl-2-(4-(4-(4-chlorobenzylidene)-2-methyl-5-oxo-4,5-dihydro-1H-imidazol-1-yl)phenyl)acetamide (KIM-121C)

This compound was off-white solid, m.p. 209-211° C.; ¹H NMR (600 MHz, CDCl₃) δ 8.12-8.18 (m, 2H), 7.45 (d, J=8.28 Hz, 2H), 7.47 (d, J=7.91 Hz, 2H), 7.32-7.37 (m, 2H), 7.23-7.32 (m, 6H), 7.17 (s, 1H), 5.88 (br. s., 1H), 4.44-4.50 (m, 2H), 3.65-3.71 (m, 2H), 2.35 (s, 3H).

Example 9

(Z)—N-benzyl-2-(4-(4-(4-hydroxy-3-methoxybenzylidene)-2-methyl-5-oxo-4,5-dihydro-1H-imidazol-1-yl)phenyl)acetamide (KIM-131C)

This compound was off-white solid, m.p. 199-200° C.; ¹H NMR (600 MHz, CDCl₃) δ 8.05 (s., 1H), 7.57 (d, J=7.53 Hz, 1H), 7.44 (d, J=7.53 Hz, 2H), 7.33 (d, J=7.15 Hz, 2H), 7.20-7.31 (m, 5H), 7.15 (s, 1H), 6.98 (d, J=8.28 Hz, 1H), 6.03 (br. s., 1H), 5.11 (br. s., 1H), 4.44-4.49 (d, 2H), 4.01 (s., 3H), 3.67 (s, 2H), 3.49 (br. s., 2H), 2.30 (s, 3H).

Example 10

(Z)—N-benzyl-2-(4-(4-(4-methoxybenzylidene)-2-methyl-5-oxo-4,5-dihydro-1H-imidazol-1-yl)phenyl)acetamide (MM-161C)

This compound was off-white solid, m.p. 185° C.; ¹H NMR (600 MHz, CDCl₃) δ 8.18 (d, J=8.66 Hz, 2H), 7.44 (d, J=7.91 Hz, 2H), 7.32-7.37 (m, 2H), 7.22-7.32 (m, 5H), 7.18 (s, 1H), 7.00 (d, J=8.66 Hz, 2H), 5.97 (br. s., 1H), 4.46 (d, J=5.65 Hz, 2H), 3.89 (s, 3H), 3.66 (s, 2H), 2.30 (s, 3H).

Example 11

(Z)—N-benzyl-2-(4-(4-benzylidene-5-oxo-2-phenyl-4,5-dihydro-1H-imidazol-1-yl)phenyl)acetamide (KIM-211C)

This compound was yellow solid, m.p. 218-219° C.; ¹H NMR (600 MHz, CDCl₃) δ 8.24-8.28 (m, 2H), 7.57 (dd, J=1.13, 8.28 Hz, 2H), 7.44-7.47 (m, 3H), 7.37 (d, J=8.28 Hz, 2H), 7.28-7.35 (m, 7H), 7.23-7.26 (m, 2H), 7.16-7.19 (m, 2H), 5.81 (br. s., 1H), 4.45-4.48 (m, 2H), 3.67 (s, 2H).

Example 12

(Z)—N-benzyl-2-(4-(4-(4-chlorobenzylidene)-5-oxo-2-phenyl-4,5-dihydro-1H-imidazol-1-yl)phenyl)acetamide (KIM-221C)

This compound was pale yellow solid, m.p. 218-220° C.; $^1$H NMR (600 MHz, CDCl$_3$) δ 8.24-8.28 (m, 2H), 7.57 (dd, J=1.13, 8.28 Hz, 2H), 7.45-7.47 (m, 2H), 7.37 (d, J=8.28 Hz, 2H), 7.29-7.35 (m, 6H), 7.23-7.26 (m, 2H), 7.16-7.19 (m, 2H), 5.81 (br. s., 1H), 4.47 (d, J=5.65 Hz, 2H), 3.67 (s, 2H).

Example 13

(Z)—N-benzyl-2-(4-(4-(4-hydroxy-3-methoxybenzylidene)-5-oxo-2-phenyl-4,5-dihydro-1H-imidazol-1-yl)phenyl)acetamide (KIM-231C)

This compound was pale orange-yellow solid, m.p. 109-112° C.; $^1$H NMR (600 MHz, CDCl$_3$) δ 8.28 (s, 1H), 7.73 (d, J=8.28 Hz, 1H), 7.55 (d, J=7.91 Hz, 2H), 7.44 (dd, J=7.40 and 7.24 Hz, 1H), 7.32-7.39 (m, 4H), 7.26-7.31 (m, 4H), 7.24 (d, J=7.15 Hz, 2H), 7.18 (d, J=6.40 Hz, 2H), 7.14 (d, J=7.91 Hz, 1H), 5.85 (br. s., 1H), 4.43-4.48 (m, 2H), 4.03 (br. s., 1H), 3.96 (s, 3H), 3.67 (s, 2H).

Example 14

(Z)—N-benzyl-2-(4-(4-(furan-2-ylmethylene)-5-oxo-2-phenyl-4,5-dihydro-1H-imidazol-1-yl)phenyl)acetamide (KIM-241C)

This compound was pale orange-yellow solid, m.p. 199-200° C.; $^1$H NMR (600 MHz, CDCl$_3$) δ 7.68-7.72 (m, 1H), 7.53-7.61 (m, 3H), 7.40-7.49 (m, 1H), 7.31-7.39 (m, 4H), 7.21-7.31 (m, 6H), 7.14-7.20 (m, 2H), 6.66 (dd, J=2.07, 3.20 Hz, 1H), 5.85 (br. s., 1H), 4.43-4.49 (m, 2H), 3.66 (s, 2H).

Example 15

(Z)—N-benzyl-2-(4-(4-(4-methoxybenzylidene)-5-oxo-2-phenyl-4,5-dihydro-1H-imidazol-1-yl)phenyl)acetamide (KIM-261C)

This compound was pale orange-yellow solid, m.p. 193° C.; $^1$H NMR (600 MHz, CDCl$_3$) δ 8.30 (d, J=9.03 Hz, 2H), 7.52-7.58 (m, 2H), 7.39-7.45 (m, 1H), 7.26-7.37 (m, 8H), 7.24 (d, J=7.53 Hz, 2H), 7.14-7.20 (m, 2H), 7.02 (d, J=9.03 Hz, 2H), 5.84 (br. s., 1H), 4.43-4.48 (m, 2H), 3.88-3.93 (m, 3H), 3.67 (br. s., 2H).

Example 16

General Procedure for Synthesis of KIM-V Compounds

The appropriate oxazolone 7a-i (2 mmol) was mixed with the amine 4a-j (0.48 g, 2 mmol) in acetonitrile (6 mL) under inert atmosphere. The mixture was heated to 80° C. for 8 hours in Integrity Stem 10™ Reactor (Cole Parmer, England). The mixture was cooled and poured into an ice/HCl mixture. The precipitated solid was collected by filtration, washed with water, and purified by silica gel chromatography (gradient dichloromethane to 5% MeOH in dichloromethane).

Example 17

(E)-2-acetamido-N-(4-(2-(benzylamino)-2-oxoethyl)phenyl)-3-phenylacrylamide (KIM-111V)

The purified product KIM-111V was a white solid, m.p. 197° C. IR (KBr, $v_{max}$ cm$^{-1}$) 3236, 3086, 1659, 1638, 1599, 1533, 1505, 1270; $^1$H NMR $^1$H NMR (600 MHz, DMSO-d$_6$) δ 7.61 (d, J=7.91 Hz, 1H), 7.64 (d, J=8.66 Hz, 2H), 7.40-7.48 (m, 1H), 7.29-7.39 (m, 2H), 7.21-7.28 (m, 3H), 4.25-4.32 (m, 2H), 3.45 (br. s., 1H), 2.04 (s, 2H); LC-MS (ESI), m/z 428.1969 [M+H]$^+$. Purity: 97%.

Example 18

(E)-2-acetamido-N-(4-(2-(benzylamino)-2-oxoethyl)phenyl)-3-(4-chlorophenyl)acrylamide (KIM-121V)

This compound was prepared according to the procedure described for the synthesis of KIM-111V starting from oxazolone 7b (2 mmol, 0.443 g) and 2-(4-aminophenyl)-N-benzylacetamide (2.2 mmol, 0.529 g). The product KIM-121V was white solid, m.p.>300° C. (dec); IR (KBr, $v_{max}$ cm$^{-1}$) 3243, 3065, 1724, 1647, 1546, 1395, 1329; $^1$H NMR (600 MHz, DMSO-d$_6$) δ 7.60-7.71 (m, 2H), 7.40-7.51 (m, 2H), 7.29-7.34 (m, 2H), 7.18-7.29 (m, 3H), 4.28 (d, J=5.65 Hz, 1H), 3.45 (s, 1H), 2.02 (s, 1H), 1.63 (d, J=1.88 Hz, 2H); $^{13}$C NMR (151 MHz, DMSO-d$_6$) δ 175.1, 134.2, 131.8, 131.5, 130.7, 129.7, 129.6, 129.2, 129.0, 128.1, 127.9, 127.7, 127.4, 120.6, 40.6, 40.5, 40.3, 40.2, 40.0, 39.9, 39.7, 25.4; Purity 93%.

Example 19

(E)-2-acetamido-N-(4-(2-(benzylamino)-2-oxoethyl)phenyl)-3-(4-hydroxy-3-methoxyphenyl) acrylamide (KIM-131V)

This compound was prepared according to the procedure described for the synthesis of KIM-111V starting from oxazolone 7c (2 mmol, 0.446 g) and 2-(4-aminophenyl)-N-benzylacetamide (2.2 mmol, 0.529 g; $^1$H NMR (600 MHz, Acetone) δ 9.38 (s, 1H), 8.97 (s, 1H), 7.70 (d, J=8.66 Hz, 1H), 7.33-7.35 (m, 1H), 7.26-7.32 (m, 5H), 7.23 (d, J=6.78 Hz, 1H), 7.15 (d, J=1.88 Hz, 1H), 7.06-7.10 (m, 2H), 4.40 (d, J=6.02 Hz, 2H), 3.86 (s, 2H), 3.55 (s, 2H), 2.28 (s, 3H), 2.16 (s, 2H), 1.31 (br. s., 1H).

Example 20

(E)-2-acetamido-N-(4-(2-(benzylamino)-2-oxoethyl)phenyl)-3-(4-methoxyphenyl) acrylamide (KIM-161V)

This compound was prepared according to the procedure described for the synthesis of KIM-111V starting from oxazolone 7d (2 mmol, 0.434 g) and 2-(4-aminophenyl)-N-benzylacetamide (2.2 mmol, 0.529 g). The product KIM-161V was white solid, m.p. 189-200° C.; $^1$H NMR (600 MHz, DMSO-d$_6$) δ 7.63 (d, J=8.66 Hz, 2H), 7.58 (d, J=8.66 Hz, 2H), 7.29-7.36 (m, 3H), 7.21-7.27 (m, 6H), 6.97-7.03 (m, 3H), 4.28 (d, J=6.02 Hz, 2H), 3.80 (s, 4H), 3.45 (s, 2H), 2.05 (s, 3H); $^{13}$C NMR (151 MHz, DMSO) δ 171.0, 168.9, 140.1, 138.4, 131.6, 129.9, 129.0, 127.9, 127.5, 119.6, 42.9, 42.5, 40.7, 40.6, 40.5, 40.3, 40.2, 40.0, 39.9, 39.8, 24.6.

Example 21

(E)-N-(3-((4-(2-(benzylamino)-2-oxoethyl)phenyl)amino)-3-oxo-1-phenylprop-1-en-2-yl) benzamide (KIM-211V)

This compound was prepared according to the procedure described for the synthesis of KIM-111V starting from oxazolone 7e (2 mmol, 0.498 g) and 2-(4-aminophenyl)-N-benzylacetamide (2.2 mmol, 0.498 g). The product KIM-211V was white solid, m.p. 214-216° C.; $^1$H NMR (600 MHz, DMSO-$d_6$) δ 10.11 (s, 1H), 10.14 (s, 1H), 8.51 (br. s., 1H), 8.00-8.06 (m, J=7.53 Hz, 2H), 7.62-7.69 (m, 4H), 7.61 (d, J=6.78 Hz, 1H), 7.54 (t, J=7.34 Hz, 2H), 7.37-7.43 (m, 2H), 7.28-7.36 (m, 3H), 7.21-7.27 (m, 5H), 7.17 (s, 1H), 4.28 (d, J=5.65 Hz, 2H); $^{13}$C NMR (151 MHz, CDCl$_3$) δ 175.8, 171.5, 169.7, 169.7, 144.9, 143.1, 139.7, 138.9, 136.8, 136.4, 135.0, 134.5, 134.4, 134.1, 133.9, 133.8, 133.4, 133.3, 132.6, 132.2, 132.2, 125.6, 125.4, 47.6, 47.3.

Example 22

(E)-N-(3-((4-(2-(benzylamino)-2-oxoethyl)phenyl)amino)-1-(4-chlorophenyl)-3-oxoprop-1-en-2-yl)benzamide (KIM-221V)

This compound was prepared according to the procedure described for the synthesis of KIM-111V starting from oxazolone 7f (2 mmol, 0.498 g) and 2-(4-aminophenyl)-N-benzylacetamide (2.2 mmol, 0.567 g). The product KIM-221V was white solid, m.p. 255° C.; IR (KBr, $\nu_{max}$ cm$^{-1}$) 3283, 1684, 1638, 1535, 1480, 1311; $^1$H NMR (600 MHz, DMSO-$d_6$) δ 10.20 (br. s., 1H), 10.15 (br. s., 1H), 8.51 (d, J=5.65 Hz, 1H), 8.03 (d, J=7.15 Hz, 2H), 7.59-7.70 (m, 5H), 7.52-7.58 (m, 2H), 7.45-7.50 (m, 2H), 7.32 (t, J=7.53 Hz, 2H), 7.24 (d, J=6.78 Hz, 4H), 7.13 (br. s., 1H), 4.28 (d, J=5.27 Hz, 2H), 3.46 (br. s., 2H).

Example 23

(E)-N-(3-((4-(2-(benzylamino)-2-oxoethyl)phenyl)amino)-1-(4-hydroxy-3-methoxyphenyl)-3-oxoprop-1-en-2-yl)benzamide (KIM-231V)

This compound was prepared according to the procedure described for the synthesis of KIM-111V starting from oxazolone 7g (2 mmol, 0.498 g) and 2-(4-aminophenyl)-N-benzylacetamide (2.2 mmol, 0.590 g). The product KIM-231V was white solid, m.p. 186-188° C.; $^1$H NMR (600 MHz, DMSO-$d_6$) δ 9.89 (br. s., 1H), 8.50 (br. s., 1H), 7.50 (d, J=8.28 Hz, 3H), 7.28-7.35 (m, 3H), 7.17-7.27 (m, 6H), 4.27 (d, J=5.65 Hz, 3H), 3.42 (s, 3H), 2.04 (s, 4H); $^{13}$C NMR (151 MHz, Acetone) δ 168.2, 167.0, 164.9, 163.9, 161.3, 151.8, 151.5, 142.7, 139.1, 133.8, 132.7, 130.4, 129.5, 128.4, 127.8, 126.0, 123.6, 115.8, 115.2, 55.7, 19.9.

Example 24

(E)-N-(3-((4-(2-(benzylamino)-2-oxoethyl)phenyl)amino)-1-(4-methoxyphenyl)-3-oxoprop-1-en-2-yl)benzamide (KIM-261V)

This compound was prepared according to the procedure described for the synthesis of KIM-111V starting from oxazolone 7i (2 mmol, 0.558 g) and 2-(4-aminophenyl)-N-benzylacetamide (2.2 mmol, 0.590 g). The product KIM-261V was white solid, mp 186-188° C.; $^1$H NMR (600 MHz, DMSO-$d_6$) δ 9.88 (br. s., 1H), 8.50 (d, J=5.27 Hz, 1H), 7.50 (d, J=8.28 Hz, 3H), 7.31 (t, J=7.53 Hz, 3H), 7.22-7.27 (m, 4H), 7.19 (d, J=8.28 Hz, 3H), 4.27 (d, J=6.02 Hz, 3H), 3.42 (s, 3H), 2.04 (s, 4H); $^{13}$C NMR (151 MHz, DMSO) δ 171.0, 168.9, 140.1, 138.4, 131.6, 129.9, 129.0, 127.9, 127.5, 119.6, 42.9, 42.5, 24.6.

Example 25

(E)-N-(3-((4-(2-(benzylamino)-2-oxoethyl)phenyl)amino)-1-(4-fluoro-2-methylphenyl)-3-oxoprop-1-en-2-yl)benzamide (KIM-2101V)

This compound was prepared according to the procedure described for the synthesis of KIM-111V starting from oxazolone 7j (2 mmol, 0.562 g) and 2-(4-aminophenyl)-N-benzylacetamide (2.2 mmol, 0.590 g). The product KIM-2101V was white solid, m.p. 156° C.; $^1$H NMR (600 MHz, Acetone) δ 8.07 (d, J=7.53 Hz, 2H), 7.72 (dd, J=2.64, 8.66 Hz, 2H), 7.67 (d, J=9.79 Hz, 2H), 7.59-7.65 (m, 3H), 7.53 (t, J=7.72 Hz, 2H), 7.41 (d, J=8.66 Hz, 2H), 7.33 (d, J=8.66 Hz, 2H), 7.30 (br. s., 1H), 7.26-7.29 (m, 2H), 7.05 (t, J=7.91 Hz, 1H), 3.67 (s, 2H).

Example 26

(E)-N-(1-(4-chlorophenyl)-3-oxo-3-((4-(2-oxo-2-(phenylamino)ethyl)phenyl)amino)prop-1-en-2-yl)benzamide (KIM-22101V)

This compound was prepared according to the procedure described for the synthesis of KIM-111V starting from oxazolone 7f (2 mmol, 0.567 g) and 2-(4-aminophenyl)-N-phenylacetamide (2.2 mmol, 0.497 g). The product KIM-22101V was white solid, m.p. 166-175° C.; $^1$H NMR (600 MHz, Acetone) δ 8.07 (d, J=7.53 Hz, 2H), 7.72 (dd, J=2.64, 8.66 Hz, 2H), 7.67 (d, J=9.79 Hz, 2H), 7.59-7.65 (m, 3H), 7.53 (t, J=7.72 Hz, 2H), 7.41 (d, J=8.66 Hz, 2H), 7.33 (d, J=8.66 Hz, 2H), 7.30 (br. s., 1H), 7.26-7.29 (m, 2H), 7.05 (t, J=7.91 Hz, 1H), 3.67 (s, 2H); $^{13}$C NMR (151 MHz, DMSO) δ 169.7, 166.7, 164.3, 140.1, 138.5, 134.4, 134.2, 132.6, 132.1, 131.9, 131.6, 130.7, 130.1, 130.0, 129.3, 129.1, 128.5, 128.3, 128.0, 123.9, 120.7, 119.8, 43.9.

Example 27

(E)-N-(1-(4-chlorophenyl)-3-((4-(2-((4-methoxybenzyl)amino)-2-oxoethyl)phenyl)amino)-3-oxoprop-1-en-2-yl)benzamide (KIM-2216V)

This compound was prepared according to the procedure described for the synthesis of KIM-111V starting from oxazolone 7f (2 mmol, 0.567 g) and 2-(4-aminophenyl)-N-(4-methoxybenzyl)acetamide (2.2 mmol, 0.594 g). The product KIM-2216V was white solid, m.p. 166-175° C.; $^1$H NMR (600 MHz, Acetone) δ 7.69 (d, J=8.66 Hz, 2H), 7.58-7.66 (m, 2H), 7.54 (t, J=7.53 Hz, 2H), 7.42 (d, J=8.28 Hz, 3H), 7.24-7.34 (m, 3H), 7.19 (d, J=8.66 Hz, 2H), 6.84-6.88 (m, 2H), 4.31 (s, 2H), 3.77 (s, 3H), 2.82 (br. s., 5H); $^{13}$C NMR (151 MHz, DMSO) δ 170.8, 166.7, 164.2, 159.5, 138.4, 134.4, 134.2, 132.6, 132.3, 131.6, 130.7, 130.0, 129.3, 129.1, 128.5, 127.9, 120.6, 120.5, 114.3, 55.3, 43.0, 42.7.

Example 28

(E)-N-(1-(4-chlorophenyl)-3-((4-(2-((furan-2-ylmethyl)amino)-2-oxoethyl)phenyl)amino)-3-oxoprop-1-en-2-yl)benzamide (KIM-2230V)

This compound was prepared according to the procedure described for the synthesis of KIM-111V starting from oxazolone 7f (2 mmol, 0.567 g) and 2-(4-aminophenyl)-N-(furan-2-ylmethyl)acetamide (2.2 mmol, 0.506 g). The product KIM-2230V was white solid, m.p. 217-218° C.; $^1$H NMR (600 MHz, Acetone) δ 7.67-7.84 (m, 2H), 7.58-7.66 (m, 2H), 7.54 (t, J=7.72 Hz, 3H), 7.38-7.48 (m, 3H), 7.22-7.37 (m, 3H), 4.34-4.49 (m, 2H), 3.48-3.66 (m, 2H), 2.84 (br. s., 4H); $^{13}$C NMR (151 MHz, CDCl$_3$) δ 156.1, 155.2, 154.9, 143.1, 142.8, 142.5, 142.5, 140.9, 140.2, 139.8, 139.0, 138.7, 137.2, 132.2, 130.7, 130.2, 129.4, 129.2, 129.2, 129.1, 127.8, 121.0, 110.7, 110.2, 107.7, 43.2, 36.9.

Example 29

(E)-N-(3-((4-(2-(benzyl(methyl)amino)-2-oxoethyl)phenyl)amino)-1-(4-chlorophenyl)-3-oxoprop-1-en-2-yl)benzamide (KIM-2245V)

This compound was prepared according to the procedure described for the synthesis of KIM-111V starting from oxazolone 7f (2 mmol, 0.567 g) and 2-(4-aminophenyl)-N-benzyl-N-methylacetamide (2.2 mmol, 0.559 g). The product KIM-2245 was white solid, m.p. 112° C.; $^1$H NMR (600 MHz, Acetone) δ 8.07 (d, J=7.53 Hz, 2H), 7.66-7.86 (m, 2H), 7.57-7.66 (m, 3H), 7.47-7.57 (m, 2H), 7.35-7.47 (m, 3H), 7.29-7.35 (m, 2H), 7.19-7.29 (m, 5H), 4.66 (s, 1H), 4.60 (s, 1H), 3.79 (s, 1H), 3.75 (s, 1H), 2.99 (s, 2H), 2.88 (s, 1H); $^{13}$C NMR (151 MHz, DMSO) δ 171.5, 171.4, 166.8, 164.5, 138.8, 138.4, 138.2, 134.4, 134.2, 132.6, 132.3, 131.7, 131.6, 129.8, 129.4, 129.3, 129.1, 129.1, 128.5, 128.5, 128.0, 127.9, 127.7, 127.4, 120.8, 120.7, 53.8, 50.9, 40.5, 40.2, 35.3, 33.7.

Example 30

(E)-N-(1-(4-chlorophenyl)-3-oxo-3-((4-(2-oxo-2-(phenethylamino)ethyl)phenyl)amino)prop-1-en-2-yl)benzamide (KIM-2246V)

This compound was prepared according to the procedure described for the synthesis of KIM-111V starting from oxazolone 7f (2 mmol, 0.567 g) and 2-(4-aminophenyl)-N-phenethylacetamide (2.2 mmol, 0.540 g). The product KIM-2246V was white solid, m.p. 135° C.; $^1$H NMR (600 MHz, Acetone) δ 9.58 (s, 1H), 8.08 (d, J=7.91 Hz, 2H), 7.68 (dd, J=2.45, 8.47 Hz, 2H), 7.60-7.65 (m, 3H), 7.51-7.56 (m, 2H), 7.39-7.43 (m, 2H), 7.24-7.30 (m, 3H), 7.15-7.24 (m, 5H), 3.39-3.45 (m, 4H), 2.77 (t, J=7.34 Hz, 2H).

Example 31

(E)-N-(1-(4-chlorophenyl)-3-oxo-3-((4-(2-oxo-2-((1-phenylethyl)amino)ethyl)phenyl)amino) prop-1-en-2-yl)benzamide (KIM-2247V)

This compound was prepared according to the procedure described for the synthesis of KIM-111V starting from oxazolone 7f (2 mmol, 0.539 g) and 2-(4-aminophenyl)-N-(1-phenylethyl)acetamide (2.2 mmol, 0.540 g). The product KIM-2247V was white solid, m.p. 192° C.; $^1$H NMR (600 MHz, Acetone) δ 8.07 (d, J=7.53 Hz, 2H), 7.68 (d, J=8.28 Hz, 2H), 7.59-7.65 (m, 3H), 7.53 (t, J=7.72 Hz, 2H), 7.41 (d, J=8.66 Hz, 2H), 7.18-7.37 (m, 8H), 5.07 (q, J=7.15 Hz, 1H), 3.50 (s, 2H), 1.42 (d, J=6.78 Hz, 3H); $^{13}$C NMR (151 MHz, DMSO) δ 170.0, 145.3, 134.4, 134.3, 134.2, 132.6, 132.4, 132.2, 131.6, 130.7, 129.9, 129.3, 129.1, 129.0, 128.9, 128.5, 128.3, 128.0, 127.3, 126.7, 120.6, 120.4, 49.0, 43.0, 22.4.

Example 32

(E)-N-(1-(4-chlorophenyl)-3-((4-(2-((4-fluorobenzyl)amino)-2-oxoethyl)phenyl)amino)-3-oxoprop-1-en-2-yl)benzamide (KIM-2248V)

This compound was prepared according to the procedure described for the synthesis of KIM-111V starting from oxazolone 7f (2 mmol, 0.539 g) and 2-(4-aminophenyl)-N-(4-fluorobenzyl)acetamide (2.2 mmol, 0.568 g). The product KIM-2248V was white solid, m.p. 216° C.; $^1$H NMR (600 MHz, Acetone) δ 8.08 (d, J=7.53 Hz, 2H), 7.68-7.72 (m, 2H), 7.63 (d, J=8.28 Hz, 3H), 7.54 (t, J=7.72 Hz, 2H), 7.41 (d, J=8.28 Hz, 2H), 7.31 (dd, J=5.65, 8.66 Hz, 3H), 7.26-7.29 (m, 3H), 7.05 (t, J=8.85 Hz, 2H), 4.37 (s, 2H), 3.54 (s, 2H).

Example 33

(E)-N-(3-((4-(2-(([1,1'-biphenyl]-4-ylmethyl)amino)-2-oxoethyl)phenyl)amino)-1-(4-chlorophenyl)-3-oxoprop-1-en-2-yl)benzamide (KIM-2249V)

This compound was prepared according to the procedure described for the synthesis of KIM-111V starting from oxazolone 7f (2 mmol, 0.539 g) and N-([1,1'-biphenyl]-4-ylmethyl)-2-(4-aminophenyl)acetamide (2.2 mmol, 0.695 g). The product KIM-2249V was white solid, m.p. 242° C.; $^1$H NMR (600 MHz, Acetone) δ 9.53 (s, 1H), 8.07 (d, J=7.91 Hz, 1H), 7.71 (d, J=8.66 Hz, 1H), 7.66 (s, 1H), 7.64 (d, J=2.64 Hz, 1H), 7.63 (s, 1H), 7.60 (s, 1H), 7.58 (s, 1H), 7.52-7.56 (m, 1H), 7.46 (t, J=7.91 Hz, 2H), 7.42 (d, J=8.66 Hz, 1H), 7.37 (d, J=7.91 Hz, 2H), 7.31 (d, J=8.28 Hz, 1H), 7.28 (s, 1H), 4.45 (d, J=6.02 Hz, 1H), 3.57 (s, 1H), 2.84 (s, 5H), 2.81 (s, 3H).

Example 34

(E)-N-(1-(4-chlorophenyl)-3-((4-(2-((3-fluorobenzyl)amino)-2-oxoethyl)phenyl)amino)-3-oxoprop-1-en-2-yl)benzamide (KIM-2250V)

This compound was prepared according to the procedure described for the synthesis of KIM-111V starting from oxazolone 7f (2 mmol, 0.539 g) and 2-(4-aminophenyl)-N-(3-fluorobenzyl)acetamide (2.2 mmol, 0.567 g). The product KIM-2250V was white solid, mp 242° C.; $^1$H NMR (600 MHz, Acetone) δ 8.08 (d, J=7.91 Hz, 2H), 7.71 (d, J=8.66 Hz, 2H), 7.60-7.66 (m, 3H), 7.52-7.58 (m, 3H), 7.39-7.44 (m, J=8.28 Hz, 2H), 7.27-7.36 (m, 4H), 7.11 (d, J=7.15 Hz, 1H), 7.03-7.07 (m, 1H), 6.99 (dt, J=2.45, 8.56 Hz, 1H), 4.41 (s, 2H), 3.56 (s, 2H).

Example 35

Methods for Cytotoxic Activities Against MCF7 and PC3: Cell Culture

MCF-7 (breast) and PC3 (prostate) cancer cells were each grown in RPMI-1640 medium supplemented with 10% heat inactivated FBS, 50 units/mL of penicillin, and 50 mg/mL of streptomycin. The cultures were maintained at 37° C. in a humidified atmosphere containing 5% $CO_2$. The cells were maintained as "monolayer culture" by serial sub-culturing.

Example 36

Methods for Cytotoxic Activities Against MCF7 and PC3: SRB Cytotoxicity Assay

Cytotoxicity was determined using SRB method as previously described by Skehan et al. [Skehan P.; Storeng R.; Scudiero D.; Monks A.; McMahon J.; al., V. D. e., New colorimetric cytotoxicity assay for anticancer drug screening. J Natl Cancer Inst 1990, 82, 1107-12, incorporated herein by reference in its entirety]. Exponentially growing cells were collected using 0.25% Trypsin-EDTA and seeded in 96-well plates at 1000-2000 cells/well in RPMI-1640 supplemented medium. After 24 h, cells were incubated for 72 h with various concentrations of the tested compounds. Following 72 h treatment, the cells would be fixed with 10% trichloroacetic acid for 1 h at 4° C. Wells were stained for 10 min at room temperature with 0.4% SRB dissolved in 1% acetic acid. The plates were air dried for 24 h and the dye was solubilized with Tris-HCl for 5 min on a shaker at 1600 rpm. The optical density (OD) of each well was measured spectrophotometrically at 564 nm with an ELISA microplate reader (ChroMate-4300, FL, USA). The $IC_{50}$ values were calculated according to the equation for Boltzman sigmoidal concentration—response curve using the nonlinear regression fitting models (Graph Pad, Prism Version 5).

Example 37

Methods for Experiments on HL-60 Leukemia Cell Lines: Cell Culture and Reagents

HL-60 were purchased from CLS Cell Line Service GmbH (Eppelheim, Germany) and cultured in Roswell Park Memorial Institute-1640 medium (RPMI-1640; Thermo Fisher Scientific, Inc; Waltham, Mass., USA) supplemented with 10% fetal bovine serum (FBS; Thermo Fisher Scientific) and ciprofloxacin (10 µg/mL; Cipla Limited; Mumbai, India), at 37° C. with 5% $CO_2$ in a humidified incubator.

Example 38

Methods for Experiments on HL-60 Leukemia Cell Lines: Cell Viability Assay

The CellTiter®-Blue Cell Viability assay was acquired from Promega Corporation (Madison, Wis., USA). Cell viability assay was performed as follows. The cells ($10^4$/well) were incubated with a concentration gradient of KIM-161C and KIM-241C ranging from 0.01 to 100 in 96-well plates for 48 h at 37° C. Subsequently, 20 µL CellTiter®-Blue Cell Viability reagent was added to each well and incubated for an additional 2 h for the development of fluorescence. The fluorescence emission was measured at 590 nm using the SpectraMax® i3× Multi-Mode microplate reader (Molecular Devices, LLC; San Jose, Calif., USA.) and plotted against drug concentrations to determine the mean inhibitory concentration of KIM-161C and KIM-241C producing 50% decrease in cell viability (IC50).

Example 39

Methods for Experiments on HL-60 Leukemia Cell Lines: Cell Cycle Analysis

The cells ($3.5 \times 10^5$) were incubated with two different concentrations of KIM-161C at 37° C. for 48 h. Subsequently, the cells were collected and washed twice with ice-cold PBS (1×). The washed cells were fixed on ice for 20 min using a fixation buffer containing paraformaldehyde. Hoechst 33342 (10 µg/mL; Thermo Fisher Scientific, Inc.) was used for staining. The cells were then incubated in the dark for 30 min on ice. A minimum total of 20,000 events were acquired using a BD FACSAria III flow cytometer. Flowlogic version 7.2.1 software (Inivai Technologies, Victoria, Australia) was used to obtain the percentages of cells in the G1, S, and G2/M phases in the singlet-gated population.

Example 40

Methods for Experiments on HL-60 Leukemia Cell Lines: Apoptosis Detection by Caspase 3 Activity The caspase family of cysteine proteases are important regulators in the apoptosis. Caspase 3 belongs to the effector (caspase 3, 6 and 7) class of proteases and it is a key protease that is activated during early stages of apoptosis. Like other proteases, caspase 3 is present in the cell as inactive zymogens that can be activated through proteolytic processing at conserved aspartic residue. The activated caspase 3 is a marker for cell apoptosis that proteolytically cleaves and activates other caspases and intracellular targets [Patel, T.; Gores, G. J.; Kaufmann, S. H., The role of proteases during apoptosis. *FASEB journal: official publication of the Federation of American Societies for Experimental Biology* 1996, 10 (5), 587-97].

FITC conjugated active caspase-3 antibody (BD biosciences, USA) was used to detect the active form of caspase 3 in the cells undergoing apoptosis. Briefly, cells were plated in a 6-well culture plate at a density of $0.5 \times 10^6$ cells and harvested after 24 hours of incubation with the inhibitor treatment. The collected cells were washed twice in cold 1×PBS and then re-suspended in a 0.5 mL BD Cytofix/Cytoperm solution followed by 20 min incubation on ice. After incubation, cells were washed twice in a BD Perm/Wash buffer (1×) and then labelled with 5 µL of FITC rabbit anti-caspase 3 antibodies. The labelled cells were washed again with wash buffer and re-suspended in a 0.5 mL buffer and analyzed by acquiring a minimum of 5000 events on the FACS Aria III cell analyzer and sorter.

Example 41

Cytotoxic Assays Against MCF7 (Breast) and PC3 (Prostate) Cancer Cell Lines: Results As discussed above, the compounds were screened for their anticancer activities against variety of cell lines. Results are illustrated in Table 1.

TABLE 1

| | | MCF7 | PC3 |
|---|---|---|---|
| Code | MWt | IC$_{50}$ (µM) | IC$_{50}$ (µM) |
| KIM-111C | 409.48 | 11.58 | 1.667 |
| KIM-121C | 443.93 | 20.82 | 6.86 |
| KIM-131C | 455.5 | 9.48 | 5.83 |
| KIM-161C | 439.5 | 3.5 | 2.13 |
| KIM-211C | 471.54 | 34.85 | 41.68 |
| KIM-221C | 505.99 | 44.25 | 74.16 |
| KIM-231C | 517.57 | 35.1 | 37.51 |
| KIM-241C | 461.51 | 0.145 | 0.243 |
| KIM-261C | 501.57 | 32.07 | 38.68 |
| KIM-111V | 427.49 | >100 | >100 |
| KIM-131V | 473.52 | 53.54 | 61.27 |
| KIM-121V | 443.92 | >100 | 57.3 |
| KIM-161V | 457.52 | 44.28 | 41.1 |
| KIM-211V | 489.56 | >100 | >100 |
| KIM-221V | 524 | 3.12 | 4.079 |
| KIM-231V | 535.58 | >100 | >100 |
| KIM-261V | 519.59 | >100 | >100 |
| KIM-2101V | 521.58 | >100 | >100 |
| KIM-22101V | 509.98 | >100 | >100 |
| KIM-2216V | 554.04 | >100 | >100 |
| KIM-2230V | 513.97 | >100 | 97.77 |
| KIM-2245V | 538.04 | >100 | >100 |
| KIM-2246V | 538.04 | >100 | >100 |
| KIM-2247V | 538.04 | >100 | >100 |
| KIM-2248V | 542.00 | 89.63 | 85.11 |
| KIM-2249V | 600.11 | 87.52 | 92.15 |
| KIM-2250V | 542.00 | >100 | >100 |
| KIM-112V | 294.35 | >100 | >100 |

Example 42

Figure 8:
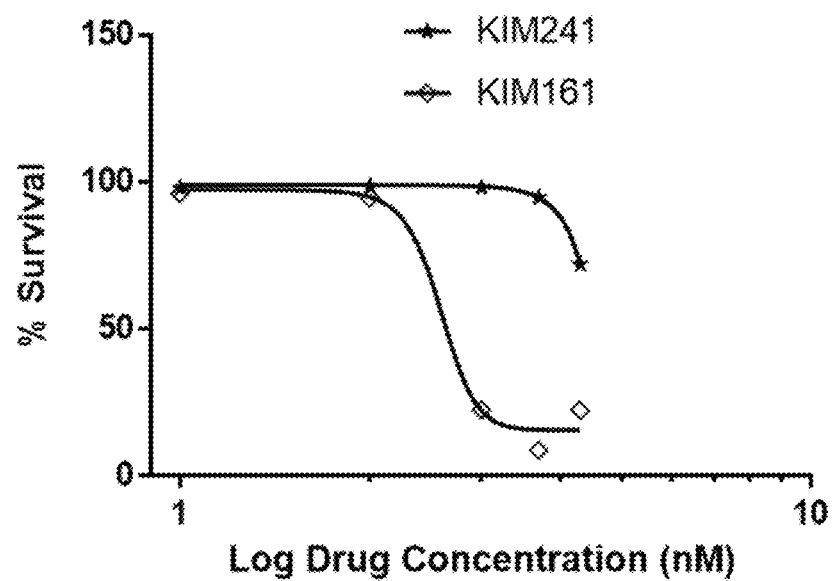
FIG. 8 is an overlay of dose-response curves of HL-60 leukemia cells upon treatment with increasing concentrations of compounds KIM-161C and KIM-241C.
Figure 9A:
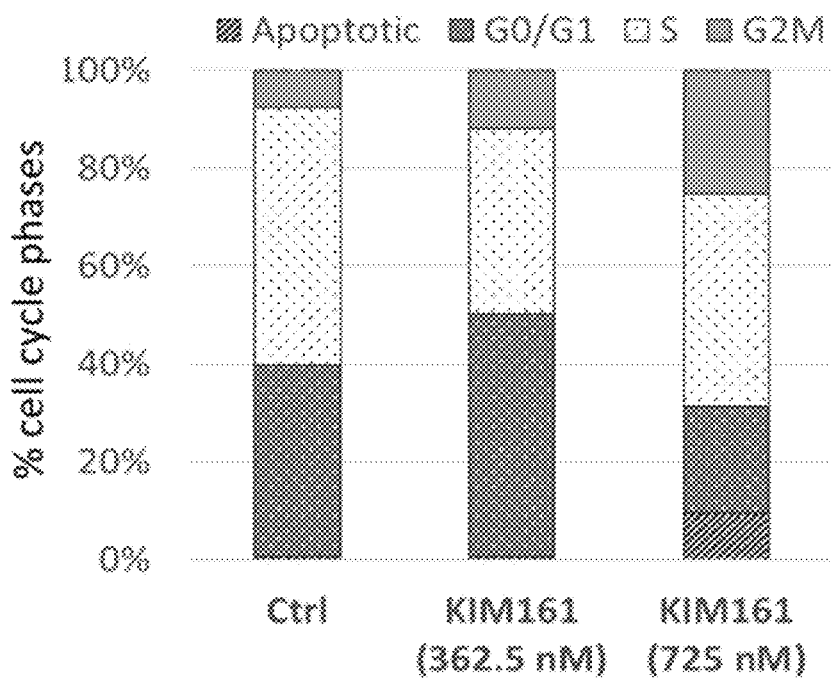
FIG. 9A is a bar graph summarizing the effect of compound KIM-161C on different cell cycle stages of HL-60 leukemia cells.
Figure 9B:
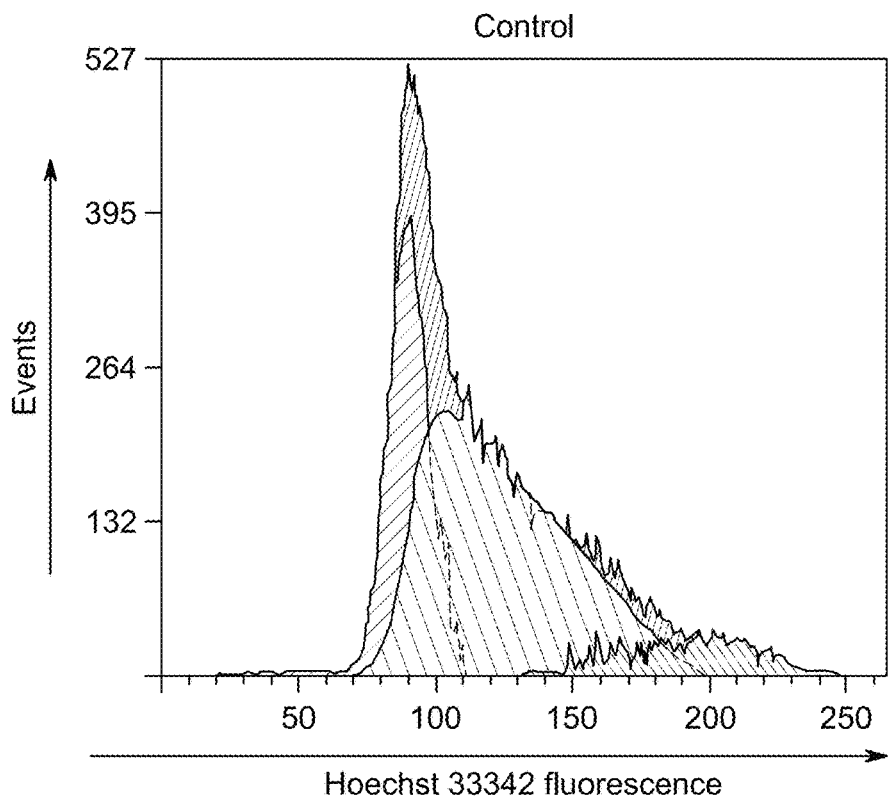
FIG. 9B shows different cell cycle stages of HL-60 leukemia cells upon treatment of blank control (i.e. cells grown in the absence of any compound).
Figure 9C:
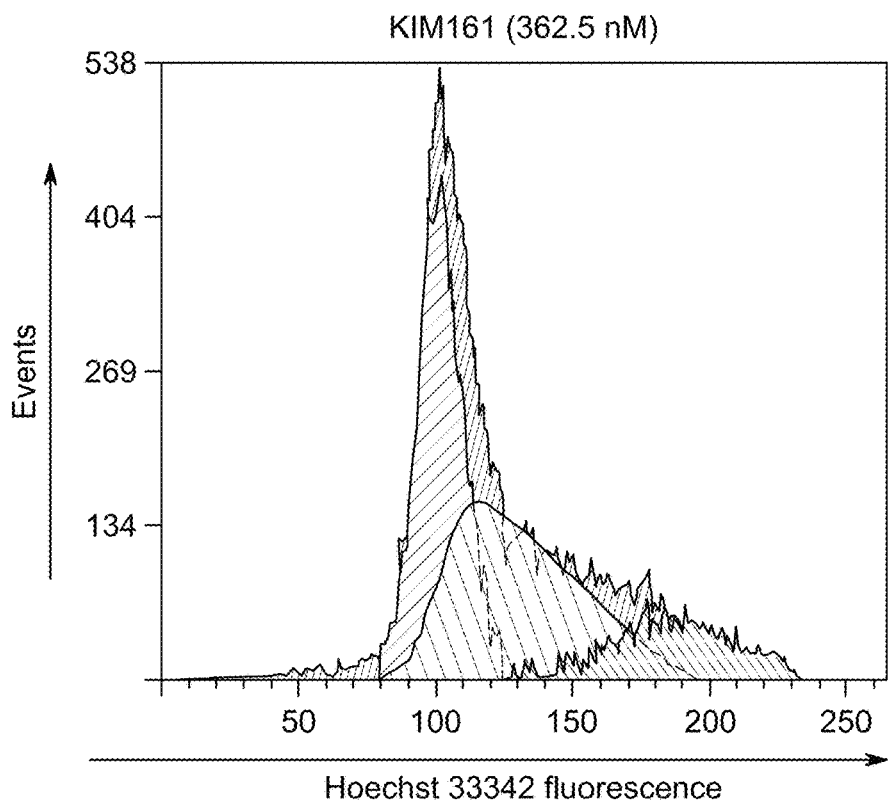
FIG. 9C shows different cell cycle stages of HL-60 leukemia cells upon treatment of KIM-161C at a concentration of 362.5 nM.
Figure 9D:
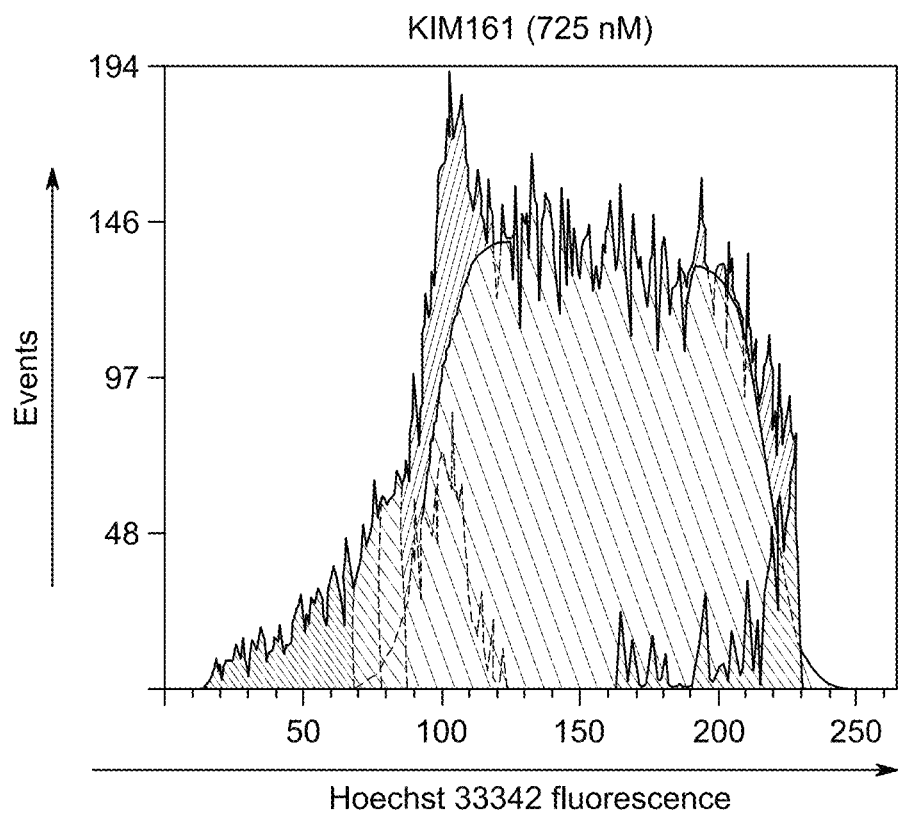
FIG. 9D shows different cell cycle stages of HL-60 leukemia cells upon treatment of KIM-161C at a concentration of 725 nM.
Figure 10A:
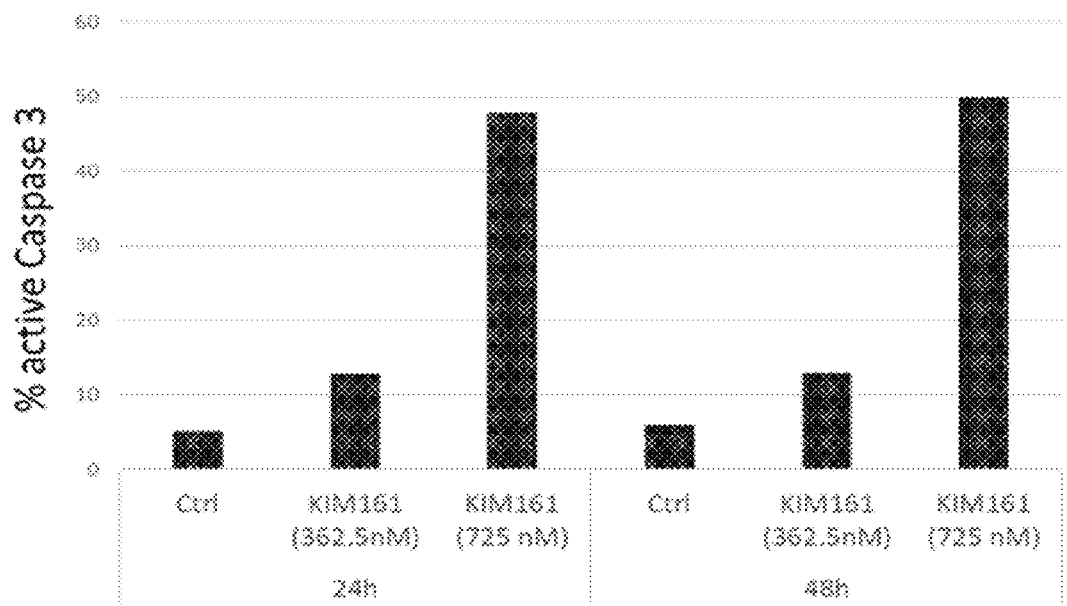
FIG. 10A is a bar graph summarizing the effect of KIM-161C on apoptosis in HL-60 leukemia cells.
Figure 10B:
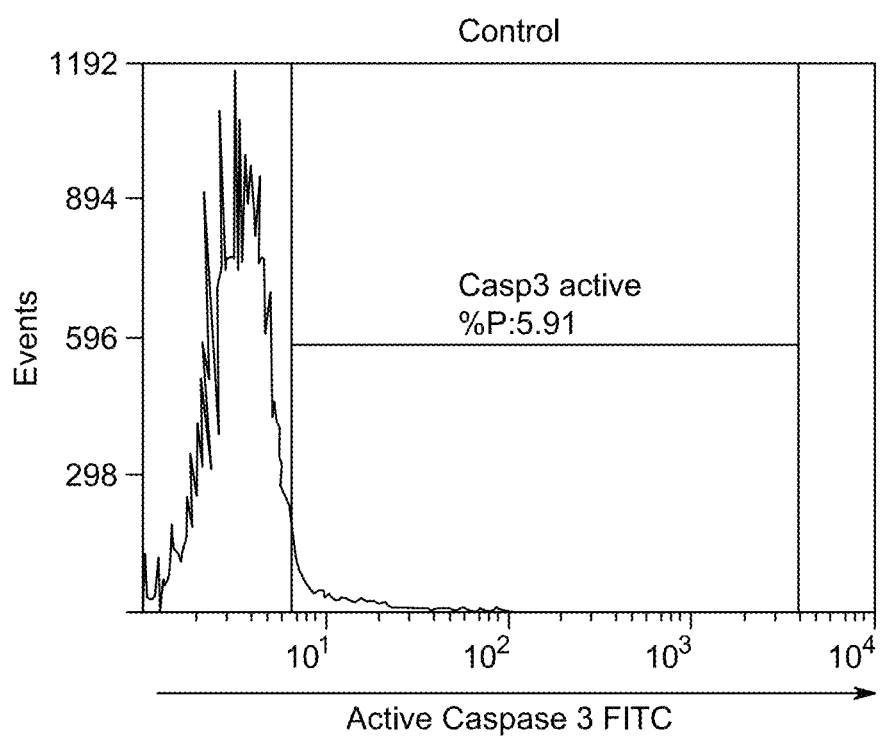
FIG. 10B is a histogram showing Caspase-3 activity of HL-60 leukemia cells upon treatment of blank control (i.e. cells grown in the absence of any compound) for 24 hours.
Figure 10C:
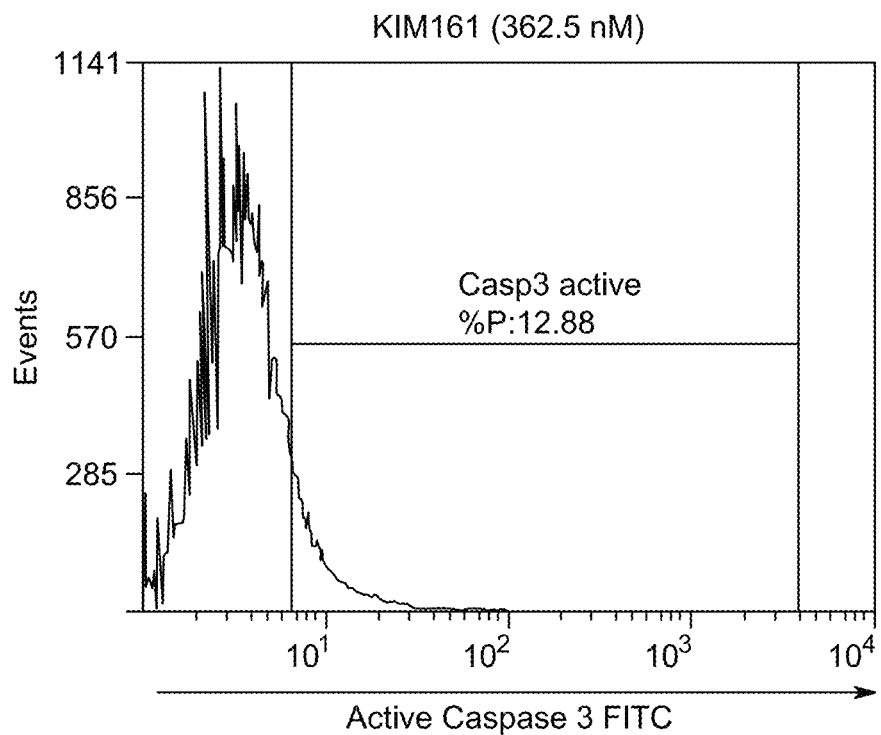
FIG. 10C is a histogram showing Caspase-3 activity of HL-60 leukemia cells upon treatment of KIM-161C at a concentration of 362.5 nM for 24 hours.
Figure 10D:
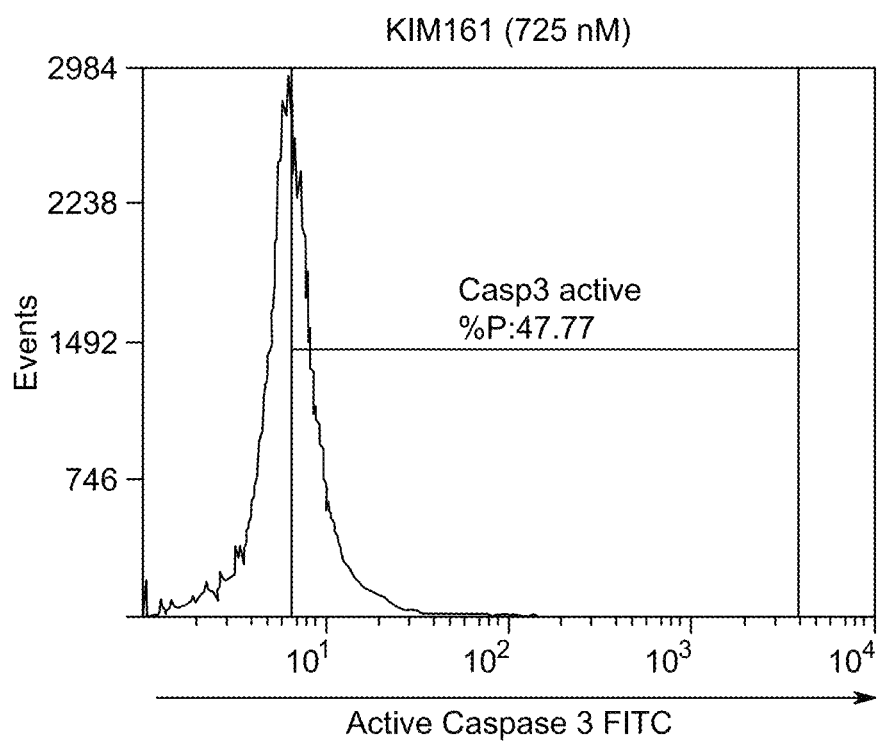
FIG. 10D is a histogram showing Caspase-3 activity of HL-60 leukemia cells upon treatment of KIM-161C at a concentration of 725 nM for 24 hours.
Figure 10E:
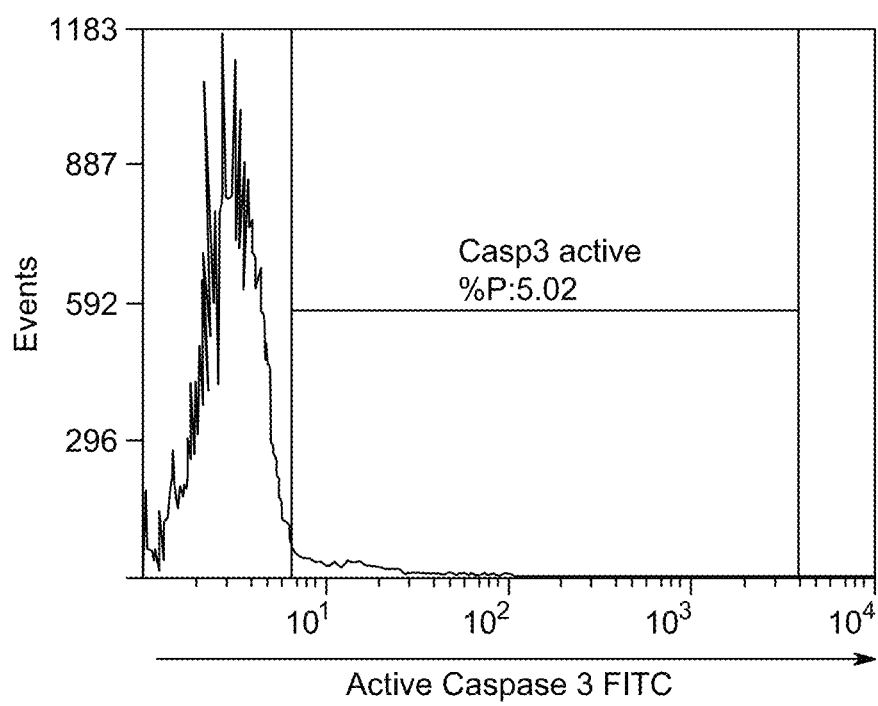
FIG. 10E is a histogram showing Caspase-3 activity of HL-60 leukemia cells upon treatment of blank control (i.e. cells grown in the absence of any compound) for 48 hours.
Figure 10F:
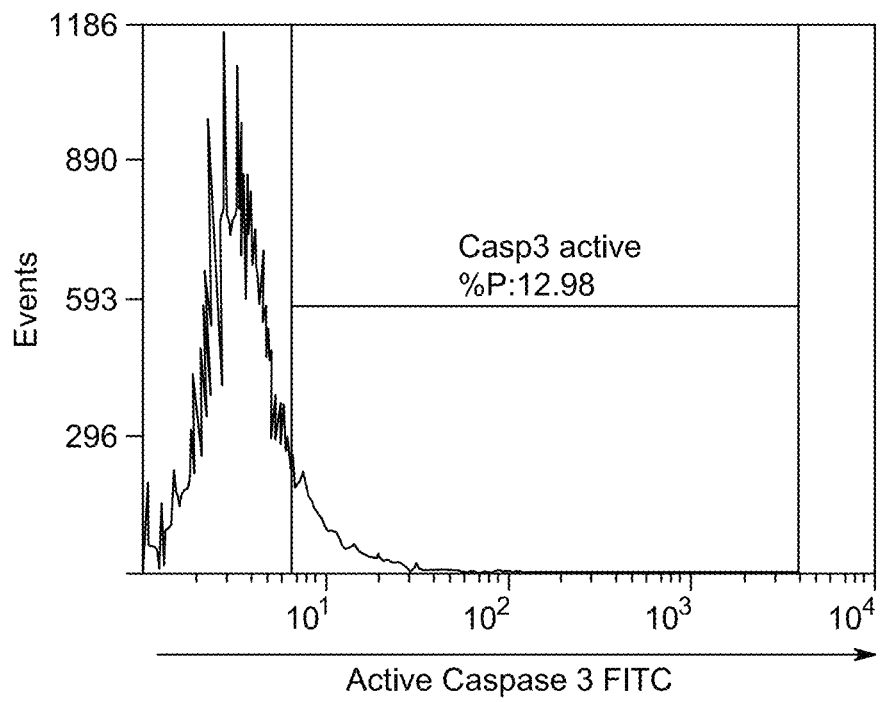
FIG. 10F is a histogram showing Caspase-3 activity of HL-60 leukemia cells upon treatment of KIM-161C at a concentration of 362.5 nM for 48 hours.
Figure 10G:
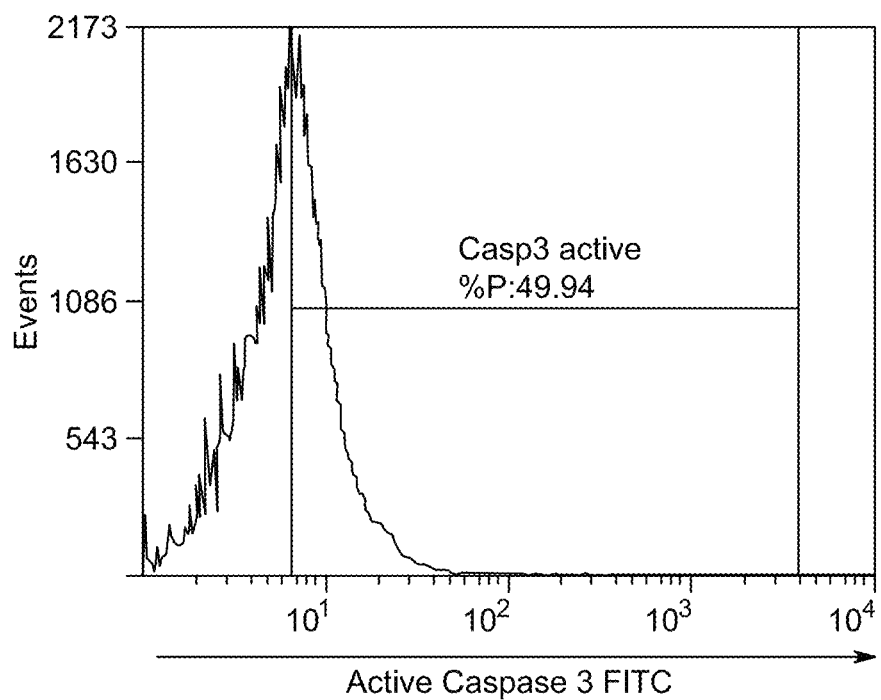
FIG. 10G is a histogram showing Caspase-3 activity of HL-60 leukemia cells upon treatment of KIM-161C at a concentration of 725 nM for 48 hours.

Cytotoxic Activity of KIM-161C and KIM-241C Against Leukemia H60 Cell Lines and their Mechanism of Action In order to confirm the activity of KIM-161C and KIM-241C, cell viability experiments were performed on HL-60 cells in the absence or presence of a range of drug concentration gradients. KIM-161C demonstrated an IC$_{50}$ value of 262.5 nM, whereas the IC$_{50}$ value of KIM-241C could not be obtained even at a concentration of 20 µM drug (FIG. 8). Therefore, it was decided that further investigations on mechanisms of cellular activities were conducted for KIM-161C only.

In order to understand the mechanism of action of KIM-161C, cell cycle analysis of Hoechst 33342 stained HL-60 cells was performed using flow cytometry. HL-60 cells were first incubated with the IC$_{50}$ dose and the 2×IC$_{50}$ doses of KIM-161C for 48 h. At the lower dose, i.e., 362.5 nM, KIM-161C led to an increase in cells in the G1 phase. KIM-161C at 725 nM led to a 3-fold increase in the cells in G2/M stage as compared to the control. The G2/M arrest appeared to be mediated by anti-tubulin polymerization properties of KIM-161C (FIGS. 9A-D).

HL-60 cells are known to be dependent on Src kinases for differentiation. Inhibition of Src kinase mediated activation of STAT3 leads to apoptosis in HL-60 cells [Zhao, W. et al., orafenib induces apoptosis in HL60 cells by inhibiting Src kinase-mediated STAT3 phosphorylation, *Anti-Cancer Drugs* 2011, 22, 1, p 79-88, incorporated herein by reference in its entirety]. We therefore performed apoptosis assay to detect caspase-3 activity (FIGS. 10A-G). Treatment of HL60 cells with 362.5 nM of KIM-161C demonstrate more than 2-fold increase in the cells undergoing apoptosis as compared to the basal apoptosis in HL-60 cells at both 24 and 48 h of treatment. Treatment of HL60 cells with 725 nM of KIM-161C demonstrated more than 9.5-fold and 8.45-fold increase in the cells undergoing apoptosis as compared to the basal apoptosis in HL-60 cells at both 24 and 48 h of treatment, respectively.

Example 43

In summary, two sets of compounds, 5-oxo-4,5-dihydro-1H-imidazol-1-yl (KIM-C series) and 3-aryl-2-acylaminopropenamido (KIM-V series) individually attached to N-benzylphenylacetamide pharmacophore, are provided herein. Both sets of compounds were synthesized using similar synthetic schemes that differ in the final step. Synthesized compounds were confirmed by spectral analyses, and tested for their anticancer activities against breast and prostate cell lines. The compounds effectively inhibit cancer cell growth.

Mechanistic studies showed that these compounds affect cell division at the mitosis stage and also promote apoptotic cell death. Therefore, it is likely that the disclosed compounds act via dual inhibition of Src kinase and tubulin. These compounds can be further developed for clinical applications in treating several types of solid and liquid tumors.

The invention claimed is:

1. A compound selected from the group consisting of

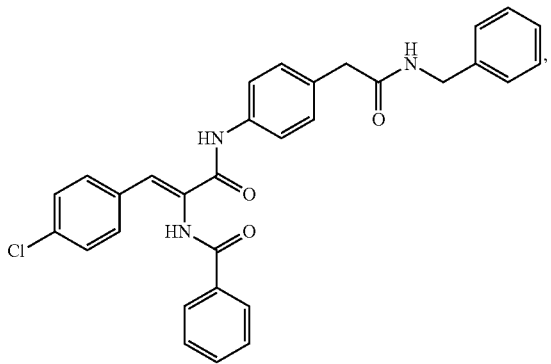 [SMILES: O=C(Cc1ccc(NC(=O)/C(=C/c2ccc(Cl)cc2)NC(=O)c2ccccc2)cc1)NCc1ccccc1]

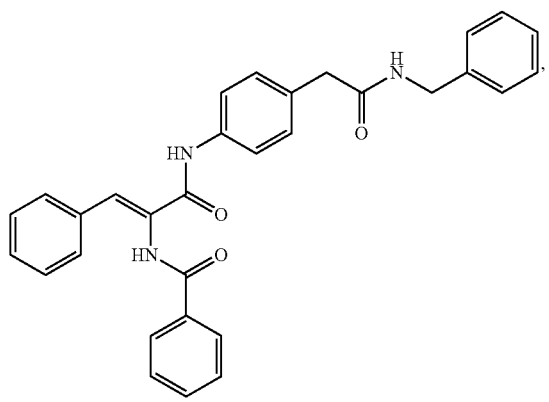

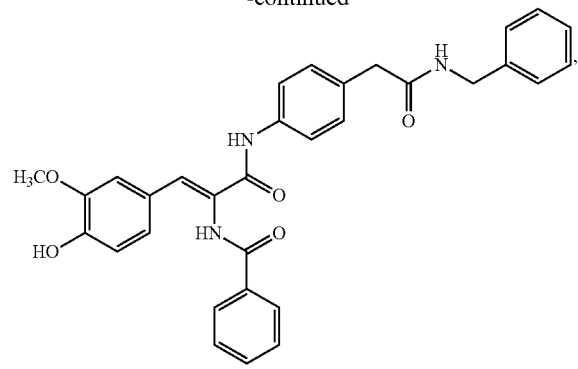
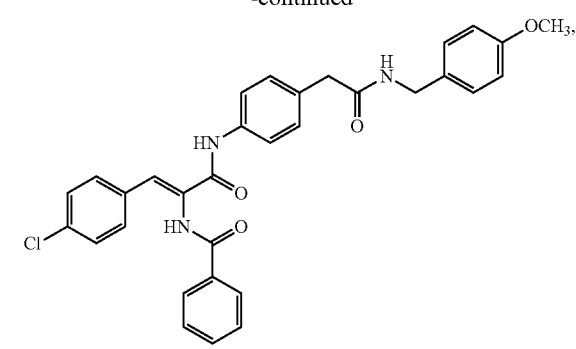
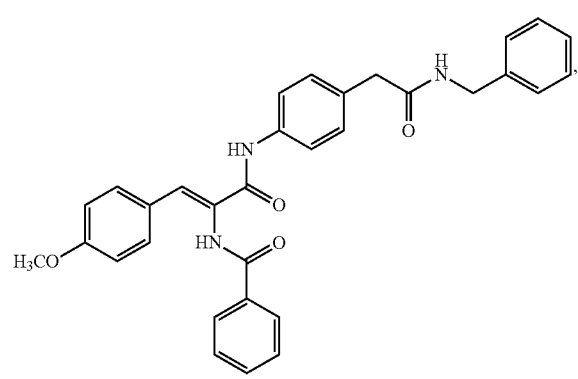
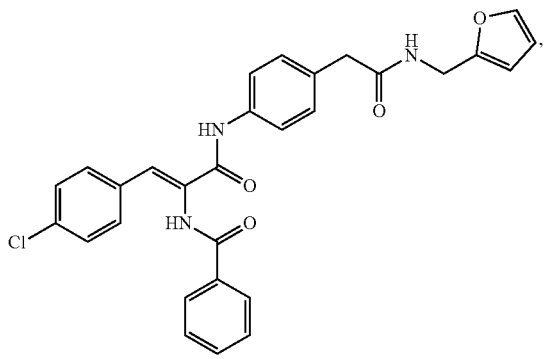
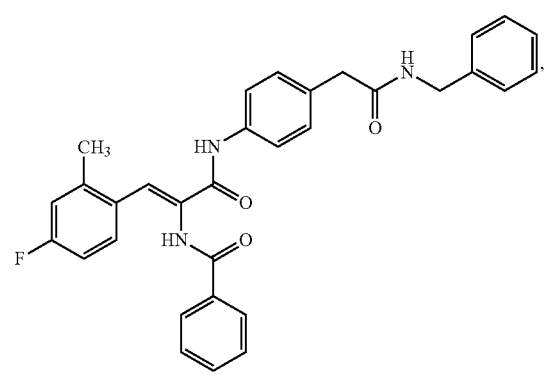
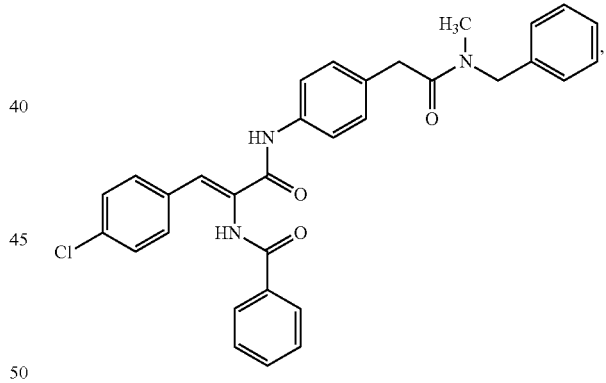
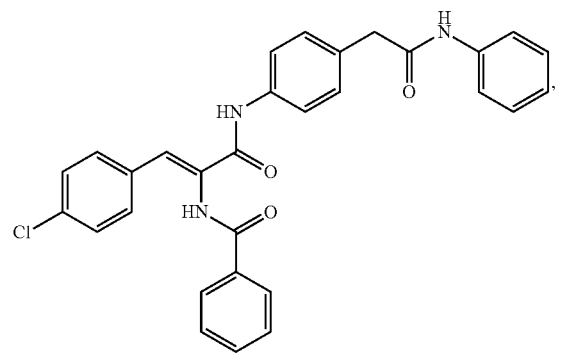
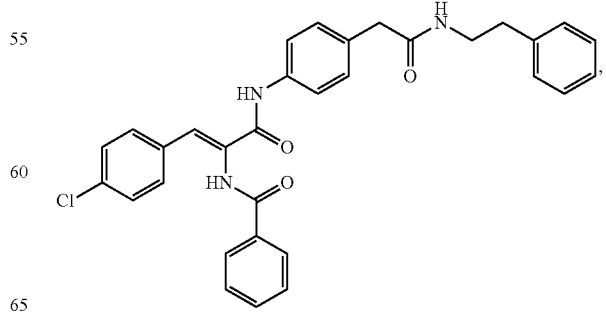

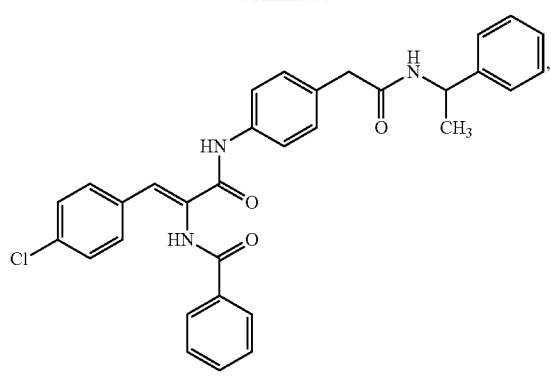 [SMILES: O=C(Cc1ccc(NC(=O)/C(=C/c2ccc(Cl)cc2)NC(=O)c2ccccc2)cc1)NCc1ccccc1]

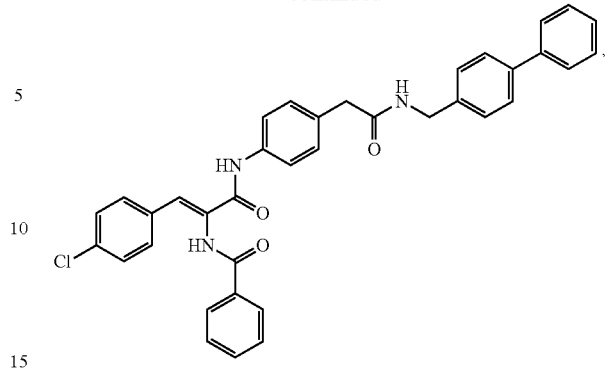

and

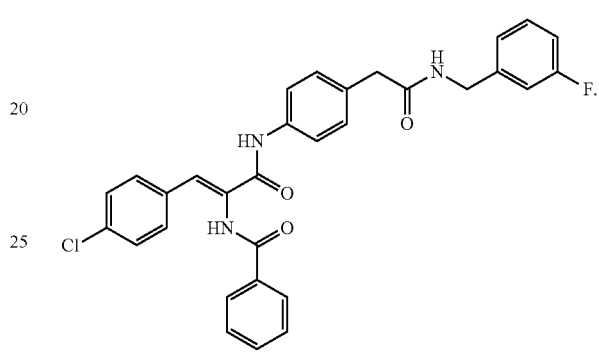

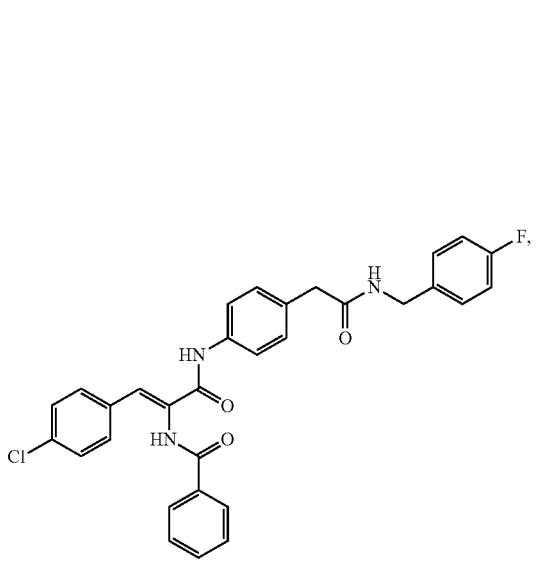

2. A pharmaceutical composition, comprising:
the compound of claim 1; and
a pharmaceutically acceptable carrier and/or excipient.

3. The pharmaceutical composition of claim 2, wherein the pharmaceutically acceptable carrier and/or excipient is at least one selected from the group consisting of a buffer, an inorganic salt, a fatty acid, a vegetable oil, a synthetic fatty ester, a surfactant, and a polymer.

* * * * *